US012599424B2

(12) United States Patent
Garcia-Meza et al.

(10) Patent No.: US 12,599,424 B2
(45) Date of Patent: Apr. 14, 2026

(54) CRYOGENIC CATHETER PROBE, SYSTEM, AND METHOD FOR SELECTIVE ABLATION OF MUCOSA AND SUBMUCOSA OF THE GASTROINTESTINAL TRACT

(71) Applicant: Ágil Therapeutics, Inc., San Francisco, CA (US)

(72) Inventors: Peter Garcia-Meza, San Francisco, CA (US); Timothy D. Holland, Los Gatos, CA (US)

(73) Assignee: AGIL THERAPEUTICS, INC., San Francisco, CA (US)

( * ) Notice: Subject to any disclaimer, the term of this patent is extended or adjusted under 35 U.S.C. 154(b) by 298 days.

(21) Appl. No.: 18/568,225

(22) PCT Filed: Jun. 7, 2022

(86) PCT No.: PCT/US2022/032573
§ 371 (c)(1),
(2) Date: Dec. 7, 2023

(87) PCT Pub. No.: WO2022/261146
PCT Pub. Date: Dec. 15, 2022

(65) Prior Publication Data
US 2024/0268877 A1 Aug. 15, 2024

Related U.S. Application Data

(60) Provisional application No. 63/197,980, filed on Jun. 7, 2021.

(51) Int. Cl.
*A61B 18/02* (2006.01)
*A61B 18/00* (2006.01)

(52) U.S. Cl.
CPC .................... *A61B 18/0218* (2013.01); *A61B 2018/00488* (2013.01); *A61B 2018/00494* (2013.01);

(Continued)

(58) Field of Classification Search
CPC ................ A61B 18/02; A61B 18/0218; A61B 2018/00184; A61B 2018/00196;

(Continued)

(56) References Cited

U.S. PATENT DOCUMENTS 7,819,836 B2  10/2010  Levine et al.
9,757,535 B2   9/2017  Rajagopalan et al.

(Continued)

FOREIGN PATENT DOCUMENTS

WO        2022239008 A1    11/2022

OTHER PUBLICATIONS

PCT/US2023/075176 International Search Report and Written Opinion mailed Feb. 20, 2024.

(Continued)

*Primary Examiner* — Daniel W Fowler
(74) *Attorney, Agent, or Firm* — FisherBroyles, LLP; James W. Hill; Andrew K. Gonsalves

(57) ABSTRACT

Disclosed is a cryogenic catheter probe, cryogenic ablation system, and use thereof for performing cryogenic ablation of mucosal tissue and/or of both mucosal tissue and submucosal tissue in the gastrointestinal tract of a subject. The cryogenic catheter probe includes a chamber and a channel assembly housed within the chamber. The channel assembly includes a central rail, at least one cryogenic fluid delivery channel, a delivery channel guide, and a sprayer guide. The at least one cryogenic fluid delivery channel has a fluid delivery channel portion and a sprayer connected to the fluid delivery channel portion, and is mounted on the central rail for longitudinal movement along the central rail. The sprayer is configured to release cryogenic spray in at least one treatment zone along the hollow body portion of the chamber.

17 Claims, 24 Drawing Sheets

(52) U.S. Cl.
CPC .................. *A61B 2018/005* (2013.01); *A61B 2018/00577* (2013.01); *A61B 2018/00642* (2013.01); *A61B 2018/00708* (2013.01); *A61B 2018/00744* (2013.01); *A61B 2018/00773* (2013.01); *A61B 2018/0212* (2013.01)

(58) Field of Classification Search
CPC .. A61B 2018/0022; A61B 2018/00482; A61B 2018/00488; A61B 2018/00494; A61B 2018/008; A61B 2018/00577; A61B 2018/00642; A61B 2018/00708; A61B 2018/00744; A61B 2018/00773; A61B 2018/0212

See application file for complete search history.

(56) References Cited

U.S. PATENT DOCUMENTS

| | | | |
|---|---|---|---|
| 10,537,387 | B2 | 1/2020 | Ben Oren et al. |
| 10,575,904 | B1 | 3/2020 | Ben Oren et al. |
| 10,610,663 | B2 | 4/2020 | Rajagopalan et al. |
| 10,687,890 | B2* | 6/2020 | Fang ..................... A61B 5/287 |
| 11,185,367 | B2 | 11/2021 | Rajagopalan et al. |
| 2005/0209587 | A1 | 9/2005 | Joye et al. |
| 2012/0101485 | A1* | 4/2012 | Wittenberger .... A61M 25/0147 606/21 |
| 2013/0281996 | A1 | 10/2013 | Ingle et al. |
| 2015/0018904 | A1 | 1/2015 | Lafontaine |
| 2015/0031946 | A1 | 1/2015 | Saadat et al. |
| 2015/0126985 | A1 | 5/2015 | Newell et al. |
| 2015/0148738 | A1 | 5/2015 | Caplan et al. |
| 2015/0196345 | A1 | 7/2015 | Newell et al. |
| 2016/0135864 | A1 | 5/2016 | Babkin |
| 2019/0059970 | A1 | 2/2019 | Newell et al. |
| 2021/0177482 | A1* | 6/2021 | Tegg ..................... A61B 18/02 |
| 2022/0079649 | A1 | 3/2022 | Mulcahey |

OTHER PUBLICATIONS

Better Health Channel, "Diabetes—long—term—effects", www.betterhealth.vic.gov.au/health/conditionsandtreatments/diabetes-long-term-effects.

Betzel et al., "Clinical follow-up on weight loss, glycemic control, and safety aspects of 24 months of duodenal-jejunal bypass liner implantation", Surgical Endoscopy, 2020, vol. 34(1), pp. 209-215, DOI: 10.1007/s00464-019-06752-8.

Cherrington et al., "Hydrothermal Duodenal Mucosal Resurfacing: Role in the Treatment of Metabolic Disease", Gastrointest Endoscopy Clinic of North America, Apr. 2017, vol. 27, Issue 2, pp. 299-311, DOI: 10.1016/j.giec.2016.12.002, PMID: 28292408.

ClinicalTrials.gov Identifier—NCT03390322, (clinicaltrials.gov/ct2/show/NCT03390322).

Dhaliwal et al., "Mo1275 Comparative Assessment of the Structural and Functional Integrity of the Neo-Squamous Epithelium following endoscopic therapy in Barrett's esophagus: A Pilot Study", Gastrointestinal Endoscopy, 2020, Poster Abstracts| vol. 91, Issue 6, Supplement, AB412, www.giejournal.org.

Erinjeri et al., "Cryoablation: Mechanism of Action and Devices", J Vasc Interv Radiol, Aug. 2010, 21(8 Suppl), pp. S187-191, DOI: 10.1016/j.jvir.2009.12.403, PMID: 20656228; PMCID: PMC6661161.

Liebl et al., "Evaluation of risk factors for development of complications in Type II diabetes in Europe", Diabetologia, Jun. 19, 2002, 45:S23-S28, DOI: 10.1007/s00125-002-0863-0.

Pories et al., "Etiology of Type II Diabetes Mellitus: Role of the Foregut", World Journal of Surgery, Apr. 2001, vol. 25, pp. 527-531, DOI: 10.1007/s002680020348, Abstract.

Sjostrom et al., "Lifestyle, Diabetes, and Cardiovascular Risk Factors 10 Years After Bariatric Surgery", The New England Journal of Medicine, Dec. 23, 2004, vol. 351, No. 26, pp. 2683-2693.

Van Baar et al., "Endoscopic duodenal mucosal resurfacing for the treatment of type 2 diabetes mellitus: one year results from the first international, open-label, prospective, multicentre study", Gut, 2020, 69(2), pp. 295-303, DOI: 10.1136/gutjnl-2019-318349.

Van Baar et al., "The Duodenum harbors a Broad Untapped Therapeutic Potential", Gastroenterology, Mar. 2018, 154(4), pp. 773-777, DOI: 10.1053/j.gastro.2018.02.010.

Yakkala et al., "Cryoablation and Immunotherapy: An Enthralling Synergy to Confront the Tumors", Front of Immunology, Sep. 2019, vol. 10, Article 2283, pp. 1-12, DOI: 10.3389/fimmu.2019.02283.

Zervos et al., "Amelioration of Insulin Requirement in Patients Undergoing Duodenal Bypass for Reasons Other than Obesity Implicates Foregut Factors in the Pathophysiology of Type II Diabetes, Journal of the American College of Surgeons, May 2010, 210(5), pp. 564-572, 572-574, DOI: 10.1016/j.jamcollsurg.2009.12.025, PMID: 20421005, Abstract.

International Application No. PCT/US23/82782 International Search Report and Written Opinion mailed May 1, 2024.

* cited by examiner

CRYOGENIC ABLATION SYSTEM

CONTROLLER

HANDLE

CATHETER

CONTROLLER CONNECTOR

ENDOSCOPE

DUODENUM

STOMACH

AGIL'S CRYOABLATION

CONTROLLER

LOAD CAP          LOAD CAP

FRONT PANEL                    DISPLAY

CONTROLLER

LOAD CAP          LOAD CAP

POLE
INSERTION
HOLE

MOUNTING
BLOCK

MOUNTING
WHEEL

BLOCK BODY

CRYOGENIC FLUID

PROBE INNER SURFACE

TREATMENT ZONE

SPRAYER(S)

CRYOGENIC FLUID

PROBE WALL

TREATMENT ZONE

PROBE INNER SURFACE

CRYOGENIC FLUID

TREATMENT ZONE

SPRAYER(S)

CRYOGENIC FLUID

PROBE WALL

TREATMENT ZONE

TRI-CORE DESIGN    PROBE WALL

PROBE INNER SURFACE

CRYOGENIC FLUID DELIVERY CHANNEL ASSEMBLY

PRESSURE DETECTION TUBE

DELIVERY CHANNEL(S)

SPRAYER(S)

SPRAYER GUIDE

CENTRAL RAIL

SHAFT

CRYOGENIC FLUID

CRYOGENIC FLUID DELIVERY CHANNEL ASSEMBLY

SPRAYER GUIDE

DELIVERY CHANNEL

CENTRAL RAIL

SPRAYER

SPRAYER

DELIVERY CHANNEL

CENTRAL RAIL

CENTRAL RAIL

CENTRAL RAIL

CENTRAL RAIL

GUIDING SLEEVE

GUIDING HUB

TO CATHETER

DELIVERY CHANNELS

ALIGNMENT PINS

LOCKING PINS

CONTOURING CORE

HIGH-PRESSURE CATHETER CONNECTOR

CONTOURING HUB

O-RINGS

THREADED SHAFTS

HIGH PRESSURE PLATE

LOCKING SLEEVE

TO CONTROLLER

HUB CAP

HIGH-PRESSURE CATHETER CONNECTOR CAP

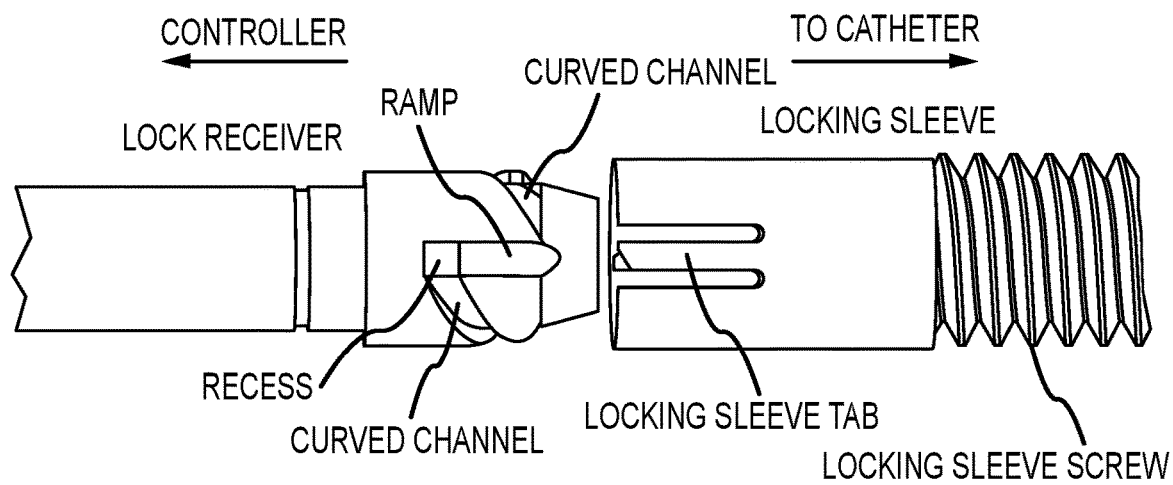

CONTROLLER ←     → TO CATHETER

LOCK RECEIVER     RAMP     CURVED CHANNEL     LOCKING SLEEVE

RECESS     CURVED CHANNEL     LOCKING SLEEVE TAB     LOCKING SLEEVE SCREW

FIG.23

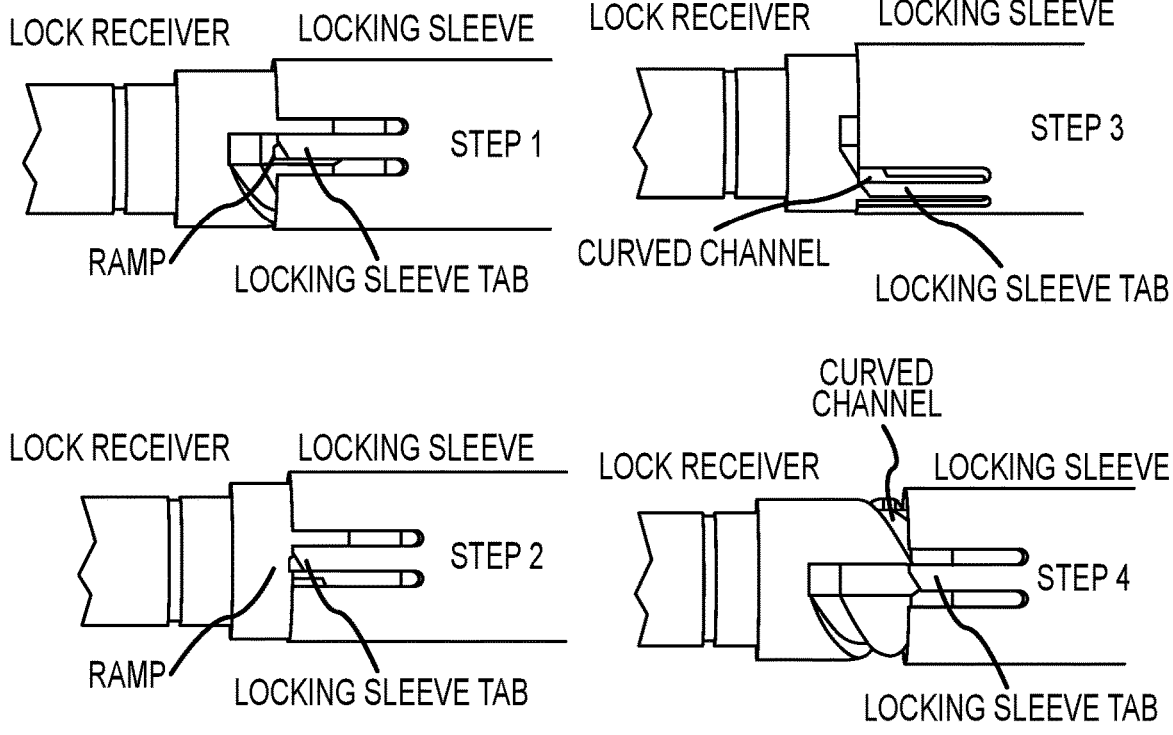

LOCK RECEIVER     LOCKING SLEEVE
STEP 1
RAMP     LOCKING SLEEVE TAB

LOCK RECEIVER     LOCKING SLEEVE
STEP 3
CURVED CHANNEL     LOCKING SLEEVE TAB

LOCK RECEIVER     LOCKING SLEEVE
STEP 2
RAMP     LOCKING SLEEVE TAB

CURVED CHANNEL
LOCK RECEIVER     LOCKING SLEEVE
STEP 4
LOCKING SLEEVE TAB

FIG.24

VILLI

MUCOSA

SUBMUCOSA

MUSCULARIS

EEC

VILLI

CRYPT

SUBMUCOSAL PLEXUS

MYENTERIC PLEXUS

CRYOGENIC CATHETER PROBE, SYSTEM, AND METHOD FOR SELECTIVE ABLATION OF MUCOSA AND SUBMUCOSA OF THE GASTROINTESTINAL TRACT

CROSS-REFERENCE TO RELATED APPLICATIONS

This application claims priority benefit of U.S. Provisional Patent Application No. 63/197,980, filed Jun. 7, 2021, the disclosure of which is hereby incorporated by reference herein in its entirety.

FIELD OF THE DISCLOSURE

The present disclosure generally relates to, inter alia, catheter probes, catheters, systems, and methods of using the catheter probes, catheters, and systems for cryogenic ablation of tissue, particularly of the gastrointestinal tract.

BACKGROUND OF THE DISCLOSURE

The use of freezing for the ablation of unwanted tissue in medical applications has been used since the 1800's. The application of freezing temperature to tissue or cryoablation forms intracellular ice crystals which result in damage to cellular organelles and plasma membrane. Additionally, the free water is drawn during the freeze process, resulting in tonicity increase of the extracellular space. The increased solute concentration draws out the intracellular water, resulting in damage to cytoplasmic proteins and the destabilization of the cellular membrane. Although the exact mechanism of cell death is not known in cryoablation, the primary thought is that the disruption to the organelle membrane (i.e., mitochondria) and cellular plasma membrane initiates the cell death process. In particular, ice formation increases mitochondrial membrane permeability, which leads to disruption of the electron transport chain and irreversible mitochondrial de-energization, resulting in cell death. Cryoablation has shown to leave the acellular structural scaffolding (extracellular matrix) intact. Maintaining the structure allows for improved long-term regeneration of the tissue.

In contrast, high-temperature based ablation (e.g., radiofrequency ablation (RFA), microwave ablation, high-intensity focused ultrasound, laser, steam, hot-balloon) causes a coagulative denaturation to both cellular and acellular tissue structures. Further damage to the acellular tissue structure may result in severe unintended damage to the treated tissue, such as esophageal perforation and atrial-esophageal fistula. Additionally, a more intense inflammatory response is often observed in heat-based methods, as compared to cryo-based procedures.

The inflammatory response due to cryoablation, particularly in the submucosa, signals for the clearing of damaged cellular debris and initiation of tissue remodeling. All the commonly employed ablation therapies, such as radiofrequency ablation (RFA), microwave ablation, high-intensity focused ultrasound, laser, steam, and hot-balloon operate on the principle of hyperthermia. Only cryoablation, which is a hypothermic modality, induces tissue damage by a freeze-thaw process. Further, cryoablation causes minimal disruption to the microvasculature and extracellular matrix (ECM) particularly in the submucosa allowing for remodeling of the tissue layers with minimal to no fibrotic scar formation. An intact ECM provides cells with a scaffold for cellular migration, proliferation, and differentiation for tissue renewal.

Type 2 diabetes is a chronic condition that affects how the body metabolizes glucose. The effects of diabetes are staggering (over 10% of the US population has diabetes) to include being at higher risk of cardiovascular disease, retinopathy/macular oedema/glaucoma, nephropathy, neuropathy, and other conditions (1). Conventional medical treatment of type 2 diabetes only partially achieves adequate glycemic control and a reduction in cardiovascular risk (2). Thus, other approaches are needed.

Although developed as a weight reduction therapy, gastric-bypass surgery such as RYGB (Roux-en-Y bypass) has been reported to improve or eliminate type 2 diabetes in 70 to 80% of postoperative patients (3). The rapidity of the correction of glucose concentration in the blood and good glycemic regulation might be a result of the secondary alteration in incretin (hormonal) signals from the antrum, duodenum, and the proximal jejunum to the pancreatic islets (4). RYGB has shown to decrease or eliminate hormonal or neural signal(s) that normally would emanate from the stomach, pylorus, duodenum, or jejunum upon exposure to nutrient passage through the gastrointestinal tract. While effective, RYGB carries a substantial risk of surgical morbidity and mortality. Endoscopic interventions that combine the remarkable effectiveness of RYGB while minimizing associated risks would be a highly desirable addition to available treatments.

A technique that mimics RYGB is the DJBS (duodenal-jejunal bypass sleeve). Unlike RYGB, the DJBS (U.S. Pat. No. 7,819,836) is a fully reversible, nonsurgical procedure while still leveraging an important aspect of RYGB (eliminating nutrient exposure to the duodenum and jejunum). The clinical effects of improved glycemic control of the DJBL provide more evidence for the role of the duodenum in the interplay of obesity, metabolic syndrome, and type 2 diabetes. However, based on the rather high adverse event rate of the DJBL, this technique will not be likely adopted (5).

An additional nonsurgical avenue of investigation is ablation of the wall of one or more of the same organs of the gastrointestinal tract. Ablation could result in a similar absence of hormonal or neural signals as in bariatric surgery. Ablation of the duodenum is of particular interest given that the duodenum is recognized as a metabolic signaling center that seems to play a role in regulating insulin action and, therefore, insulin resistance (6).

One specific technique is hydrothermal ablation (U.S. Pat. No. 9,757,535) of the mucosa of the duodenum or DMR (duodenal mucosal resurfacing). The desired ablation is limited to the superficial intestinal mucosa leaving any deeper structures untouched. The goal with DMR is restoration to a normal mucosal interface in the duodenum (7). DMR has been found to be feasible and safe in that it elicited glycemic improvement in sub optimally controlled T2D patients using oral glucose-lowering medication (8). While showing promise, DMR has shown adverse events such as increased postoperative pain and usability shortcomings such as the need for fluoroscopy which could limit widespread adoption.

An additional ablative technique uses a laser to selectively target the submucosa of the duodenal wall and neural structures (nerves cells as ganglions, plexuses, axon, etc.) within. The proposed technique EGM (U.S. Pat. No. 10,575, 904) or endoscopic glycemic management targets a large portion of the duodenum as nerves of the duodenum travel throughout the submucosal layer of the duodenum. The application of a laser does address usability shortcomings of hydrothermal resurfacing of the duodenal mucosa such as the ability for direct visualization during ablation (9).

Nonsurgical implants mimicking bariatric surgery have shown some level of glycemic control yet have unacceptable levels of adverse events. Promising ablative technologies are being introduced where glycemic improvements have been demonstrated and/or more clinical Investigation needs to be demonstrated. No single treatment has been demonstrated to be endoscopic and noninvasive that could target both the mucosa and the richly innervated submucosa which both play a role in resulting changes of hormonal and neural signals that are changed in bariatric surgery while at the same time not resulting in high rates of adverse events.

The present invention is directed to overcoming these and other deficiencies in the art.

SUMMARY OF THE DISCLOSURE

The present disclosure generally relates to medical devices such as cryogenic catheter probes, cryogenic ablation systems, and methods for their use for selectively ablating of the mucosa and submucosa in the gastrointestinal tract, including, inter alia, for the treatment of Type 2 Diabetes, obesity, and other metabolic and medical conditions.

In one aspect, the present disclosure provides a cryogenic catheter probe including a chamber and a channel assembly housed within the chamber. The chamber includes a distal end, a proximal end, and a hollow body portion disposed between the distal and proximal ends. The distal end of the chamber is adapted for connection with a distal probe tip. The proximal end of the chamber is adapted for connection with a shaft. The channel assembly includes: (i) a central rail; (ii) at least one cryogenic fluid delivery channel comprising a fluid delivery channel portion and a sprayer connected to the distal end of the fluid delivery channel portion, said at least one cryogenic fluid delivery channel being mounted on the central rail for longitudinal movement along the central rail; (iii) a delivery channel guide for guiding the at least one cryogenic fluid delivery channel longitudinally along the central rail during operation of the probe; and (iv) a sprayer guide for guiding the sprayer of the at least one cryogenic fluid delivery channel longitudinally along the central rail during operation of the probe. The sprayer is configured to release cryogenic spray in at least one treatment zone along the hollow body portion of the chamber.

In another aspect, the present disclosure provides a cryogenic ablation system. The cryogenic ablation system includes a cryogenic catheter probe as disclosed herein; a catheter portion functionally connected to the cryogenic catheter probe; and a controller configured to control the functionality of the cryogenic catheter probe.

In another aspect, the present disclosure provides a method of performing cryogenic ablation of mucosal tissue and/or of both mucosal tissue and submucosal tissue in the gastrointestinal tract of a subject. This method includes the steps of: (a) providing a cryogenic ablation system as disclosed herein; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

In another aspect, the present disclosure provides a method of performing cryogenic ablation of mucosal tissue and/or of both mucosal tissue and submucosal tissue in the gastrointestinal tract of a subject. This method includes the steps of: (a) providing a cryogenic ablation system as disclosed herein; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

In another aspect, the present disclosure provides a use of a cryogenic ablation system in a method of performing cryogenic ablation of mucosal tissue and/or of both mucosal tissue and submucosal tissue in the gastrointestinal tract of a subject, where the method comprises: (a) providing a cryogenic ablation system as disclosed herein; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

In another aspect, the present disclosure provides a cryogenic ablation system for use in a method of performing cryogenic ablation of mucosal tissue and/or of both mucosal tissue and submucosal tissue in the gastrointestinal tract of a subject, where the method comprises: (a) providing a cryogenic ablation system as disclosed herein; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

In another aspect, the present disclosure provides a method for performing a medical procedure in a small intestine and/or stomach of a patient in need of the medical procedure. This method includes the steps of: (a) providing a cryogenic ablation system as disclosed herein; (b) contacting the cryogenic catheter probe of the system with a target treatment region of the small intestine and/or stomach of the patient; and (c) releasing a cryogenic fluid from the at least one sprayer to treat the target treatment region by cryogenically ablating at least a portion the mucosal tissue or ablating at least a portion of both the mucosal and submucosal tissue of the target treatment region, thereby performing a medical procedure to treat a condition of the patient selected from the group consisting of Type 1 diabetes, Type 2 diabetes, non-alcoholic fatty liver disease (NAFLD), non-alcoholic steatohepatitis (NASH), and obesity.

In another aspect, the present disclosure provides a use of a cryogenic ablation system in a method for performing a medical procedure in a small intestine and/or stomach of a patient in need of the medical procedure. This method includes the steps of: (a) providing a cryogenic ablation system as disclosed herein; (b) contacting the cryogenic catheter probe of the system with a target treatment region of the small intestine and/or stomach of the patient; and (c) releasing a cryogenic fluid from the at least one sprayer to treat the target treatment region by cryogenically ablating at least a portion the mucosal tissue or ablating at least a portion of both the mucosal and submucosal tissue of the target treatment region, thereby performing a medical procedure to treat a condition of the patient selected from the group consisting of Type 1 diabetes, Type 2 diabetes, non-alcoholic fatty liver disease (NAFLD), non-alcoholic ste-atohepatitis (NASH), and obesity.

In another aspect, the present disclosure provides a cryogenic ablation system for use in a method for performing a medical procedure in a small intestine and/or stomach of a patient in need of the medical procedure. This method includes the steps of: (a) providing a cryogenic ablation system as disclosed herein; (b) contacting the cryogenic catheter probe of the system with a target treatment region of the small intestine and/or stomach of the patient; and (c) releasing a cryogenic fluid from the at least one sprayer to treat the target treatment region by cryogenically ablating at least a portion the mucosal tissue or ablating at least a portion of both the mucosal and submucosal tissue of the target treatment region, thereby performing a medical procedure to treat a condition of the patient selected from the group consisting of Type 1 diabetes, Type 2 diabetes, non-alcoholic fatty liver disease (NAFLD), non-alcoholic ste-atohepatitis (NASH), and obesity.

In certain aspects, the present disclosure relates to a cryogenic ablation system for treating tissue of the esopha-gus, stomach, duodenum, or jejunum which comprises a catheter and controller. The catheter is delivered to the gastrointestinal tract via a delivery channel of a standard endoscope, an accessory channel mounted to the side of a standard endoscope, or inside an over a tube or delivery sheath. All three methods allow the user to position the endoscope on the distal end of the catheter facilitating visualization through the distal end of the catheter.

In certain aspects, the catheter encompasses a probe, a shaft, a handle, a high-pressure catheter connector, and a distal tip. The probe increases and decreases in diameter to conform within the gastrointestinal tract's anatomical pas-sageways (e.g., esophagus, stomach, duodenum, or jeju-num). When conformed within the passageway, the probe may be positioned at the desired location using the endo-scope's visualization.

In certain aspects, the probe contains at least one cryo-genic fluid delivery channel and the central rail. The probe's distal end is mounted to the central rail, which runs through the distal tip, and the proximal end of the probe is mounted to the shaft. The cryogenic fluid delivery channel(s) are coupled to and slide along the central rail. Both the central rail and the cryogenic fluid delivery channel(s) extend proximally through the shaft to the high-pressure catheter connector.

In certain aspects, the controller encompasses a control system, a cryogenic fluid delivery system, a cryogenic supply system, and the controller connector. The control system contains hardware, software with associated algo-rithms, and a user interface, defining treatment parameters. The cryogenic fluid delivery system encompasses one or more control valves, one or more diverter valves, one or more motors, and one or more exhaust ports, which together with the control system automatically controls and directs the flow of cryogenic fluid at a predetermined time, a predetermined flow rate, to a selected cryogenic delivery channel(s), and cryogenic delivery channel(s) position, direction, translation speed. The cryogenic supply system encompasses one or more canisters that supply the cryogenic fluid for treatment. Once the high-pressure catheter connec-tor is coupled to the controller connector, one or more cryogenic fluid delivery channels are fluidly coupled to the one or more canisters of cryogenic fluid.

In certain aspects, upon release from the controller and through one or more cryogenic fluid delivery channel(s), cryogenic fluid is directed outwardly toward the probe inner surface, causing the probe diameter to increase and come into intimate contact with the tissue of the gastrointestinal tract. The cryogenic ablation system is now ready for treatment. Based on the controller's control system, the present invention accurately controls probe inflation rate, allowing the probe to increase diameter for intimate contact with gastrointestinal tissue, probe inflation pressure, and probe temperature.

In certain aspects, upon delivery of the cryogenic fluid during treatment, liquid cryogen makes contact with the inside of the probe wall causing cells in close proximity to the ablation interface (the interface of the probe wall and the contacted tissue or the inner layer of the mucosa) to undergo rapid freezing rates, whereas cells in the periphery of the ablation interface (submucosa and deeper layers of the wall of the small intestine) between the probe and the mucosa in intimate contact undergo moderate to lower freezing rates (10).

In certain aspects, the application of liquid cryogen through the introduction into an expandable probe in inti-mate contact with the tissue of the gastrointestinal tract (mucosa) specifically of the small intestine leads to regen-erated small intestine tissue. The effect is from the mucosa and into the submucosa where critical microvasculature in the submucosa is preserved (11). Temperature decrease to the submucosa facilitates modulation of the nerves of the submucosa (partial or reversible ablation, blocking, stimu-lation) while leaving critical microvascular structures intact which are necessary for regeneration. Further, the rapid freezing rates delivered to mucosal tissue modifies integrity and function of the intestinal barrier (mucosal epithelium) wherein the target mucosa intercellular spaces (ICS) decrease, and MI (mucosal impedance) increase thereby decreasing the permeability in mucosa ablated (12, 13).

In contrast to radiofrequency ablation, laser ablation, heated fluid ablation, and potentially other heat-based abla-tion techniques, cryoablation results in a robust inflamma-tory response, particularly in the submucosa. The inflam-matory response creates the potential to stimulate additional responses particularly immunologic responses in cryoabla-tion of tumors (14). Commonly employed ablation therapies in the clinical setting are radiofrequency ablation (RFA), microwave ablation, high-intensity focused ultrasound, and cryoablation. All these treatments operate on the principle of hyperthermia except for cryoablation, which is a hypother-mic modality that induces tissue damage by a freeze-thaw process. Of all the ablation techniques, cryoablation dem-onstrated the highest potential to elicit a post-ablative immu-nogenic response (15). Finally, peptide bonds are not dis-rupted in the process of cryoablation so cold denaturation of proteins can be reversible with warming and rehydration (16).

Various aspects of the present disclosure are also addressed by the following Paragraphs 1-39 and in the noted combinations thereof, as follows:

Paragraph 1: A cryogenic catheter probe comprising: a chamber comprising a distal end, a proximal end, and a hollow body portion disposed between the distal and proxi-mal ends, wherein said distal end is adapted for connection with a distal probe tip, and wherein said proximal end is adapted for connection with a shaft; and a channel assembly housed within the chamber, said channel assembly compris-ing: (i) a central rail; (ii) at least one cryogenic fluid delivery channel comprising a fluid delivery channel portion and a sprayer connected to the distal end of the fluid delivery channel portion, said at least one cryogenic fluid delivery channel being mounted on the central rail for longitudinal movement along the central rail; (iii) a delivery channel guide for guiding the at least one cryogenic fluid delivery channel longitudinally along the central rail during operation of the probe; and (iv) a sprayer guide for guiding the sprayer of the at least one cryogenic fluid delivery channel longitudinally along the central rail during operation of the probe, wherein said sprayer is configured to release cryogenic spray in at least one treatment zone along the hollow body portion of the chamber.

Paragraph 2: The probe according to Paragraph 1, further comprising a distal probe tip attached to the distal end of the probe.

Paragraph 3: The probe according to Paragraph 1, wherein the delivery channel guide comprises a central opening configured to fit around the central rail and an exterior or interior groove of the at least one cryogenic fluid delivery channel to be guided thereby.

Paragraph 4: The probe according to Paragraph 1, wherein the sprayer guide comprises a central opening configured to fit around the central rail and an exterior or interior groove for the sprayer of at least one cryogenic fluid delivery channel to be guided thereby.

Paragraph 5: The probe according to Paragraph 4, wherein the central opening of the sprayer guide is configured so that it prevents rotation of the sprayer guide around the central opening.

Paragraph 6: The probe according to Paragraph 1, wherein the channel assembly comprises 1 to 20 cryogenic fluid delivery channels.

Paragraph 7: The probe according to Paragraph 1, wherein the channel assembly comprises a number of cryogenic fluid delivery channels selected from the group consisting of 1, 2, 3, 4, 5, 6, 7, and 8 cryogenic fluid delivery channels.

Paragraph 8: The probe according to Paragraph 1, wherein the number of interior or exterior grooves of the corresponding delivery channel guide and sprayer guide are the same as the number of delivery channels.

Paragraph 9: The probe according to Paragraph 1, wherein the sprayers of each of the cryogenic fluid delivery channels are configured to release cryogenic spray either in unison or independently of one another.

Paragraph 10: The probe according to Paragraph 1, wherein each sprayer is configured to release cryogenic spray in a different treatment zone along the probe.

Paragraph 11: The probe according to Paragraph 1, wherein said catheter is configured for selective ablation in the mucosa and submucosa of a gastrointestinal tract of a subject.

Paragraph 12: The probe according to Paragraph 1, wherein the cryogenic fluid delivery channels are independently controlled and turned to an on or off position.

Paragraph 13: The probe according to Paragraph 1, wherein the treatment tissue comprises mucosal and/or submucosal tissue of the large intestine, small intestine, stomach, esophagus, rectum, and anus.

Paragraph 14: A cryogenic ablation system comprising: a cryogenic catheter probe according to any one of Paragraphs 1-13; a catheter portion functionally connected to the probe; and a controller configured to control the functionality of the cryogenic catheter probe.

Paragraph 15: The system according to Paragraph 14, wherein the system further comprises a shaft connected to the proximal end of the probe and/or running through all or a portion of the probe.

Paragraph 16: The system according to Paragraph 15, wherein the shaft is connected to a handle.

Paragraph 17: The system according to Paragraph 16, wherein the handle further comprises a high pressure plate.

Paragraph 18: The system according to Paragraph 16, wherein the handle further comprises a hub-cap connected to the high pressure plate.

Paragraph 19: The system according to Paragraph 15, wherein the system further comprises a pressure detection tube disposed within the cryogenic catheter probe or shaft.

Paragraph 20: The system according to Paragraph 14, wherein said sprayer is connected to the outside of the distal end of the cryogenic fluid delivery channel.

Paragraph 21: The system according to Paragraph 14, wherein each cryogenic fluid delivery channel is fluidly connected to a delivery channel control valve and a reservoir of cryogenic fluid whereby cryogenic fluid delivery channel can be controlled by actuation of each delivery channel control valve.

Paragraph 22: The system according to Paragraph 14, wherein each cryogenic fluid delivery channel has a sprayer which allows for partial restriction of cryogenic liquid and a delivery channel control valve controls release of cryogenic fluid from the cryogenic supply block into each cryogenic fluid delivery channel.

Paragraph 23: The system according to Paragraph 14, wherein the sprayers may be positioned axially over a fixed and keyed central rail.

Paragraph 24: The system according to Paragraph 14, wherein the cryogenic catheter probe is placed into an expanded state upon release of cryogenic fluid into the inside of the cryogenic catheter probe.

Paragraph 25: The system according to Paragraph 14, wherein the controller independently controls deliver of cryogenic fluid to each delivery channel via control valves at the proximal end of each delivery channel, and/or wherein a reservoir system allows for large ablation areas up to 10 cm and beyond of tissue in a partial-circumferential or full-circumferential ablations.

Paragraph 26: The system according to Paragraph 25, wherein the controller comprises one or more variable controller parameters used to control the functional assembly.

Paragraph 27: The system according to Paragraph 25, wherein the system further comprises at least one sensor constructed and arranged to produce a sensor signal.

Paragraph 28: The system according to Paragraph 25, wherein the controller is configured to perform closed-loop energy delivery to the functional assembly based on the sensor signal.

Paragraph 29: A method of performing cryogenic ablation of mucosal tissue and/or of both mucosal tissue and submucosal tissue in the gastrointestinal tract of a subject, said method comprising: (a) providing a cryogenic ablation system according to any one of Paragraphs 14-28; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

Paragraph 30: The method according to Paragraph 29, wherein the target treatment region comprises mucosal tissue and/or both mucosal and submucosal tissue of the large intestine, small intestine, stomach, esophagus, rectum, or anus of the subject.

Paragraph 31: The method according to Paragraph 30, wherein treating the target treatment region comprises performing a series of tissue ablation steps, each comprising ablation of an axial length of the large intestine, small intestine, stomach, esophagus, rectum, or anus of the subject, wherein each ablation step is optionally preceded by a tissue expansion step.

Paragraph 32: The method according to Paragraph 29, further comprises adjusting at least one variable controller parameter based on the sensor signal.

Paragraph 33: Use of a cryogenic ablation system in a method of performing cryogenic ablation of mucosal tissue and/or of both mucosal tissue and submucosal tissue in the gastrointestinal tract of a subject, wherein said method comprises: (a) providing a cryogenic ablation system according to any one of Paragraphs 14-28; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

Paragraph 34: A cryogenic ablation system for use in a method of performing cryogenic ablation of mucosal tissue and/or of both mucosal tissue and submucosal tissue in the gastrointestinal tract of a subject, wherein said method comprises: (a) providing a cryogenic ablation system according to any one of Paragraphs 14-28; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

Paragraph 35: A method for performing a medical procedure in a small intestine and/or stomach of a patient in need of said medical procedure, the method comprising: (a) providing a cryogenic ablation system according to any one of Paragraphs 14-28; (b) contacting the cryogenic catheter probe of the system with a target treatment region of the small intestine and/or stomach of the patient; and (c) releasing a cryogenic fluid from the at least one sprayer to treat the target treatment region by cryogenically ablating at least a portion the mucosal tissue or ablating at least a portion of both the mucosal and submucosal tissue of the target treatment region, thereby performing a medical procedure to treat a condition of the patient selected from the group consisting of Type 1 diabetes, Type 2 diabetes, non-alcoholic fatty liver disease (NAFLD), non-alcoholic steatohepatitis (NASH), and obesity.

Paragraph 36: The method according to Paragraph 35, wherein treating the target treatment region comprises performing a series of tissue ablation steps, each comprising ablation of an axial length of the small intestine or stomach tissue, wherein each ablation step is optionally preceded by a tissue expansion step.

Paragraph 37: The method according to Paragraph 35, further comprises adjusting at least one variable controller parameter based on the sensor signal.

Paragraph 38: Use of a cryogenic ablation system in a method for performing a medical procedure in a small intestine and/or stomach of a patient in need of said medical procedure, the method comprising: (a) providing a cryogenic ablation system according to any one of Paragraphs 14-28; (b) contacting the cryogenic catheter probe of the system with a target treatment region of the small intestine and/or stomach of the patient; and (c) releasing a cryogenic fluid from the at least one sprayer to treat the target treatment region by cryogenically ablating at least a portion the mucosal tissue or ablating at least a portion of both the mucosal and submucosal tissue of the target treatment region, thereby performing a medical procedure to treat a condition of the patient selected from the group consisting of Type 1 diabetes, Type 2 diabetes, non-alcoholic fatty liver disease (NAFLD), non-alcoholic steatohepatitis (NASH), and obesity.

Paragraph 39: A cryogenic ablation system for use in a method for performing a medical procedure in a small intestine and/or stomach of a patient in need of said medical procedure, the method comprising: (a) providing a cryogenic ablation system according to any one of Paragraphs 14-28; (b) contacting the cryogenic catheter probe of the system with a target treatment region of the small intestine and/or stomach of the patient; and (c) releasing a cryogenic fluid from the at least one sprayer to treat the target treatment region by cryogenically ablating at least a portion the mucosal tissue or ablating at least a portion of both the mucosal and submucosal tissue of the target treatment region, thereby performing a medical procedure to treat a condition of the patient selected from the group consisting of Type 1 diabetes, Type 2 diabetes, non-alcoholic fatty liver disease (NAFLD), non-alcoholic steatohepatitis (NASH), and obesity.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, if provided, like reference numerals contained in the drawings are meant to identify similar or identical elements.

FIG. 23 is a side view of the controller and catheter locking mechanism.

FIG. 24 is a side view of the steps of the controller and catheter locking mechanism.

Figure 1:
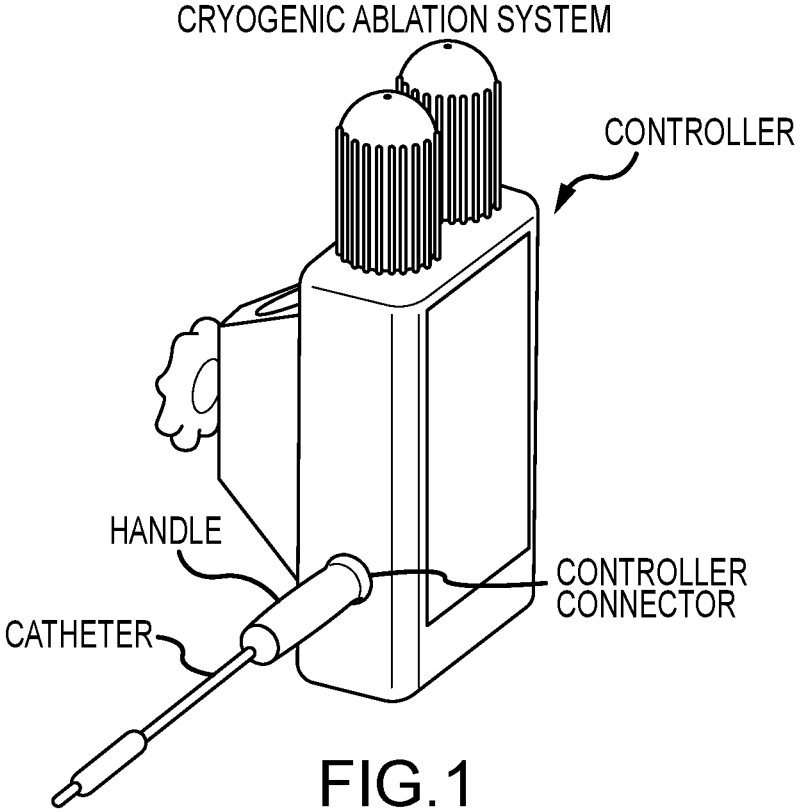
FIG. 1 is a perspective view of the cryogenic ablation system and portions of the catheter and controller.

It should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION OF THE DISCLOSURE

The present disclosure relates to methods, devices, and systems including a cryogenic catheter probe, a cryogenic ablation system (e.g., including a cryogenic catheter probe and a controller) for the treatment of metabolic conditions including, but not limited to, Type 2 diabetes, obesity, hypertension, non-alcoholic fatty liver disease, acid reflux, Barrett's esophagus, etc., through efficiently ablating the luminal layers of the gastrointestinal tissue, including, for example, the esophagus, stomach, pylorus, duodenum, jejunum, etc. Structures affected by the various devices, systems, and methods of the present disclosure include the mucosa, submucosa, and/or muscularis layers. Other structures within the layers that may also be affected by the devices, systems, and methods of the present disclosure include, without limitation, vasculature and/or nerve tissue. For the devices, systems, and methods of the present disclosure, application of cryogen fluid through the introduction into a probe (including, without limitation, an expandable probe) in intimate contact with the mucosa of tissues such as the small intestine, stomach, and/or the esophagus leads to remodeling of the intestinal tissue. The effect is from the mucosa and into the submucosa where critical microvasculature in the submucosa is preserved.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements but is not limited to possessing only those one or more elements. Likewise, an element of a system, device, or apparatus that "comprises," "has," "includes" or "contains" one or more features possesses those one or more features but is not limited to possessing only those one or more features. Likewise, an element of a system, device, or apparatus that "comprises," "has," "includes," or "contains" one or more features possesses those one or more elements but is not limited to keeping only those one or more attributes.

The terms "proximal" and "distal" are used herein regarding a clinician manipulating the controller portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those of ordinary skill in the art will recognize various equivalent variations on the description that follows. Unless otherwise stated, in this application, specified relationships, such as parallel to, aligned with, or in the same plane as, mean that the specified relationships are within limitations of manufacturing processes and manufacturing variations. When components are described as being coupled, connected, being in contact, or contacting one another, they need not be physically directly touching one another unless specifically described as such. Like elements in various embodiments are commonly referred to with like reference numerals.

Table A is a listing of the reference numbers for the various elements or items shown in the as-filed Figures.

TABLE A

| Ref. No. | Element/Item | Figures |
|---|---|---|
| 1 | Cryogenic Ablation System | 1 |
| 2 | Controller | 1, 3, 4, 8A, 9, 23 |
| 3 | Handle | 1 |
| 4 | Catheter (Cryogenic Catheter) | 1, 23 |
| 5 | Controller Connector | 1, 8A, 9 |
| 6 | Endoscope | 2 |
| 7 | Duodenum | 2 |
| 8 | Stomach | 2 |
| 9 | Cryogenic Catheter (Agil's Cryoablation) | 2 |
| 10 | Load Cap | 3, 4, 8A, 9 |
| 11 | Front Panel | 3, 8A |
| 12 | Display | 3, 8A |
| 13 | Mounting Block | 4, 8A |
| 14 | Pole Insertion Hole | 4 |
| 15 | Mounting Wheel | 4, 8A |
| 16 | Block Body | 4, 8A |
| 17 | Catheter (Cryogenic Catheter Probe) | 5-7, 10A |
| 18 | Distal Probe Tip | 5-7, 10A, 11, 12, 13 |
| 19 | Cryogenic (Fluid) Delivery Channel Assembly | 5-7, 10A, 10B, 11, 12, 13, 14A, 14D, 15A, 15B, 16, 18, 19 |
| 20 | Probe (Chamber) | 5-7, 10A, 11, 12, 13 |
| 21 | Central Rail | 5-7, 10A, 10B, 11, 12, 13, 14A, 14D, 15A, 15B, 16, 17A, 17B, 17C, 17D, 18, 19, 20, 21 |
| 22 | Shaft | 5-7, 10A, 11, 12, 13, 14A, 15A, 19, 20, 21 |
| 23 | Handle | 5-7 |
| 24 | High Pressure Plate | 5-7 |
| 25 | Hub Cap | 5-7 |
| 26 | Load Cap | 5 |
| 27 | Cryogenic Supply System | 8A, 9 |
| 28 | Cryogenic Fluid Delivery System | 8A, 9 |
| 29 | Control System | 8A |
| 30 | Motherboard (backside of display) | 8A |
| 31 | Cartridge Container | 9 |
| 32 | Cryogenic Supply Block | 9 |
| 33 | Main Flow Valve | 9 |
| 34 | Delivery Channel Flow Valve | 9 |
| 35 | Catheter Locking Motor | 9 |
| 36 | Treatment Motor | 9 |
| 37 | High Pressure Connector | 9 |
| 38 | Treatment Slide | 9 |
| 39 | Exhaust Chamber | 9 |
| 40 | Flow/Pressure PCBA | 9 |
| 41 | Exhaust Valve | 9 |
| 42 | Sprayer | 10A, 10B, 14A, 14B, 14C, 14D, 15A, 15B, 16, 18, 19 |
| 43 | Delivery Channel Guide | 10A, 10B, 11, 12, 16, 18, 19, 21 |
| 44 | Delivery Channel (Cryogenic Fluid Delivery Channel) | 10A, 10B, 11, 12, 14A, 14D, 15A, 15B, 16, 18, 19, 21 |
| 45 | Probe Inner Surface | 10A, 14A, 14B, 14C, 15A |
| 46 | Sprayer Guide | 10B, 14A, 14D, 15A, 15B, 16, 18, 19 |
| 47 | Quad-Core Design | 14A, 14B, 14C, 14D |
| 48 | Probe Wall | 14A, 14B, 14C, 15A |

TABLE A-continued

| Ref. No. | Element/Item | Figures |
|---|---|---|
| 49 | Pressure Detection Tube | 14A, 15A, 20, 21 |
| 50 | Treatment Zone | 14B, 14C |
| 51 | Cryogenic Fluid (Cryogenic Liquid) | 14B, 14C, 14D, 15A |
| 52 | Tri-Core Design | 15A, 15B, 16 |
| 53 | Shaft Wall | 20, 21 |
| 54 | Delivery Channel Port | 20 |
| 55 | Shaft Inner Space | 21 |
| 56 | High-Pressure Catheter Connector | 22 |
| 57 | High-Pressure Catheter Connector Cap | 22 |
| 58 | Hub Cap (of High-Pressure Catheter Connector) | 22 |
| 59 | Locking Sleeve | 22, 23, 24 |
| 60 | High Pressure Plate | 22 |
| 61 | O-Rings | 22 |
| 62 | Threaded Shafts | 22 |
| 63 | Contouring Hub | 22 |
| 64 | Locking Pins | 22 |
| 65 | Contouring Core | 22 |
| 66 | Alignment Pins | 22 |
| 67 | Delivery Channels (of High-Pressure Catheter Connector) | 22 |
| 68 | Guiding Hub | 22 |
| 69 | Guiding Sleeve | 22 |
| 70 | Lock Receiver | 23, 24 |
| 71 | Ramp | 23, 24 |
| 72 | Curved Channel | 23, 24 |
| 73 | Recess | 23, 24 |
| 74 | Locking Sleeve Tab | 23, 24 |
| 75 | Locking Sleeve Screw | 23 |

In one aspect, the present disclosure provides a cryogenic catheter probe including a chamber and a channel assembly housed within the chamber. The chamber includes a distal end, a proximal end, and a hollow body portion disposed between the distal and proximal ends. The distal end of the chamber is adapted for connection with a distal probe tip. The proximal end of the chamber is adapted for connection with a shaft. The channel assembly includes: (i) a central rail; (ii) at least one cryogenic fluid delivery channel comprising a fluid delivery channel portion and a sprayer connected to the distal end of the fluid delivery channel portion, said at least one cryogenic fluid delivery channel being mounted on the central rail for longitudinal movement along the central rail; (iii) a delivery channel guide for guiding the at least one cryogenic fluid delivery channel longitudinally along the central rail during operation of the probe; and (iv) a sprayer guide for guiding the sprayer of the at least one cryogenic fluid delivery channel longitudinally along the central rail during operation of the probe. The sprayer is configured to release cryogenic spray in at least one treatment zone along the hollow body portion of the chamber.

In one embodiment, a distal probe tip attached to the distal end of the probe.

In one embodiment, the delivery channel guide comprises a central opening configured to fit around the central rail and an exterior or interior groove of the at least one cryogenic fluid delivery channel to be guided thereby.

In one embodiment, the sprayer guide comprises a central opening configured to fit around the central rail and an exterior or interior groove for the sprayer of at least one cryogenic fluid delivery channel to be guided thereby.

In one embodiment, the central opening of the sprayer guide is configured so that it prevents rotation of the sprayer guide around the central opening.

In one embodiment, the channel assembly comprises 1 to 20 cryogenic fluid delivery channels.

In one embodiment, the channel assembly comprises a number of cryogenic fluid delivery channels selected from the group consisting of 1, 2, 3, 4, 5, 6, 7, and 8 cryogenic fluid delivery channels.

In one embodiment, the number of interior or exterior grooves of the corresponding delivery channel guide and sprayer guide are the same as the number of delivery channels.

In one embodiment, the sprayers of each of the cryogenic fluid delivery channels are configured to release cryogenic spray either in unison or independently of one another.

In one embodiment, each sprayer is configured to release cryogenic spray in a different treatment zone along the probe.

In one embodiment, the catheter is configured for selective ablation in the mucosa and submucosa of a gastrointestinal tract of a subject.

In one embodiment, the cryogenic fluid delivery channels are independently controlled and turned to an on or off position.

In one embodiment, the treatment tissue comprises mucosal and/or submucosal tissue of the large intestine, small intestine, stomach, esophagus, rectum, and anus.

In another aspect, the present disclosure provides a cryogenic ablation system. The cryogenic ablation system includes a cryogenic catheter probe as disclosed herein; a catheter portion functionally connected to the cryogenic catheter probe; and a controller configured to control the functionality of the cryogenic catheter probe.

In one embodiment, the system further comprises a shaft connected to the proximal end of the probe and/or running through all or a portion of the probe.

In one embodiment, the shaft is connected to a handle.

In one embodiment, the handle further comprises a high pressure plate.

In one embodiment, the handle further comprises a hub-cap connected to the high pressure plate.

In one embodiment, the system further comprises a pressure detection tube disposed within the cryogenic catheter probe or shaft.

In one embodiment, the sprayer is connected to the outside of the distal end of the cryogenic fluid delivery channel.

In one embodiment, each cryogenic fluid delivery channel is fluidly connected to a delivery channel control valve and a reservoir of cryogenic fluid whereby cryogenic fluid delivery channel can be controlled by actuation of each delivery channel control valve. As used herein, the term "control valve" may also be referred to as a "flow valve" and the like.

In one embodiment, each cryogenic fluid delivery channel has a sprayer which allows for partial restriction of cryogenic liquid and a delivery channel control valve controls release of cryogenic fluid from the cryogenic supply block into each cryogenic fluid delivery channel.

In one embodiment, the sprayers may be positioned axially over a fixed and keyed central rail.

In one embodiment, the cryogenic catheter probe is placed into an expanded state upon release of cryogenic fluid into the inside of the cryogenic catheter probe.

In one embodiment, the controller independently controls deliver of cryogenic fluid to each delivery channel via control valves at the proximal end of each delivery channel, and/or wherein a reservoir system allows for large ablation areas up to 10 cm and beyond of tissue in a partial-circumferential or full-circumferential ablations.

In one embodiment, the controller comprises one or more variable controller parameters used to control the functional assembly.

In one embodiment, the system further comprises at least one sensor constructed and arranged to produce a sensor signal.

In one embodiment, the controller is configured to perform closed-loop energy delivery to the functional assembly based on the sensor signal.

In another aspect, the present disclosure provides a method of performing cryogenic ablation of mucosal tissue and/or of both mucosal tissue and submucosal tissue in the gastrointestinal tract of a subject. This method includes the steps of: (a) providing a cryogenic ablation system as disclosed herein; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

In one embodiment, the target treatment region comprises mucosal tissue and/or both mucosal and submucosal tissue of the large intestine, small intestine, stomach, esophagus, rectum, or anus of the subject.

In one embodiment, treating the target treatment region comprises performing a series of tissue ablation steps, each comprising ablation of an axial length of the large intestine, small intestine, stomach, esophagus, rectum, or anus of the subject, wherein each ablation step is optionally preceded by a tissue expansion step.

In one embodiment, the method further comprises adjusting at least one variable controller parameter based on the sensor signal.

In another aspect, the present disclosure provides a use of a cryogenic ablation system in a method of performing cryogenic ablation of mucosal tissue and/or of both mucosal tissue and submucosal tissue in the gastrointestinal tract of a subject, where the method comprises: (a) providing a cryogenic ablation system as disclosed herein; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

In another aspect, the present disclosure provides a cryogenic ablation system for use in a method of performing cryogenic ablation of mucosal tissue and/or of both mucosal tissue and submucosal tissue in the gastrointestinal tract of a subject, where the method comprises: (a) providing a cryogenic ablation system as disclosed herein; (b) contacting the cryogenic catheter probe of the system with a target treatment region of the gastrointestinal tract of the subject; and (c) releasing a cryogenic fluid from the at least one sprayer to treat the target treatment region by cryogenically ablating at least a portion the mucosal tissue or ablating at least a portion of both the mucosal and submucosal tissue of the target treatment region.

In another aspect, the present disclosure provides a method for performing a medical procedure in a small intestine and/or stomach of a patient in need of the medical procedure. This method includes the steps of: (a) providing a cryogenic ablation system as disclosed herein; (b) contacting the cryogenic catheter probe of the system with a target treatment region of the small intestine and/or stomach of the patient; and (c) releasing a cryogenic fluid from the at least one sprayer to treat the target treatment region by cryogenically ablating at least a portion the mucosal tissue or ablating at least a portion of both the mucosal and submucosal tissue of the target treatment region, thereby performing a medical procedure to treat a condition of the patient selected from the group consisting of Type 1 diabetes, Type 2 diabetes, non-alcoholic fatty liver disease (NAFLD), non-alcoholic steatohepatitis (NASH), and obesity.

In one embodiment, treating the target treatment region comprises performing a series of tissue ablation steps, each comprising ablation of an axial length of the small intestine or stomach tissue, where each ablation step is optionally preceded by a tissue expansion step.

In one embodiment, the method further comprises adjusting at least one variable controller parameter based on the sensor signal.

In another aspect, the present disclosure provides a use of a cryogenic ablation system in a method for performing a medical procedure in a small intestine and/or stomach of a patient in need of the medical procedure. This method includes the steps of: (a) providing a cryogenic ablation system as disclosed herein; (b) contacting the cryogenic catheter probe of the system with a target treatment region of the small intestine and/or stomach of the patient; and (c) releasing a cryogenic fluid from the at least one sprayer to treat the target treatment region by cryogenically ablating at least a portion the mucosal tissue or ablating at least a portion of both the mucosal and submucosal tissue of the target treatment region, thereby performing a medical procedure to treat a condition of the patient selected from the group consisting of Type 1 diabetes, Type 2 diabetes, non-alcoholic fatty liver disease (NAFLD), non-alcoholic steatohepatitis (NASH), and obesity.

In another aspect, the present disclosure provides a cryogenic ablation system for use in a method for performing a medical procedure in a small intestine and/or stomach of a patient in need of the medical procedure. This method includes the steps of: (a) providing a cryogenic ablation system as disclosed herein; (b) contacting the cryogenic catheter probe of the system with a target treatment region of the small intestine and/or stomach of the patient; and (c) releasing a cryogenic fluid from the at least one sprayer to treat the target treatment region by cryogenically ablating at least a portion the mucosal tissue or ablating at least a portion of both the mucosal and submucosal tissue of the target treatment region, thereby performing a medical procedure to treat a condition of the patient selected from the group consisting of Type 1 diabetes, Type 2 diabetes, non-alcoholic fatty liver disease (NAFLD), non-alcoholic steatohepatitis (NASH), and obesity.

In another aspect, the present disclosure provides a method for performing a medical procedure in an intestine of a patient, the method comprising: (a) providing a catheter as disclosed and/or contemplated herein for insertion into the intestine or a system comprising the catheter and a controller, said catheter comprising: (i) proximal and distal portions; (ii) a probe mounted to the distal portion; and (iii) one or more cryogenic liquid delivery channels delivering cryogen to the inside of the probe; (b) introducing the catheter into the patient; and (c) treating target tissue with the probe in contact with the target tissue, wherein the target tissue comprises mucosal (and/or submucosal) tissue of the small intestine and treatment comprises ablating at least a portion of the mucosal and submucosal tissue of the small intestine, and wherein the medical procedure is configured to treat at least one of type 2 diabetes, non-alcoholic fatty liver disease (NAFLD) or non-alcoholic steatohepatitis (NASH). Suitable aspects of the present disclosure can be used in accordance with the disclosure of U.S. Pat. No. 10,610,663.

In another aspect, the present disclosure provides a method for ablating (regenerating) the mucosa of the small intestine and alter, stimulate, or reduce neural activity in the submucosa of the small intestine of a subject, the method comprising: (a) providing a catheter for insertion into the intestine or a system comprising the catheter and a controller, said catheter comprising: (i) proximal and distal portions; (ii) a probe mounted to the distal portion; and (iii) one or more cryogenic fluid delivery channels delivering cryogen to the wall of the small intestine, at a selected power density (W/cm$^2$), wherein the cryogenic fluid delivery channel can delivery cryogen that can elevate (or lower) tissue temperature from −25 C to −190 C; and (b) lowering a temperature of the target area using the cryogenic fluid delivery channels of the catheter, thereby ablating the mucosa of the intestine and delivers therapeutic energy to the submucosa to at least partially alter, stimulate, or reduce the neural activity or within the submucosal layer while maintaining functional activity of other layers of the surrounding target area. Suitable aspects of the present disclosure can be used in accordance with the disclosure of U.S. Pat. No. 10,537,387.

In certain embodiments, the medical procedure is further configured to treat a disease or disorder selected from the group consisting of: Type 2 diabetes; Type 1 diabetes; "Double diabetes"; gestational diabetes; hyperglycemia; pre-diabetes; impaired glucose tolerance; insulin resistance; and combinations thereof. Suitable aspects of the present disclosure can be used in accordance with the disclosure of U.S. Pat. No. 10,610,663.

In certain embodiments, treating target tissue modifies at least one of (1) nutrient absorption by the target tissue, (2)

hormonal signaling from the target tissue, (3) secretions of the target tissue. Suitable aspects of the present disclosure can be used in accordance with the disclosure of U.S. Pat. No. 10,610,663.

In certain embodiments, treating target tissue modifies integrity and function of the intestinal barrier (mucosal epithelium) wherein the target mucosa intercellular spaces (ICS) decrease, and MI (mucosal impedance) increase thereby decreasing the permeability in mucosa ablated.

In certain embodiments, the sensory nerves comprise at least one nerve that is activated by food passing through the duodenum; and/or wherein the sensory nerves comprise at least one nerve that transmits signals from at least one of mechano-sensors or chemoreceptors located within the duodenal wall. Suitable aspects of the present disclosure can be used in accordance with the disclosure of U.S. Pat. No. 10,537,387.

Referring now to FIG. 1, a schematic view of the cryogenic ablation system, consisting of a controller and a catheter. The catheter shown in FIG. 1 includes a catheter constructed according to the present invention's teachings and has a distal end and a proximal end. The proximal end of the catheter carries a connecting member (catheter high-pressure connector), through which the catheter is securely received into the controller. The catheter may be for a single use, whereas the controller is reusable. The catheter is shown in the attached configuration with the controller.

Figure 2:
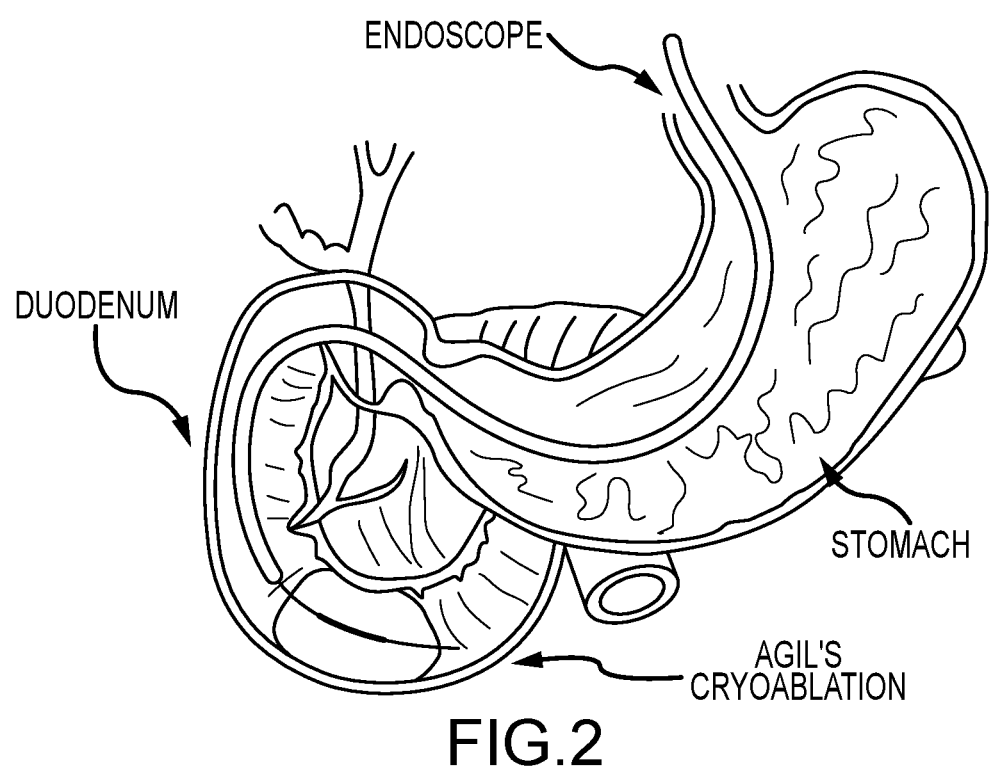
FIG. 2 is illustrative of the catheter exiting the endoscope within the duodenum positioned for treatment.

Referring now to FIG. 2, an illustration of the embodiment of a cryogenic ablation system for performing a medical procedure on a patient. The cryogenic ablation system comprises a catheter and a controller. In this illustration, an embodiment of the catheter includes a probe which is a component of the catheter and is positioned and expanded for intimate contact with the targeted tissue as illustrated. The catheter is used in conjunction with an endoscope as illustrated. The distal end of such an endoscope in FIG. 2, has an imaging camera lens and illuminating light. The image is picked up by the lens is transferred via fiber optics to a monitoring camera, which sends TV signals via a cable to a conventional monitor, where the procedure can be visualized. By virtue of this visualization, the physician can perform cryoablation in the gastrointestinal tract. The catheter can be configured to be passed through the working channel of an endoscope. The probe is positioned on a distal portion of the catheter and is configured to be inflated by introducing cryogenic fluid into the catheter where the diameter of the probe may be increased or decreased to facilitate the introduction, removal, or positioning of the catheter and treatment using the catheter within the anatomical passageways.

Figure 3:
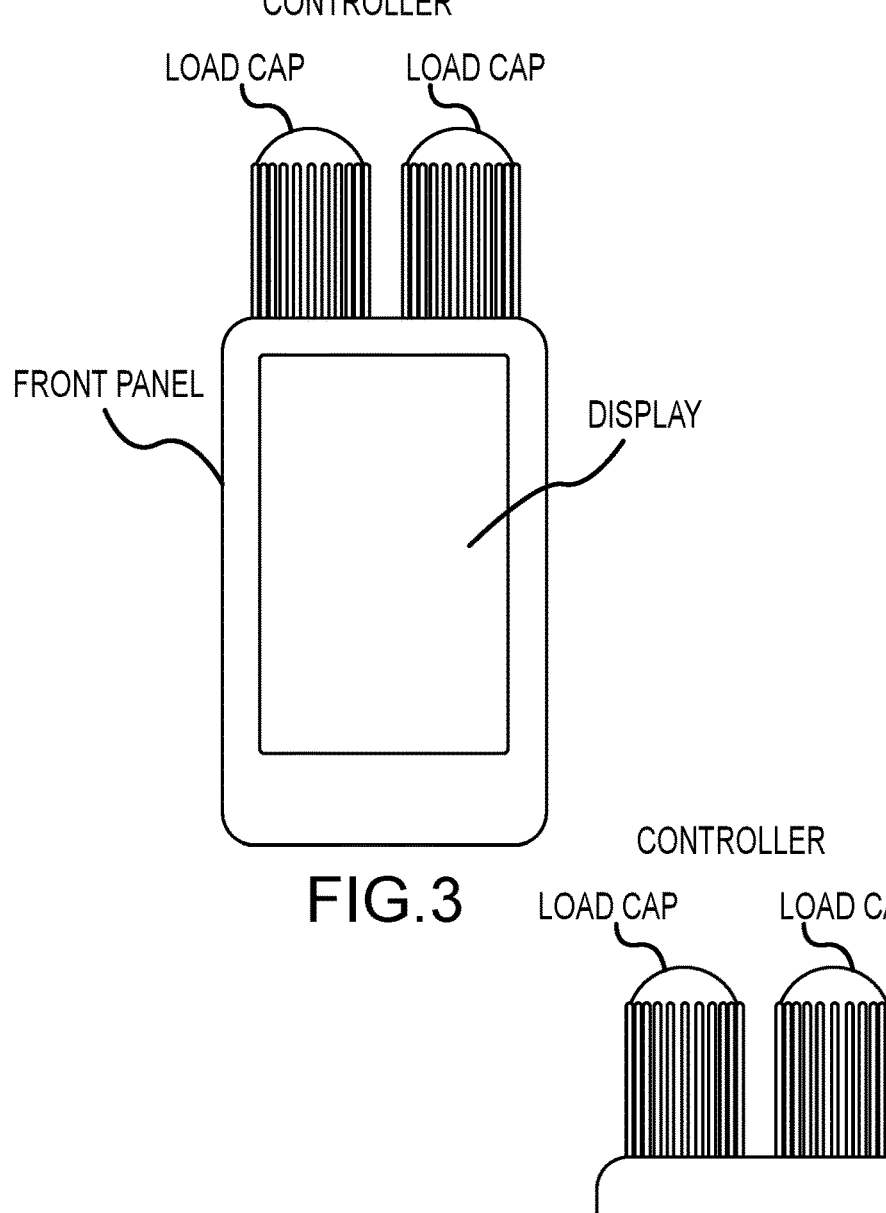
FIG. 3 is a front view of the controller with load cap(s), front panel, and display.

Referring to FIG. 3, which is a front view of the controller, comprises a display, load caps, and front panel. The display provides visual updates of the procedural, treatment, and informational status in real-time and allows user input and control while specifying details of the treatment. The controller may be configured with one or more cartridges that contain cryogenic fluid to accommodate different catheter configurations. The user will insert the canisters into the controller by unscrewing the load caps, inserting the cartridges into the controller, and tightening of load caps securely in place.

Figure 4:
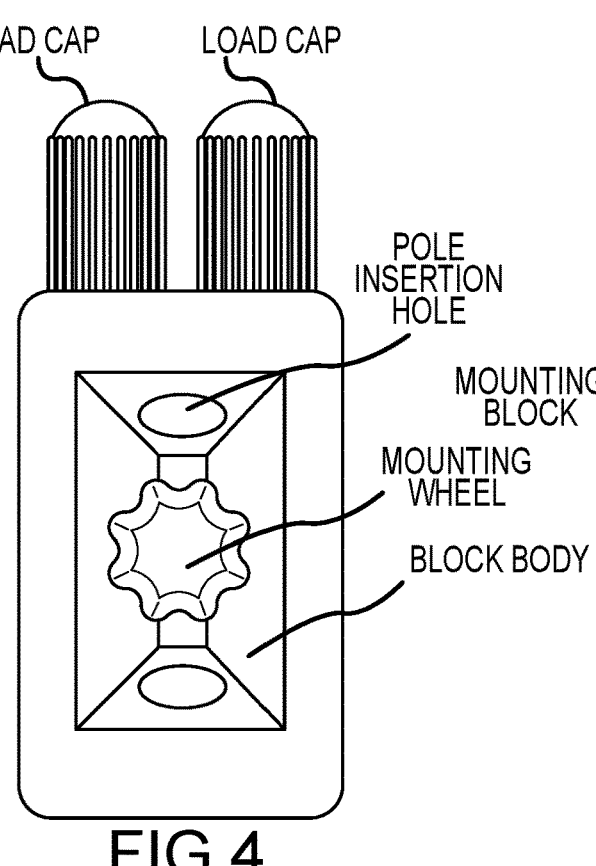
FIG. 4 is a back view of the controller and the mounting block.

Referring now to FIG. 4 which is a back view of the controller, comprising load caps, mounting block, and the case. The mounting block includes pole insertion hole, block body, and mounting wheel. The controller has the means to be securely mounted to a pole such as an IV pole or other standard equipment stand. The user slides the rod into the pole insertion holes. Once at the appropriate position, the user tightens the mounting wheel to secure the controller in place.

Figure 5:
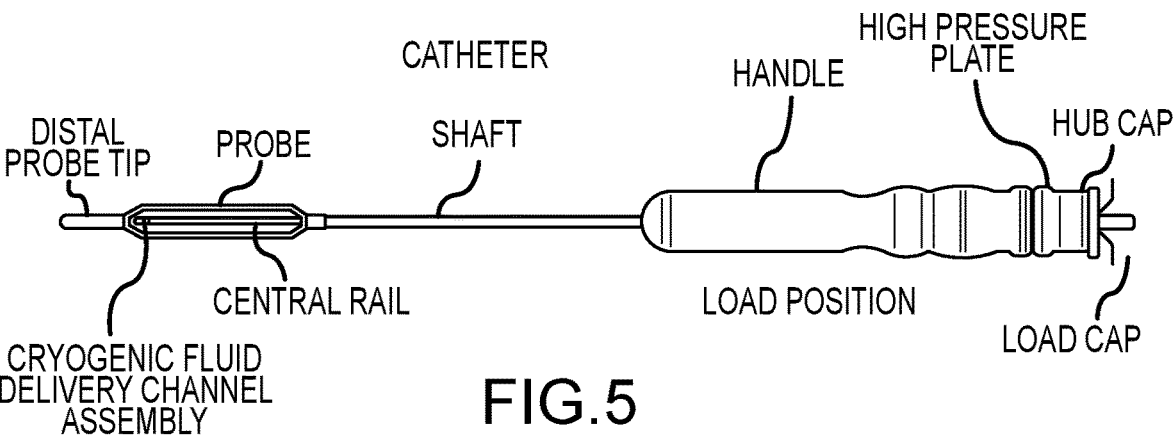
FIG. 5 is a side view of the catheter in the load position. The controller omitted for clarity with the probe sectioned to illustrate the cryogenic fluid delivery channel assembly position. The high-pressure catheter connector cap which facilitates the catheter's insertion into the patient is also illustrated.
Figure 6:
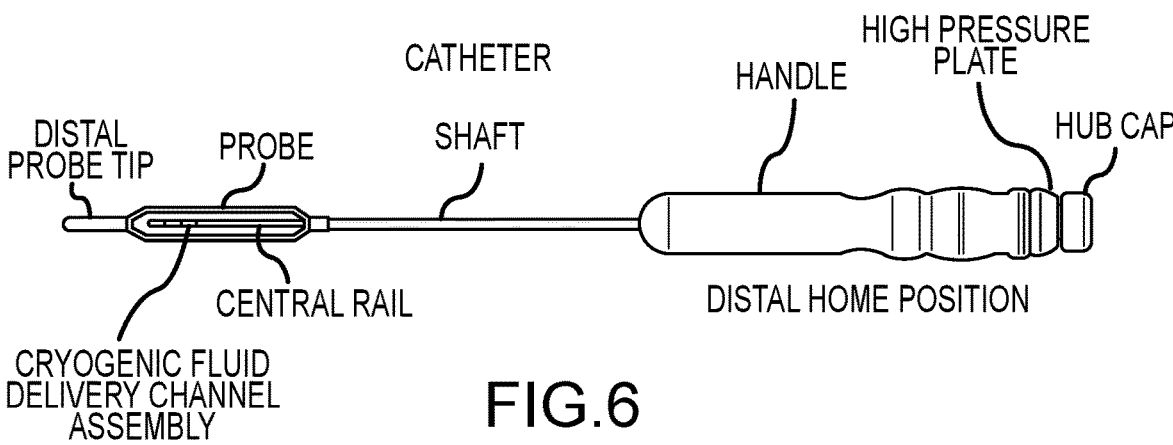
FIG. 6 is a side view of the catheter in the distal home position within the cryogenic ablation system. The controller omitted for clarity with the probe sectioned to illustrate the cryogenic fluid delivery channel assembly position.
Figure 7:
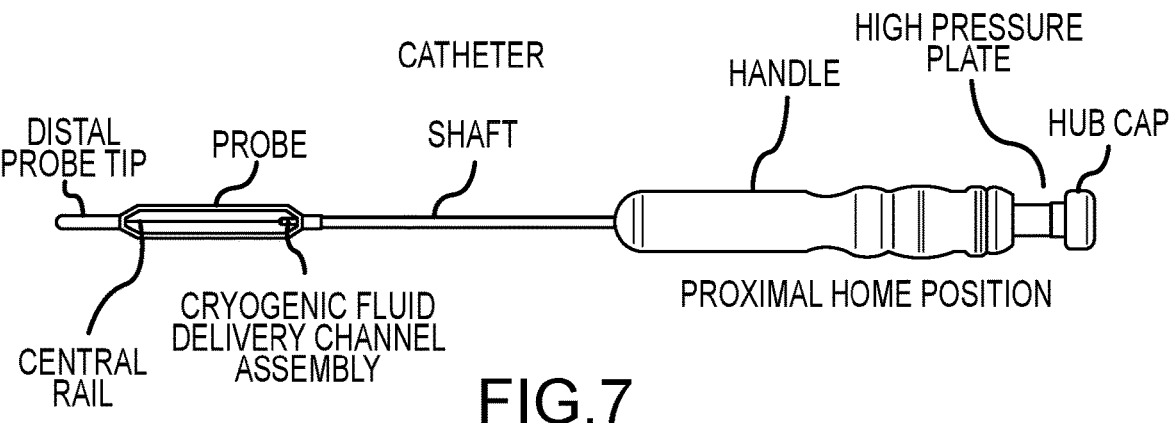
FIG. 7 is a side view of the catheter in the proximal home position within the cryogenic ablation system. The controller omitted for clarity with the probe sectioned to illustrate the cryogenic fluid delivery channel assembly position.

Referring to FIGS. 5-7, the high-pressure connector resides partially within the handle and partially outside the handle. The high-pressure plate and the hub cap are both parts of the high-pressure catheter connector that residue outside the handle.

Referring to FIG. 5 is an embodiment of the catheter shown in the load position, the hub cap is abutted to the high-pressure plate, and the high-pressure catheter connector cap is shown in place. The high-pressure catheter connector cap facilitates the catheter's insertion into an endoscope, an accessory channel, or inside an overtube or delivery sheath. Removal of the high-pressure catheter connector cap allows the catheter to be received into the controller. The catheter is inserted into and through the endoscope. Once the probe is in place, as confirmed by the user using the endoscope's visualization capabilities, the high-pressure catheter connector cap is removed from the catheter to be received into the controller. The catheter is inserted by using the handle with the high-pressure catheter connector end first into the controller connector until the catheter stops. The controller automatically detects the catheter's presence and indicates via the display that the catheter is secured and fluidly coupled to the controller.

Referring to FIG. 6 an embodiment of the catheter is shown in the distal home position or the maximum distal position where treatment may be performed. The catheter is coupled to the controller by means of the controller connector and the high-pressure catheter connector. Upon activating the appropriate user inputs using the display (touch-sensitive), the controller initiates the treatment motor moving the cryogenic fluid delivery channel assembly to the distal home position which is based on the catheter configuration.

Referring to FIG. 7 is an embodiment of the catheter shown in the proximal home position or the maximum proximal position where treatment may be performed. In this embodiment and configuration, the catheter is coupled to the controller by means of the controller connector and the high-pressure catheter connector. Upon activating the appropriate user inputs using the display (touch-sensitive), the controller initiates the treatment motor moving the cryogenic fluid delivery channel assembly to the one of the home positions which is based on the catheter configuration. Based on user input, the controller may initially move the cryogenic fluid delivery channel assembly to the distal home position (FIG. 6) or to the proximal home position (FIG. 7) The user may position the cryogenic fluid delivery channel assembly within the predefined home and proximal positions. The user controls the rate direction and distance the assembly travels within the treatment limits.

Figure 8A:
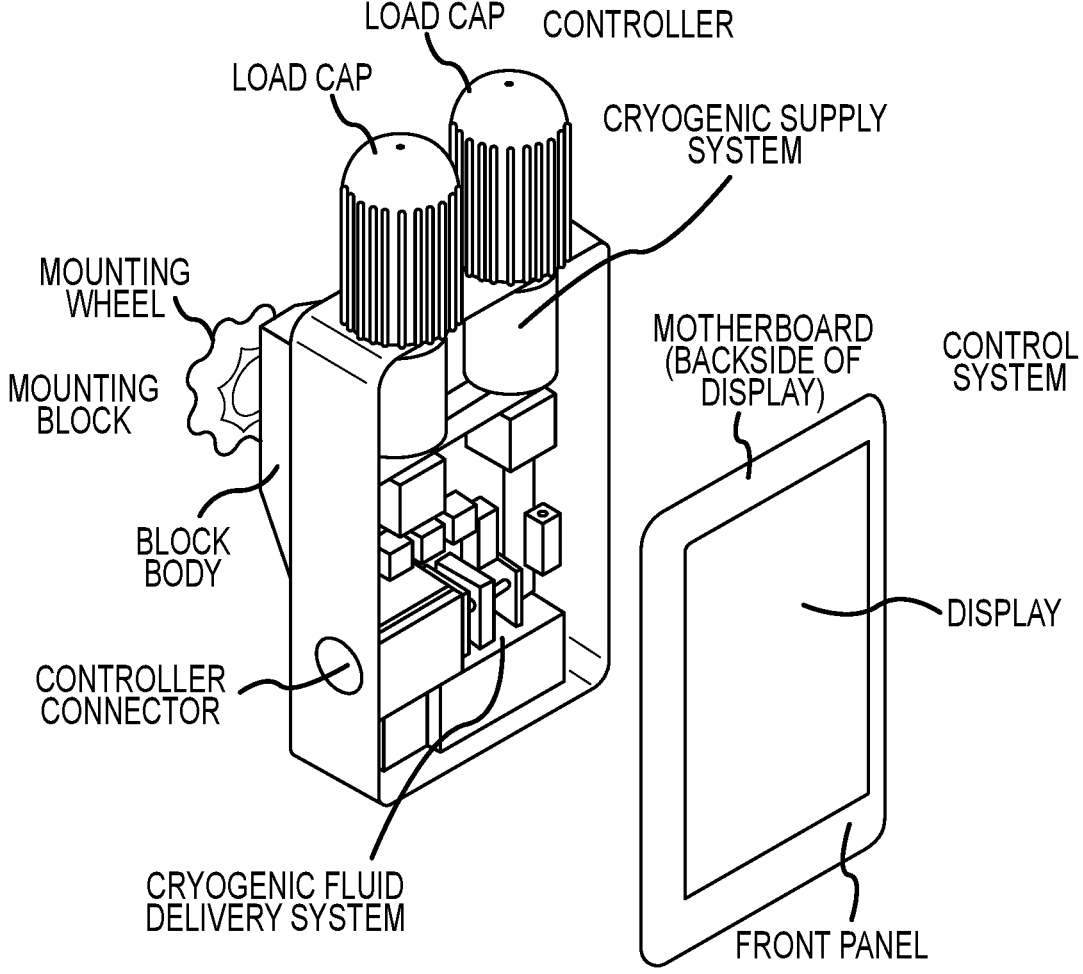
FIG. 8A is an exploded perspective view of the controller.

Referring to FIG. 8A, which is a perspective view of the controller's embodiment, which encompasses a control system, a cryogenic fluid delivery system, a cryogenic supply system, and the catheter connector manifold with the front panel removed, exposing the internal components. The control system connects all electronic components, allowing them to communicate together. The control system encompasses the display, motherboard (on the backside of the front panel), hardware, software with associated algorithms, and user interface, which in combination define treatment parameters. The control system includes but is not limited to the CPU, memory, storage facility video, sound, and other ports.

Figure 8B:
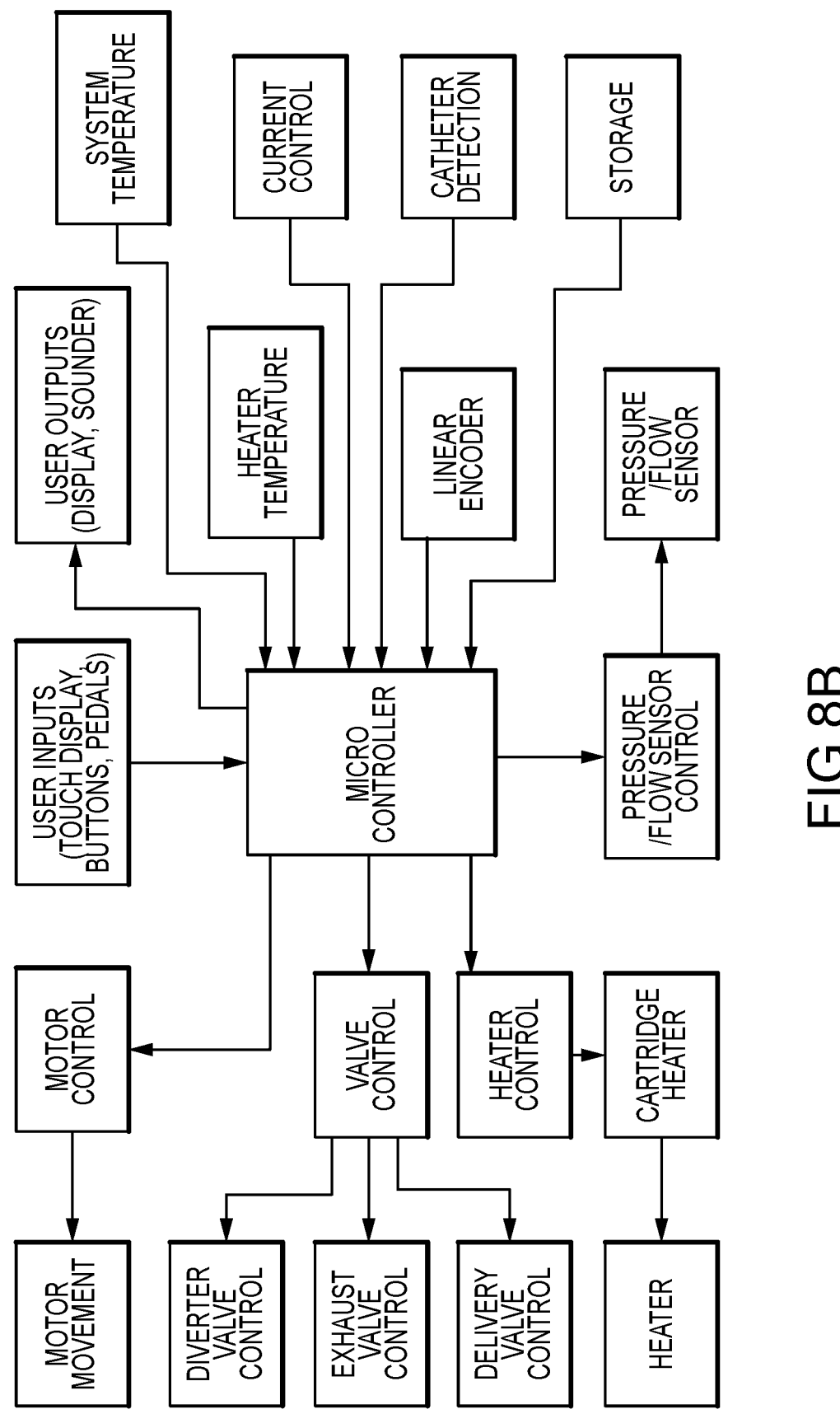
FIG. 8B is an overview diagram demonstrating the organization of the control system.

Referring to FIG. 8B is an overview diagram demonstrating the organization of the control system. The control system includes a display or user interface, a microcontroller, a motherboard, valve control, heater control, pressure and flow sensor control, motor control, user outputs, system temperature, catheter detection, storage, etc.

Figure 9:
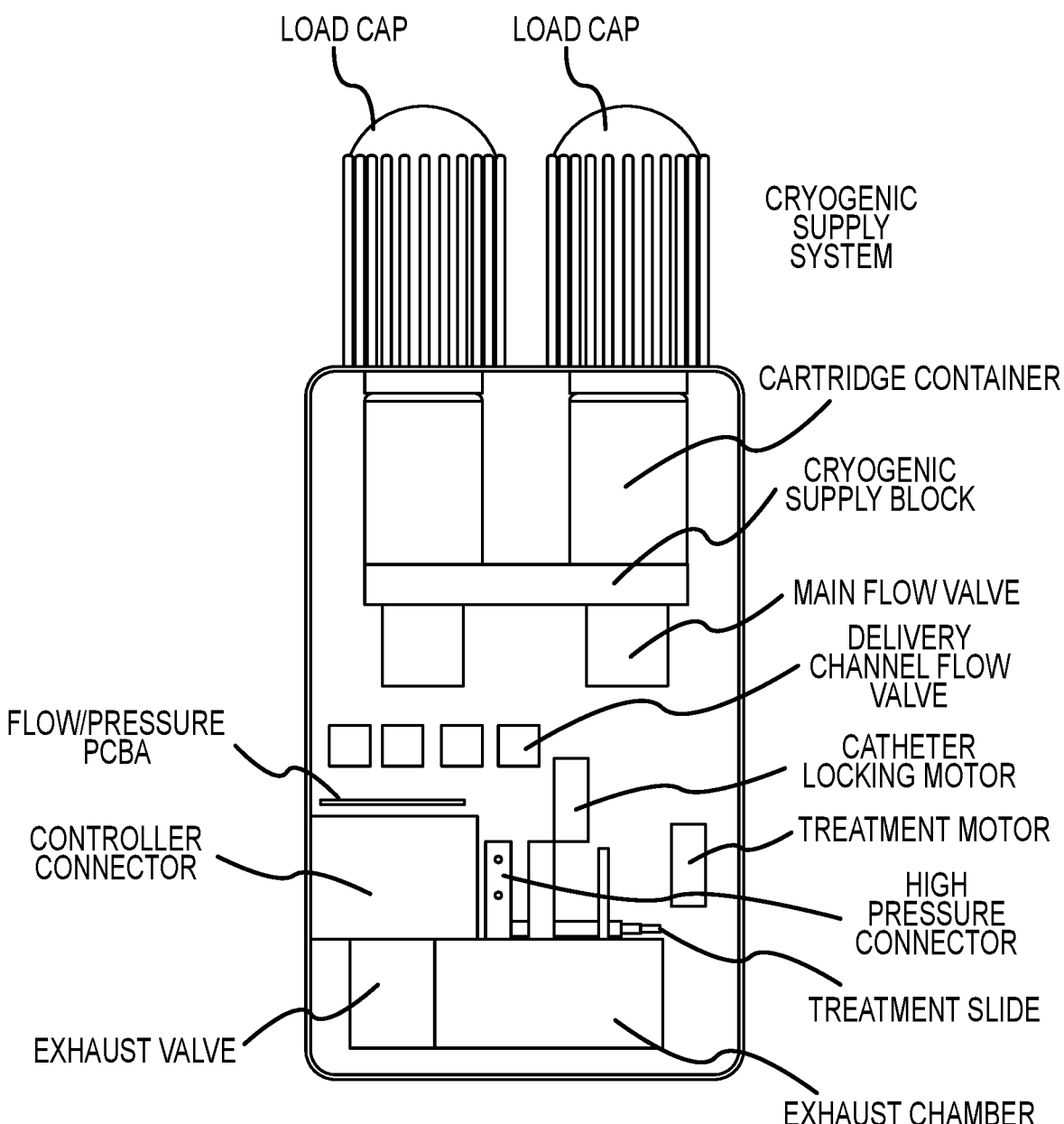
FIG. 9 is a front of the controller with the front panel missing for better visualization of the internal components.
Figure 20:
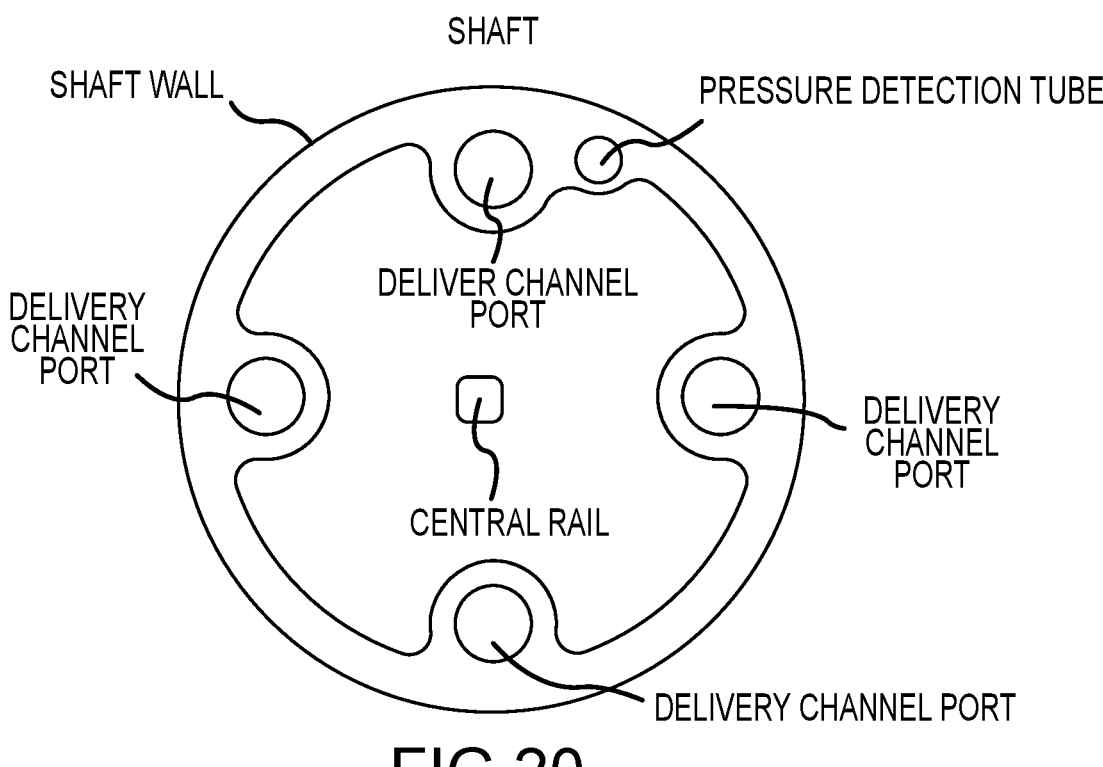
FIG. 20 is a cross-sectional view of the shaft.
Figure 21:
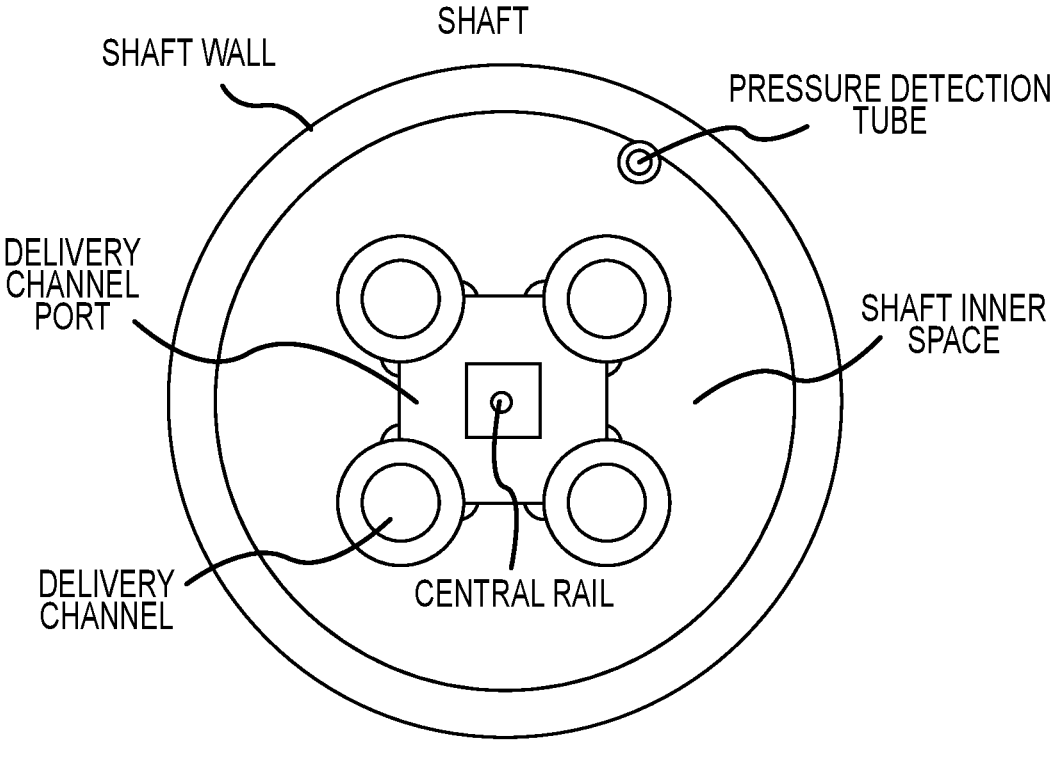
FIG. 21 is a cross-sectional view of the shaft.

Referring to FIG. 9 an embodiment of the controller with the front cover missing for better visualization of the internal components. The controller's cryogenic supply system may include one or more load caps, one or more cartridges (residing within the load caps), one or more of the cartridge containers, and a cryogenic supply block that connects the cryogenic supply system to the cryogenic fluid delivery system. The cryogenic fluid delivery system consists of one or more main flow valves controlling the flow of cryogenic fluid from the cryogenic supply system into one or more delivery channel flow valve(s) which controls the flow of cryogenic fluid into one or more cryogenic fluid delivery channel(s). The control system controls the main flow valve(s) and delivery channel flow valve(s). The control system controls the cryogenic liquid delivery system to automatically direct the cryogenic fluid flow at a predetermined start and stop time by using an electronic or mechanical timer. The control system controls the linear traversing rate that is either distal or proximal by means of the treatment motor with an optical sensor or magnetic reader that translates the channels within the probe at a precise rate and location The controller connector aligns the appropriate ports from the high-pressure catheter connector, so the cryogenic supply system is fluidly coupled to the cryogenic fluid delivery channel(s). The cryogenic fluid delivery system encompasses the catheter locking motor, which keeps the catheter securely in place and connected with the controller at the catheter connector manifold. Within cryogenic fluid delivery system can be configured with liquid flow port, exhaust, and probe pressure port. Measurements from these ports may be inputs to a control algorithm implemented on the cryogenic liquid delivery system. The operation of the controller may be regulated or adjusted based on sensor feedback. In some embodiments, it may be desirable for the control algorithm to be fully automated, but the delivered therapy may utilize user input in other embodiments. The high-pressure catheter connector and the controller connector facilitate the liquid connection when both are securely locked together. Once securely locked together, the treatment motor traverses the cryogenic delivery channels within the probe's predefined configuration. The exhaust valve controls are fluidly coupled to the catheter and control the gas outlet from the probe and into the exhausting chamber. The controller can be configured to automatically control the outlet of gas from the probe through the exhaust valve before, during, and after the cryogenic fluid is flowing through the probe. Once the cryogen fluid has converted into a gas within the probe, it is conveyed back into the controller through the shaft inner space (FIG. 20 and FIG. 21). It travels through the handle connector, exhaust valve, and into the exhaust chamber. Any remaining cryogen left within the cartridge after completing the therapy may be vented from the cartridge. The cartridge's venting conveys the cryogen fluid directly into the exhausting chamber. Once the cryogen has been contained within the exhaust chamber, it can be directed from the controller in several different ways. The exhaust from the system can be configured for direct or recovery of the gas.

Figure 10A:
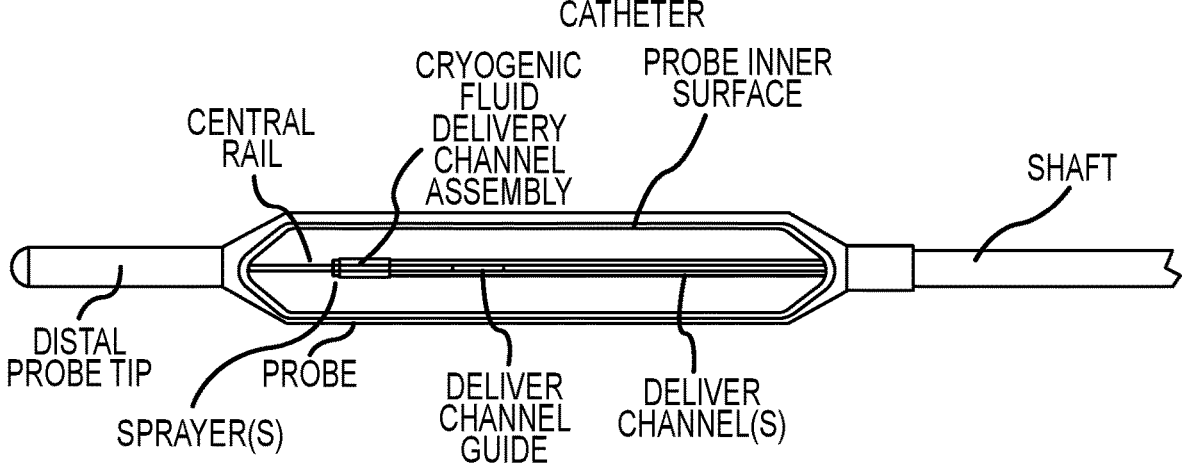
FIG. 10A is a cross-sectional side view of a portion of the catheter of the probe showing the central rail and cryogenic fluid delivery channel assembly.

Referring to FIG. 10A an embodiment of the catheter has been sectioned to visualize the components within the probe better. The central rail consists of a solid or hollow shaft keyed to accommodate the sprayer guide and the delivery channel guide for longitudinal movement between the pre-defined start treatment position and complete treatment position. One or more delivery channels are bonded, strapped, laser welded, etc., to the delivery channel guide. Any one or more of these methods may be used to secure the delivery channel(s) to the guides. The delivery channel(s) is extended within the catheter from the cryogenic fluid delivery channel assembly, through the shaft center, and into the high-pressure catheter connector. One or more delivery channel guides may be used along the length of the delivery channel(s). At the distal end, delivery channel is bonded, strapped, laser welded, etc., to a sprayer at the cryogenic fluid delivery channel assembly which encompasses one or more delivery channels, one or more sprayers, and one or more sprayer guides. The sprayer may be constructed from single or multiple components that will make up the sprayer configuration for directing the cryogenic fluid to the probe inner surface. Any one or more of these methods may be used to fluidly couple the delivery channel(s) to the sprayer(s). The sprayers are free to traverse longitudinally across the probe in either direction which may be distal to proximal or proximal to distal. Longitudinal movement may also cover a portion of the probe length or the full probe length. A non-keyed shaft or a section of the keyed shaft may be configured to allow rotational movement of the cryogenic fluid delivery channel assembly based on the catheter con-figuration. The distal probe tip can be configured to secure the central guide rail within the probe tip. The proper material selection (any material that provides minimal flex-ure during use, steel, alloys, resin-based materials, some material selections may also be treated to improve rigidity) of the central rail provides stability to the cryogenic fluid delivery channel assembly while allowing the catheter to be flexible enough to wind its way through the twists and turns of the gastrointestinal tract. Further, the central guide rail facilitates the probe's elongated state during the introduction and removal of the catheter from the endoscope. Both the sprayer guide and the delivery channel guide must be made from a material that provides little to no resistance during the linear movement. The delivery channel must contain a smooth inner surface or be lined to allow for the cryogenic fluid's consistent and continuous flow. The probe may be comprised of a compliant or a non-compliant material. The probe is fluidly coupled to the tapered distal probe end which may be tapered of the shaft by one or materials being thermal bonded or adhered together.

Figure 10B:
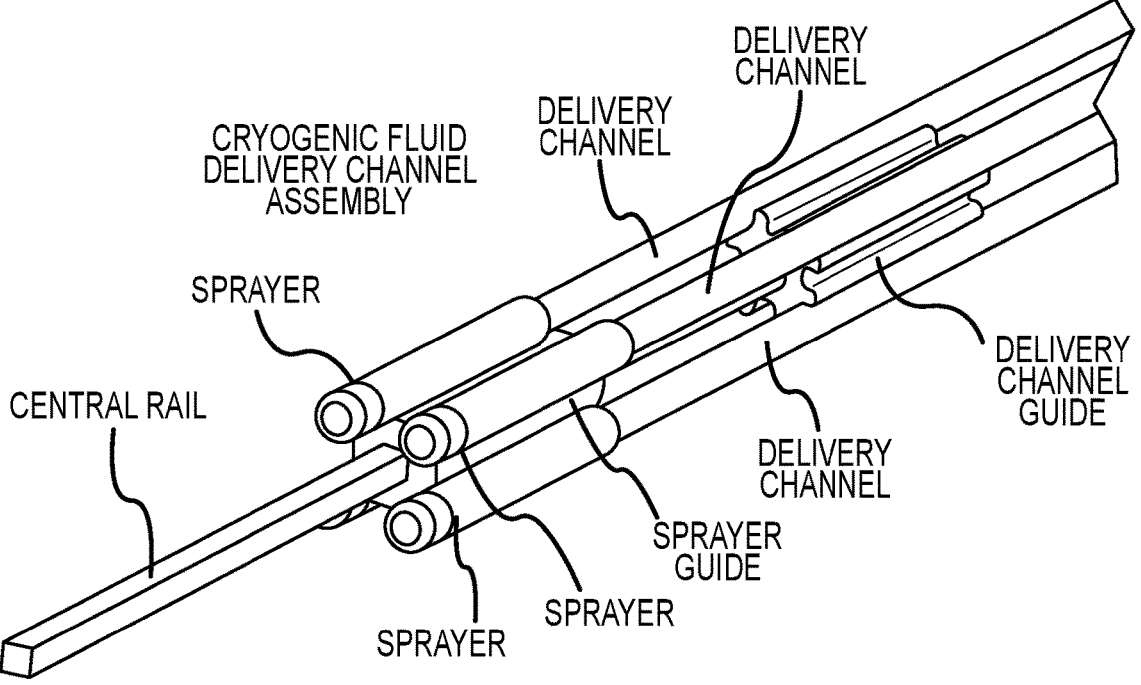
FIG. 10B is a perspective view of the cryogenic fluid delivery channel assembly and the central rail.

FIG. 10B is a perspective view and close up of the quad-core design of the cryogenic fluid delivery channel assembly which encompasses one or more delivery chan-nels, one or more sprayers, and one or more sprayer guides. The central rail is also depicted. The delivery channels are also shown extending to the shaft. A delivery channel guide is also shown.

Figure 11:
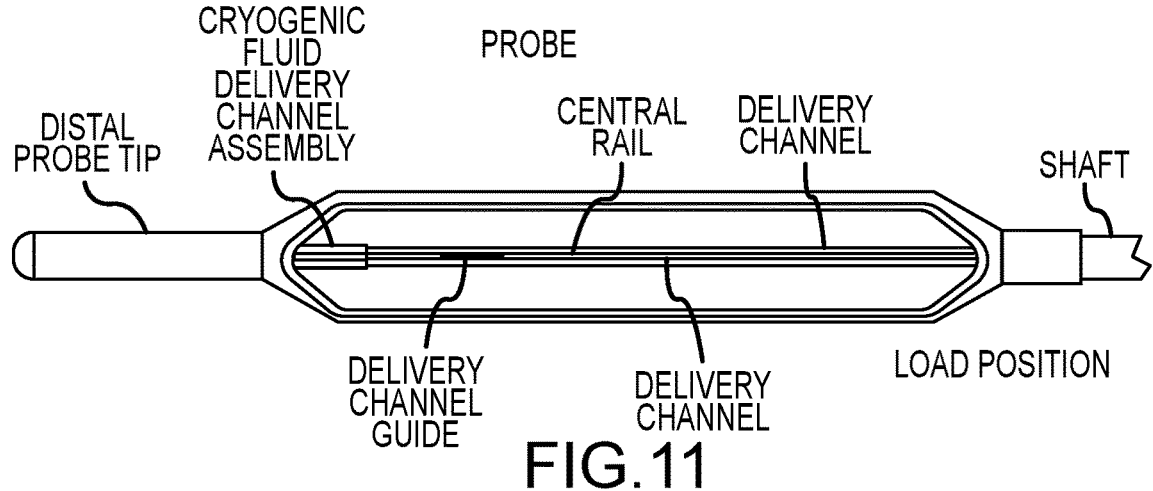
FIG. 11 is a cross-sectional side view of a portion of the catheter of the probe showing the central rail and cryogenic fluid delivery channel in the load position.

Referring to FIG. 11 is an embodiment of the catheter configured in the load position focused and sectioned to visualize the probe's components. The central rail is extended most distal within the probe, which maximizes the probe's longitudinal characteristic elongating the probe to facilitate an easy introduction of the catheter into and through the endoscope. In this embodiment, the cryogenic fluid delivery channel assembly is also extended most distal within the probe. After the catheter insertion through the endoscope, the high-pressure catheter connector cap is removed and the catheter is inserted controller via the handle, high-pressure catheter connector, and the controller connector. After insertion into the controller, the cryogenic liquid delivery controller display indicates that the catheter has been fully installed, secured, and fluidly coupling the catheter to the controller.

Figure 12:
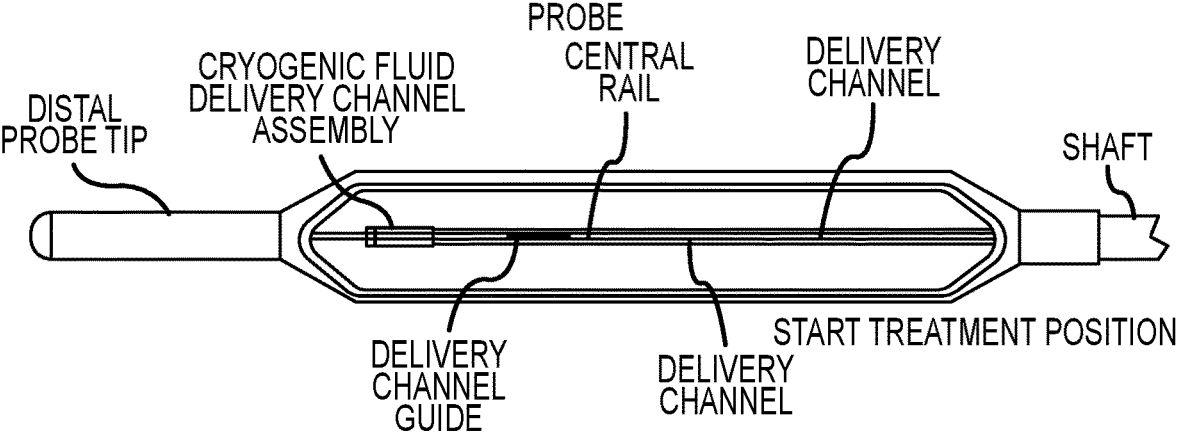
FIG. 12 is a cross-sectional side view of a portion of the catheter of the probe showing the central rail and cryogenic fluid delivery channel in the start treatment position.

Referring to FIG. 12 is an embodiment of the catheter configured in the distal home position focused and sectioned to visualize the probe's components better. The catheter has been inserted into the endoscope, fluidly coupled to the controller, and the cryogenic fluid delivery channel has moved to the distal home position. Based on user input, the controller may initially move the cryogenic fluid delivery channel assembly to the distal home position (FIG. 6) or the proximal home position (FIG. 7). The distal home and proximal home positions are predefined limits of the treat-ment range based on the probe configuration. Both the distal home and proximal home positions are hard stop fixed locations determined based on the portion of the probe that makes intimate contact with the tissue. Based on the treat-ment algorithm, the start treatment position may be at the distal home position or the proximal home position, or any place between them. In this embodiment, both the start treatment position and the distal home position are the same.

Figure 13:
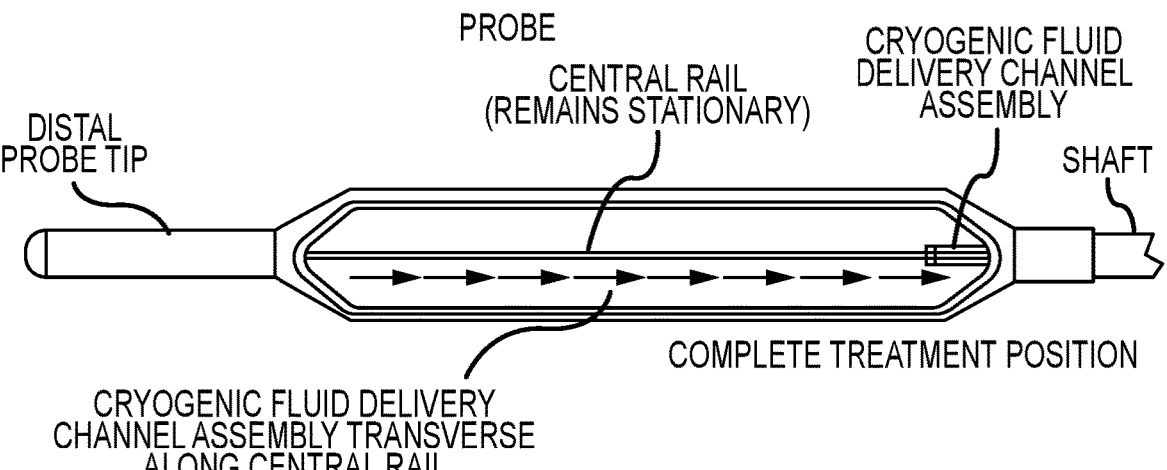
FIG. 13 is a cross-sectional side view of a portion of the catheter of the probe showing the central rail and cryogenic fluid delivery channel in the complete treatment position.

Referring to FIG. 13 is an embodiment of the catheter shown in the complete treatment position that has been focused, sectioned to visualize the probe's components better. Both the start and complete treatment positions are predefined based on user input. The user may also complete treatment at any time during the treatment cycle. FIG. 13 illustrates the cryogenic fluid delivery channel assembly traversing from the start treatment position to the complete treatment position. The center guide rail provides longitu-dinal support while the cryogenic fluid delivery channel assembly is traversing the probe. The cryogenic fluid deliv-ery channel assembly movement is controlled by the treat-ment motor, which may be a geared motor with an optical sensor or magnetic reader that translates the channels at a precise rate, direction, and location. Once the treatment cycle is complete, the cryogenic fluid delivery channel assembly may be repositioned within the distal home and proximal home positions. A treatment cycle may be in the distal to proximal direction or proximal to distal and the start. During the treatment cycle, the sprayer assembly is held rotationally fixed, ensuring a repeatable application of cryogenic fluid to the desired tissue.

Figure 14A:
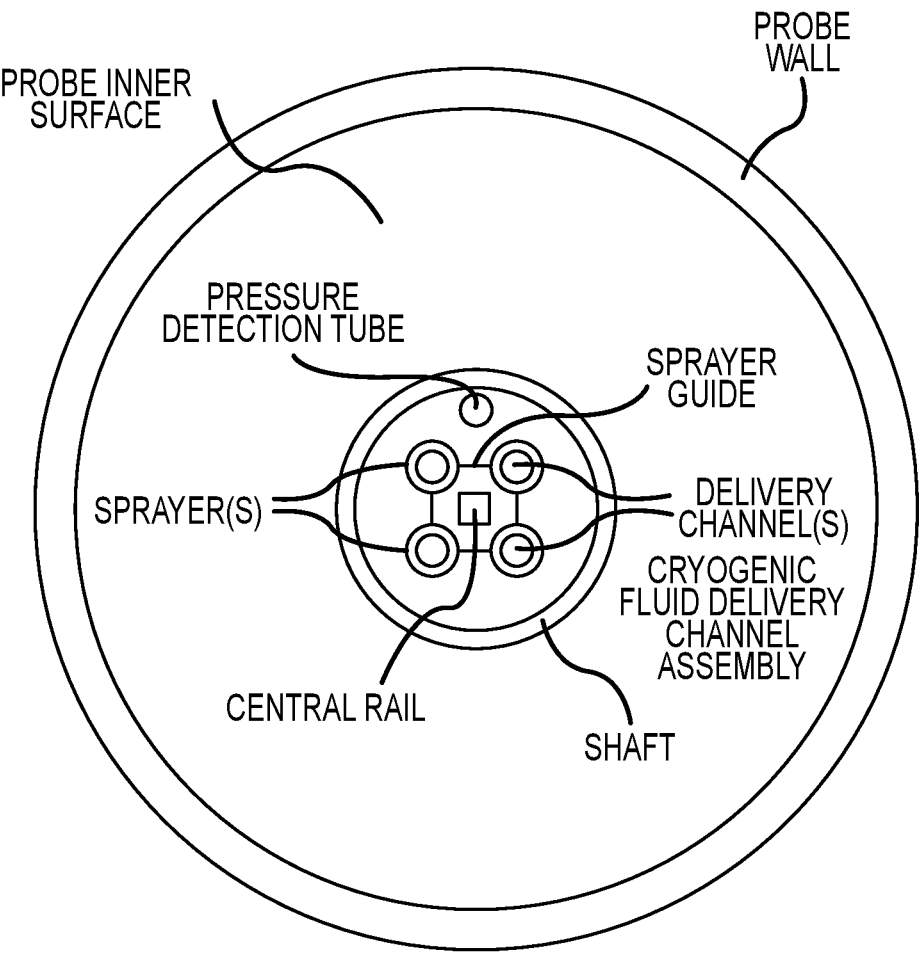
FIG. 14A is a cross-sectional view of the catheter at the distal portion of the probe showing the quad-core design of the cryogenic fluid delivery channel assembly.
Figure 14B:
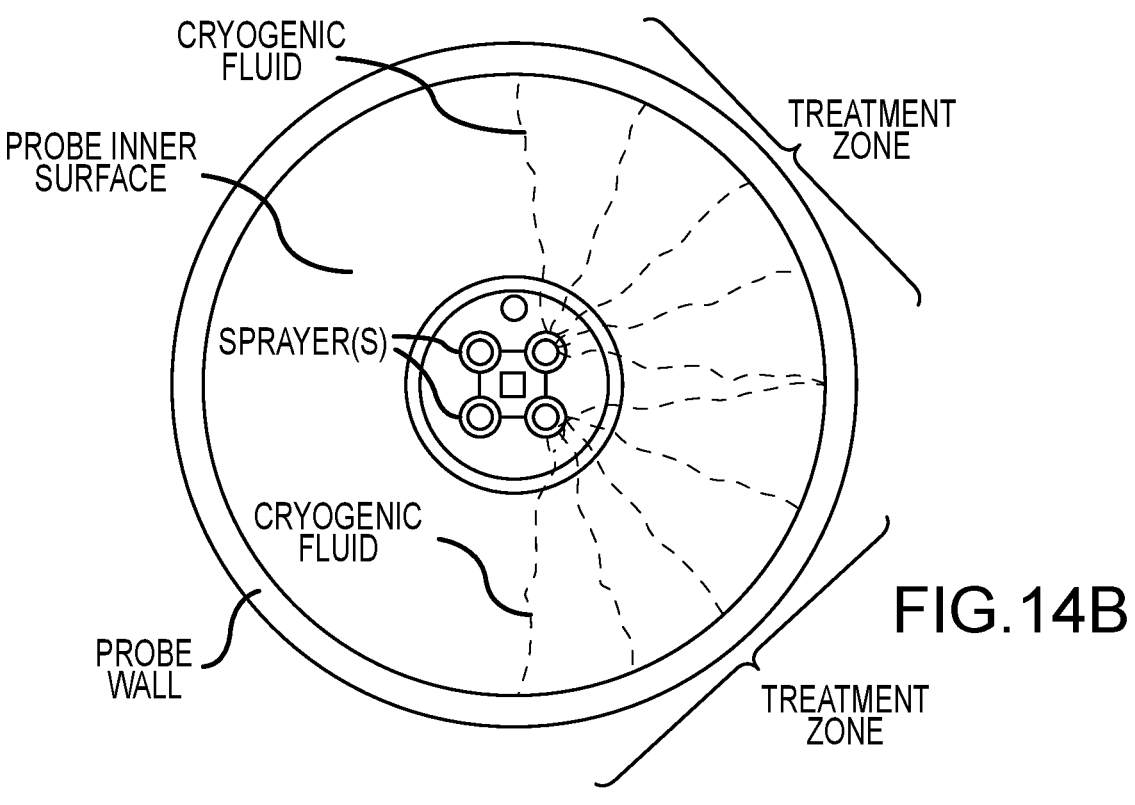
FIG. 14B is a cross-sectional view of the catheter at the distal portion of the probe showing the quad-core design of cryogenic fluid delivery channel assembly and illustrates the treatment zone.
Figure 14C:
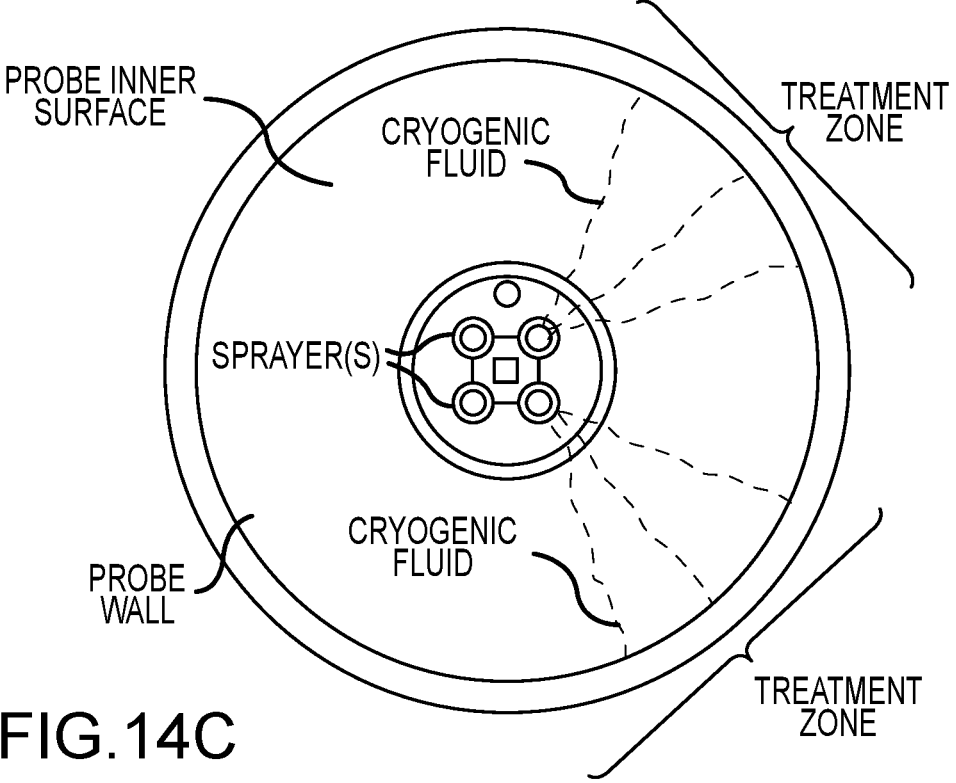
FIG. 14C is a cross-sectional view of the catheter at the distal portion of the probe showing the quad-core design of cryogenic fluid delivery channel assembly and illustrates the treatment zone.
Figure 14D:
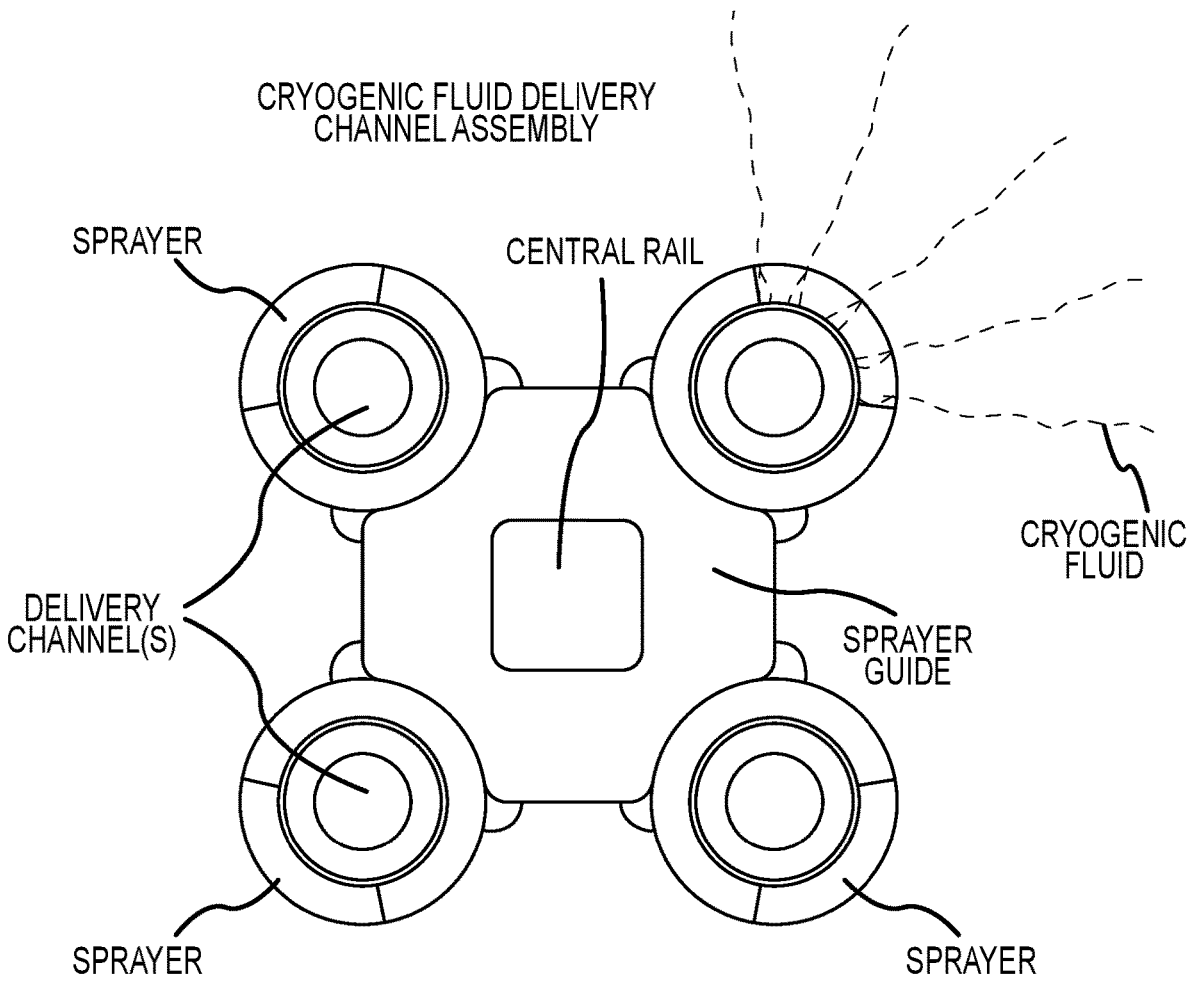
FIG. 14D is a cross-sectional view of the quad-core design of the cryogenic fluid delivery channel assembly and illustrates application of cryogenic liquid from a sprayer.

Referring to FIG. 14A is a cross-sectional view of the embodiment of the catheter at the distal portion of the probe facing towards the high-pressure catheter connector. This catheter has been configured with the quad-core design where 4 delivery channels and 4 sprayers are present. The catheter may have one or more delivery channels and one or more sprayers. Referring to FIG. 14B, in this embodiment, cryogen fluid is directed from sprayer(s) outward into the probe inner surface to the probe wall which is in intimate contact with the tissue of the gastrointestinal tract. Each sprayer is configured to apply a thin blade of cryogenic fluid to one quarter (¼) of the probe wall inner circumference. This blade can be traversed across the probe at any speed within the motor's capability. Referring to FIG. 14C, in this embodiment, each sprayer is configured to apply a blade of cryogen fluid of at least 1 mm thick to less than one quarter (¼) of the probe wall inner circumference. Each sprayer can be configured to apply one-quarter (¼) circumference, less than one-quarter (¼) circumference, or more than one-quarter (¼) circumference. Referring to FIGS. 14B and 14C, in this embodiment, two of the four sprayers are applying a blade of cryogen fluid into the probe inner surface and to the inner portion of the probe wall. The invention can be configured so one or more sprayers can be configured to simultaneously apply cryogen fluid based on the algorithm selected and controlled by the control system. Referring to FIG. 14D, which is a cross-section view of the cryogen fluid delivery channel assembly and illustrates application of cryogen fluid from a sprayer.

Figure 15A:
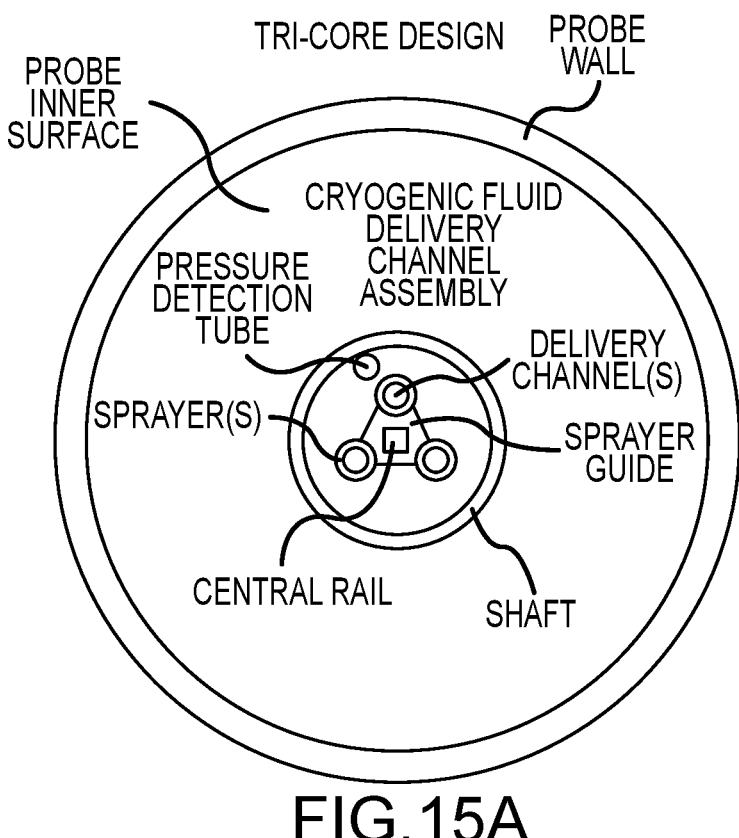
FIG. 15A is a cross-sectional view of the catheter at the distal portion of the probe showing the tri-core design of the cryogenic fluid delivery channel assembly.
Figure 15B:
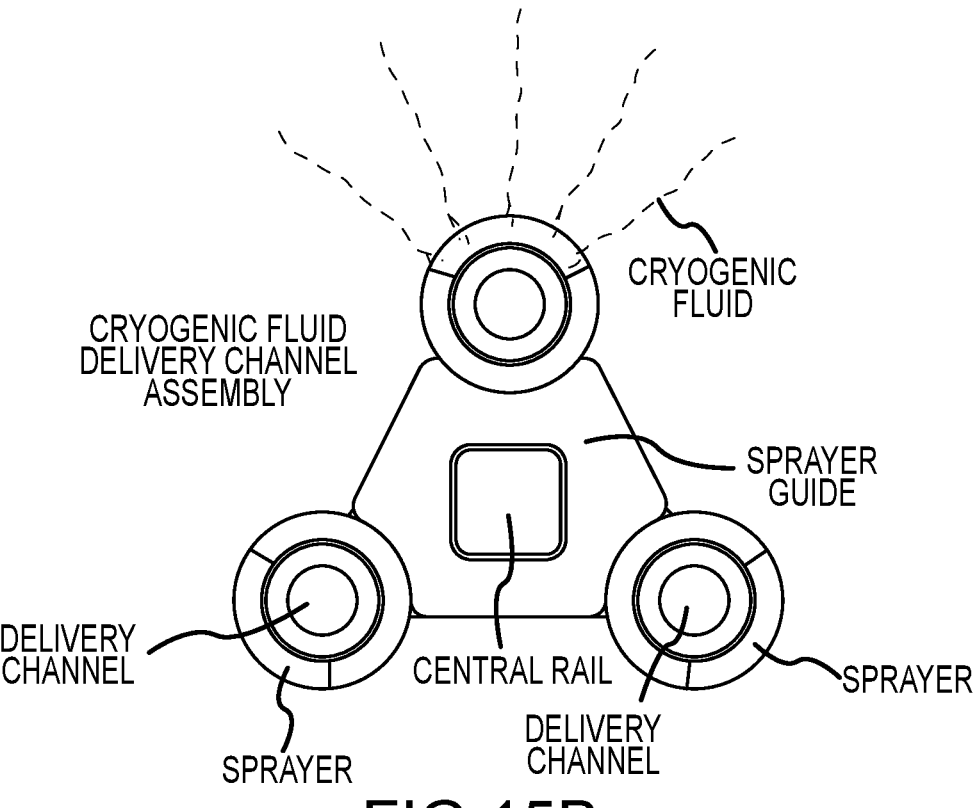
FIG. 15B is a cross-sectional view of the tri-core design of the cryogenic fluid delivery channel assembly and illustrates application of cryogenic liquid from a sprayer.

Referring to FIG. 15A is a cross-sectional view of the embodiment of the catheter at the distal portion of the probe facing towards the high-pressure catheter connector. This catheter has been configured with the tri-core design where 3 delivery channels and 3 sprayers are present (see FIG. 15B). The catheter may have one or more delivery channels and one or more sprayers. Each sprayer may be configured to apply a blade of cryogen fluid to one third (⅓) of the probe wall inner circumference which is in intimate contact with the tissue of the gastrointestinal tract. As with the Quad-Core design, each sprayer may be configured to apply more than one-third (⅓) of the probe wall inner circumference or less than one-third (⅓) of the probe wall inner circumference. The invention can be configured so one or more sprayers can be configured to simultaneously apply cryogen fluid based on the algorithm selected and controlled by the control system.

Figure 16:
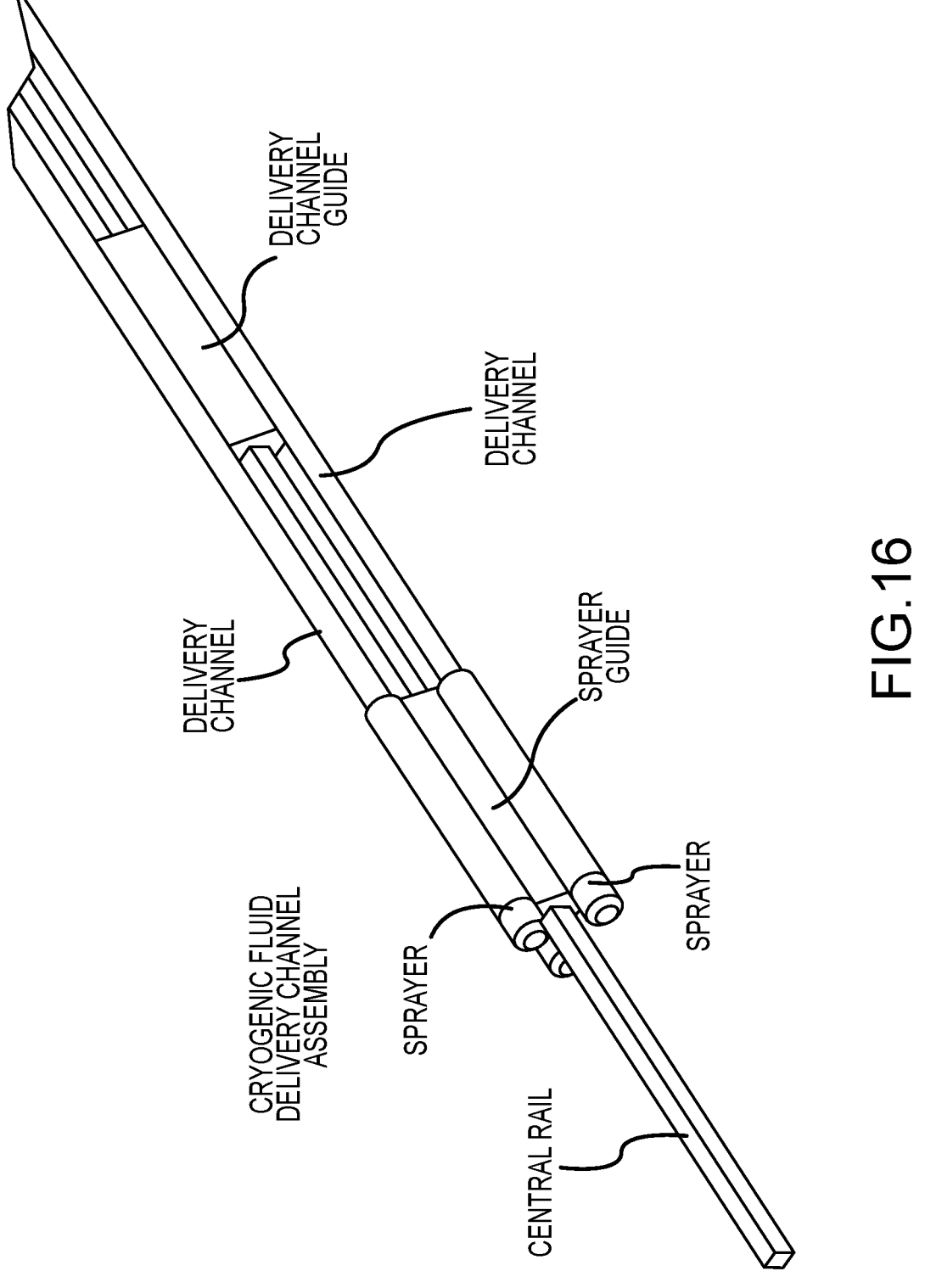
FIG. 16 is a perspective view of the cryogenic fluid delivery channel assembly and the central rail.

FIG. 16 is a perspective view and close up of the Tri-Core design of the cryogenic fluid delivery channel assembly which encompasses one or more delivery channels, one or more sprayers, and one or more sprayer guides. The central rail is also depicted. The delivery channels are also shown extending to the shaft. A delivery channel guide is also shown.

Figures 17A, 17B, 17C, 17D:
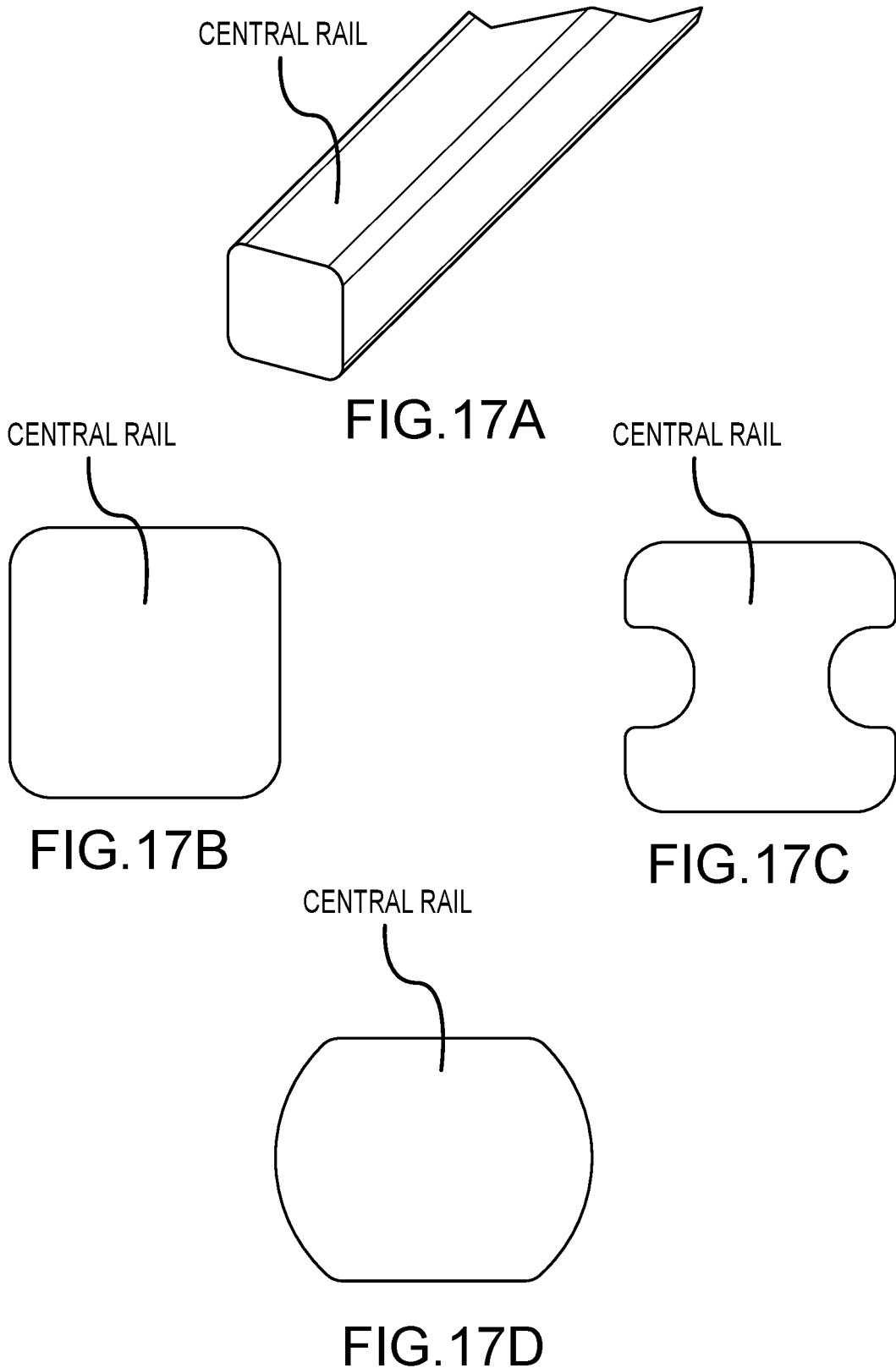
FIG. 17A is a perspective view of the square central rail.
FIG. 17B is an end view of the square central rail.
FIG. 17C is an end view of the I-beam central rail.
FIG. 17D is an end view of the double-D central rail.

Referring to FIG. 17A, is a perspective view of the central rail within the catheter which is secured to the catheter proximal and distal end, the high-pressure catheter connector, and the probe tip. The central rail is keyed and provides a stable platform for the cryogenic fluid delivery channel assembly to glide over. Further, FIG. 17B is an end view of the central rail that is shown in FIG. 17A. One or more configurations of the central rail may be used within the catheter. The catheter is not limited to any single central rail configuration. FIGS. 17B and 17C show two additional potential central rail configurations. Any shape that limits the rotational characteristic of the sprayers can be used. For the single sprayer system a round or circular shape center rail will be used to accommodate rotation.

Figure 18:
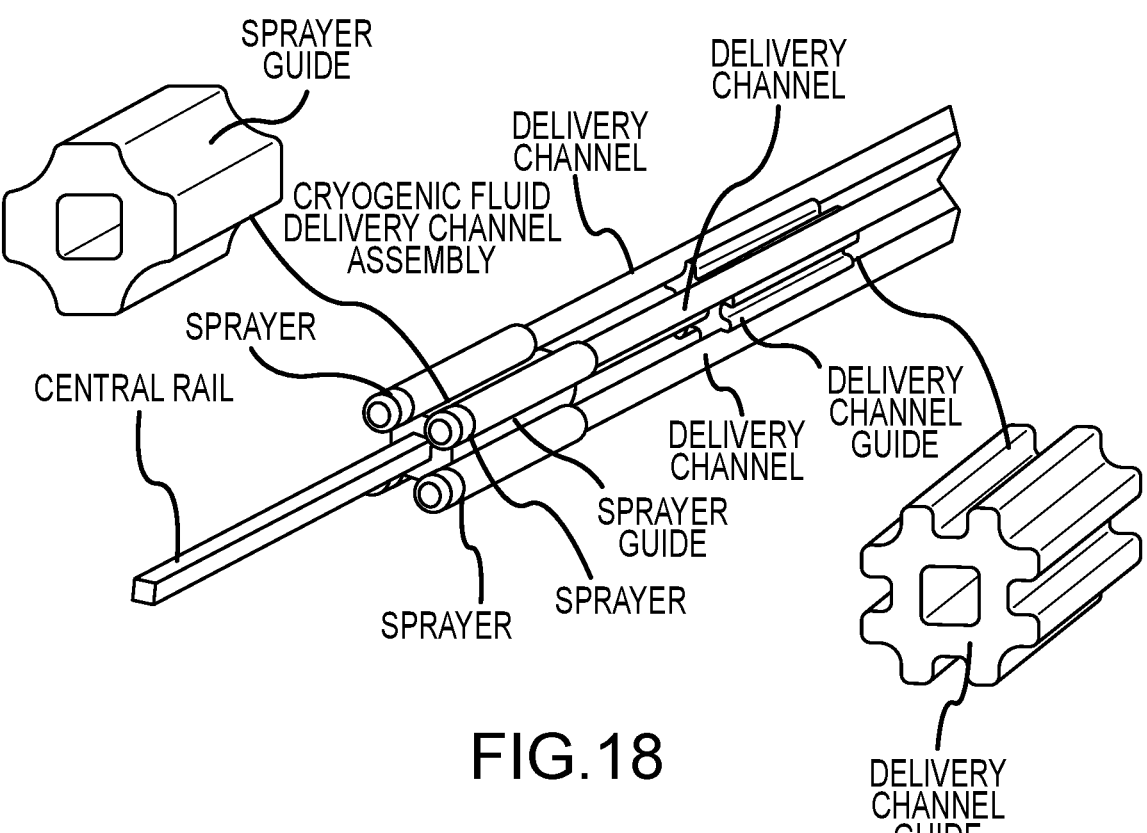
FIG. 18 is a perspective view of a portion of the catheter of the quad-core design of the central rail, cryogenic fluid delivery channel assembly, sprayer guide, and the delivery channel guide.

Referring to FIG. 18 which is an embodiment of the cryogenic fluid delivery channel assembly in perspective. The sprayer guide and the delivery channel guide have been pulled out of the assembly for better visualization of the component. The sprayer guide is positioned directly beneath the sprayers, while the delivery channel guide is positioned directly beneath and can be configured along the entire length of the delivery channels up to the high-pressure catheter connector. One or more sprayer guides and more or more delivery channel guides may be used. The sprayer guide(s) and the delivery channel guide(s) enable the system to operate as a single unit. The configuration shown is the Quad-Core design with four delivery channels and four sprayers. The cryogenic fluid delivery channel assembly may encompass one or more delivery channels, one or more sprayers, and one or more sprayer guides. Adhesive and/or a heat-shrinkable plastic tube or other means could be utilized in securing the sprayer(s) to the sprayer guide(s) and the delivery channel(s) to the delivery channel guide(s). The sprayer guide and delivery channel guide material can be selected from a lubricous substance that is both rigid and tough. When fully assembled within the cryogenic liquid delivery assembly, this substance will not restrict movement along the central rail.

Figure 19:
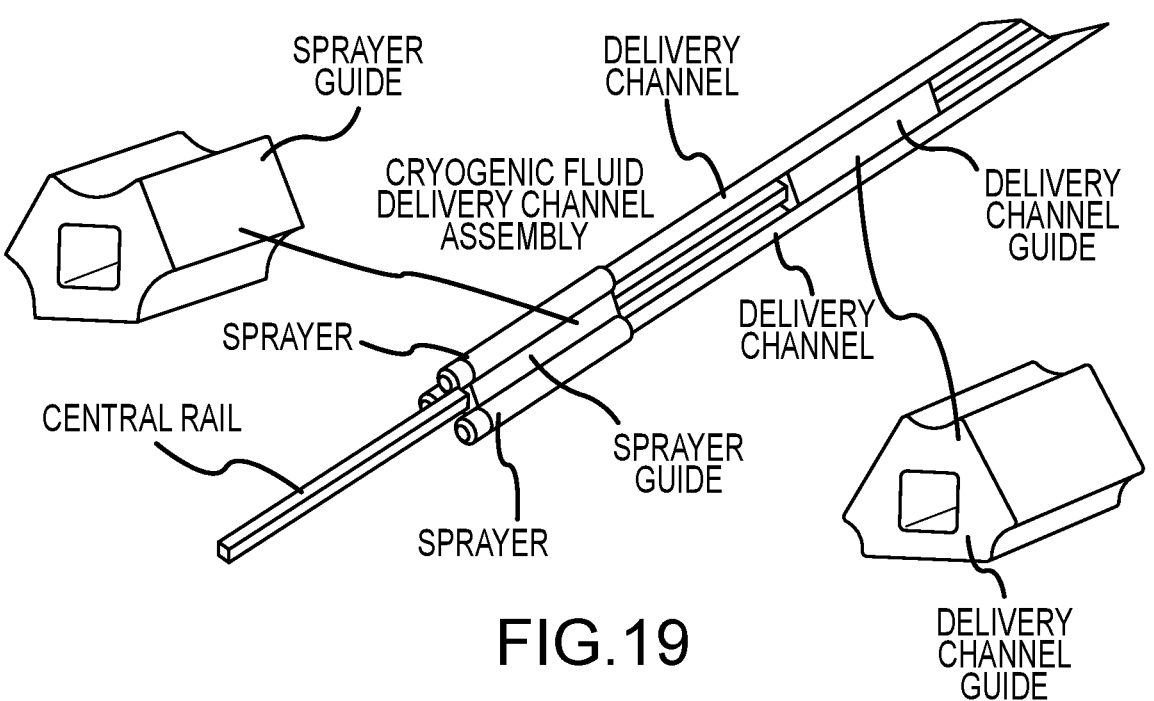
FIG. 19 is a perspective view of a portion of the catheter of the tri-core design of the central rail, cryogenic fluid delivery channel assembly, sprayer guide, and the delivery channel guide.

Referring to FIG. 19 which is an embodiment of the cryogenic fluid delivery channel assembly in perspective. The sprayer guide and the delivery channel guide have been pulled out of the assembly for better visualization of the component. The sprayer guide is positioned directly beneath the sprayers, while the delivery channel guide is positioned directly beneath and can be configured along the entire length of the delivery channels up to the high-pressure catheter connector. One or more sprayer guides and more or more delivery channel guides may be used. The sprayer guide(s) and the delivery channel guide(s) enable the system to operate as a single unit. The configuration shown is the Tri-Core design with three delivery channels and three sprayers. The cryogenic fluid delivery channel assembly may encompass one or more delivery channels, one or more sprayers, and one or more sprayer guides. Adhesive and/or a heat-shrinkable plastic tube or other means could be utilized in securing the sprayer(s) to the sprayer guide(s) and the delivery channel(s) to the delivery channel guide(s). The sprayer guide and delivery channel guide material can be selected from a lubricous substance that is both rigid and tough. When fully assembled within the cryogenic liquid delivery assembly, this substance will not restrict movement along the central rail.

Referring to FIG. 20 is a cross-sectional view of the shaft. The configuration shown is a Quad-Core design where four delivery channels pass through the shaft via four delivery channel ports that are incorporated into the shaft wall. One or more delivery channels and one or more delivery channel ports may be used. The shaft can be selected from a lubricous substance that is both flexible and tough. The central rail passes through the shaft inner space. The pressure detection tube can be incorporated into the wall of the shaft or ran as a separate tube from the controller connector to within proximity of the probe. This pressure detection tube is used to obtain a consistent pressure measurement of the probe. Additional configurations would use similar elements that embody their configuration (i.e., single, dual, tri, etc. configurations).

Referring to FIG. 21 is a cross-sectional view of the shaft. The configurations shown is a Quad-Core design where four delivery channels pass through the shaft inner space and where the delivery channel(s) are connected to delivery channel guide(s). One or more delivery channels and one or more delivery channel guides may be used. Adhesive and/or a heat-shrinkable plastic tube or other means could be utilized in securing the delivery channel(s) to the delivery channel guide(s). The central rail is located in the center of the delivery channel guide(s). The pressure detection tube can be incorporated into the wall of the shaft or ran as a separate tube from the handle connector to within proximity of the probe. This pressure detection tube is used to obtain a consistent pressure measurement of the probe. The shaft material can be selected from a lubricous substance that is both flexible and durable.

Figure 22:
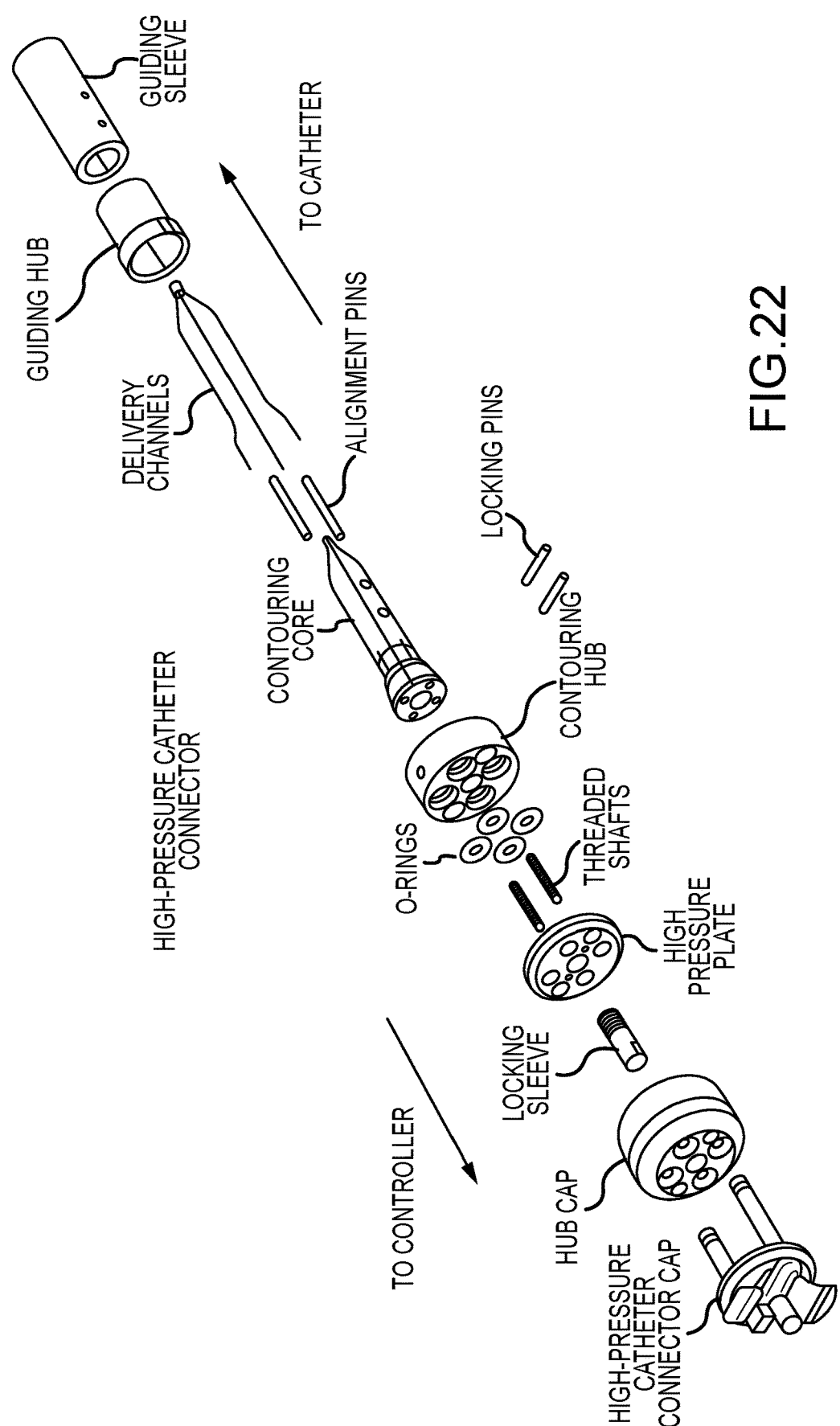
FIG. 22 is a perspective view of the high-pressure catheter connector.

Referring to FIG. 22 is an embodiment of the high-pressure catheter connector exploded perspective view. The delivery channels that extend beyond the high-pressure catheter connector into the shaft to the probe have been omitted. The configuration shown is the quad-core design with four delivery channels. The high-pressure catheter connector may have one or more delivery channels. Additional configurations would use similar components that embody their configuration (i.e., single, dual, tri and quad configurations, or more). The high-pressure catheter connector facilitates that the controller and catheter fluidly coupled together and contouring the delivery channels from the controller connection to the sprayers within the probe. The delivery channels are secured within the contouring hub, while the contouring core is aligned using the alignment pins and secured to the hub using the threaded shafts. The delivery channels are aligned within the grooves of the core then the guiding hub slides over the core contouring the delivery channels. Then the guiding sleeve is mated to the assembly and slid over the core, completing the channels' contouring. The locking pins are secured through the components locking the assembly together and completing the final profile into the shaft to the probe. The O-rings are installed into the contouring hub and secured using the high-pressure plate. The locking sleeve is secured to the contouring hub, and the hub cap is snapped into place. The high-pressure catheter connector cap is installed.

Referring to FIG. 23, a side view of the controller and catheter locking mechanism. The embodiment includes the locking sleeve which is a component of the high-pressure catheter connector and the lock receiver which is a component of the controller connector. Both components are shown before the two components' engagement. The hub cap from the high-pressure catheter connector has been omitted to better illustrate the catheter's locking mechanism to the controller.

Referring to FIG. 24 which is a side view of the steps of the controller and catheter locking mechanism. Now referring to FIG. 22 and FIG. 24, during the introduction of the catheter into the controller connector, the high-pressure catheter connecter will slide over the guide shafts aligning the locking sleeve to the lock receiver. During Step 1, locking sleeve tab(s), where there may be one or more locking sleeve tabs, slide up the ramp on the lock receiver, where there may be one or more ramps. During Step 2, the locking sleeve tab(s) move into the recess securing the catheter to the controller. When the catheter locking sleeve tabs enter the recess, a circuit is completed indicating to the microcontroller that the catheter has been coupled to the controller connector. The catheter is now coupled to the controller by means of the high-pressure catheter connector and is ready for cryogenic fluid to flow through the cryogenic ablation system. During Step 3, the user interfaces with the display on the controller selecting the eject icon. At that point, the disengagement motor connected to the receiver shaft rotates the lock receiver, where the locking sleeve tab(s) runs along the curved channel, unlocking, ejecting, and resetting the lock receiver ready for the next catheter. During Step 4, the locking sleeve tab(s) rotate along the curved channel(s) until the catheter has been unlocked and ejected from the controller.

Figure 25:
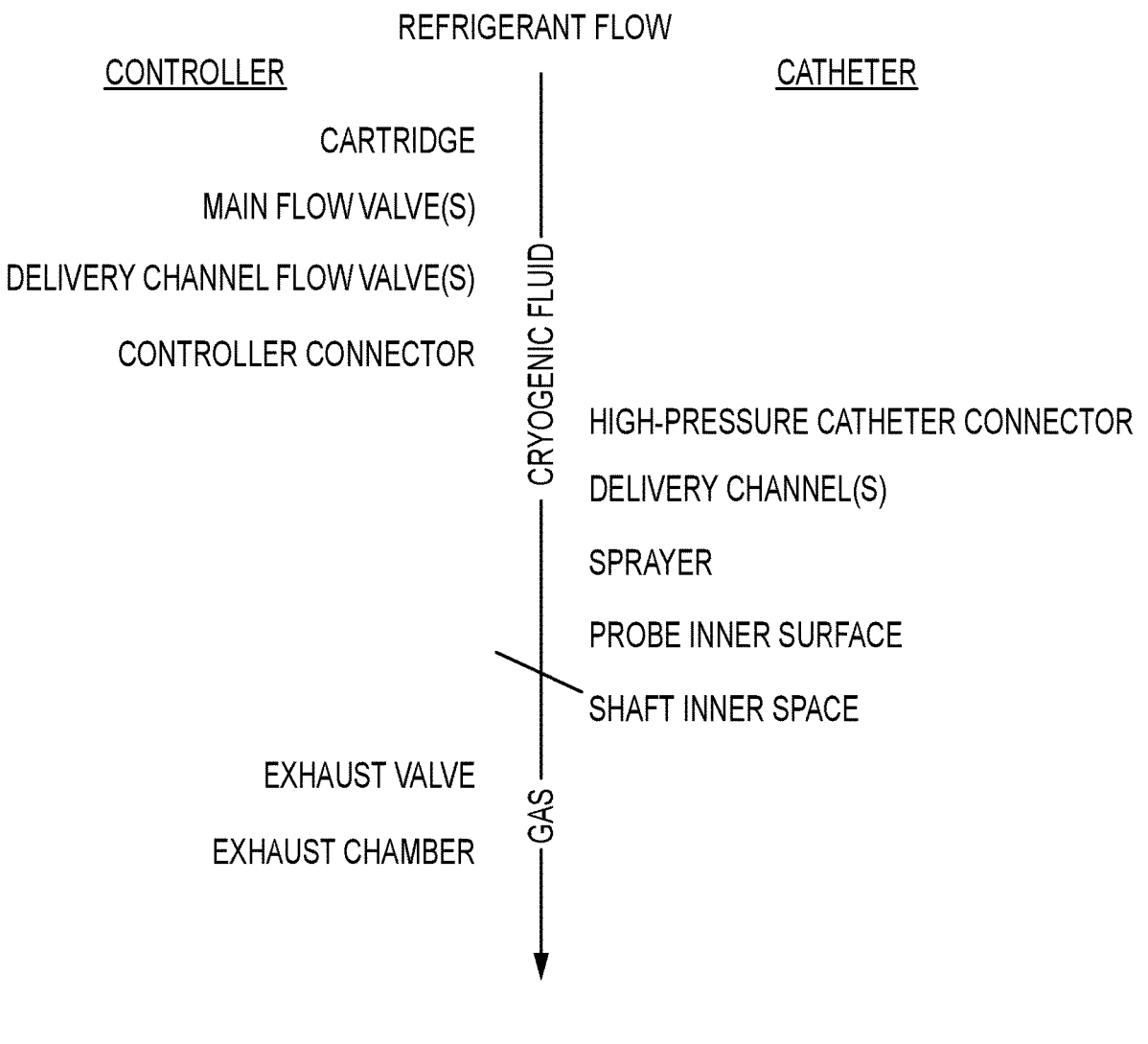
FIG. 25 is a schematic diagram of the cryogen path and phase.

Referring to FIG. 25, an overview diagram illustrating the cryogenic pathway and phase of the cryogen (liquid, liquid+ vapor or fluid, or gas phases) moves through the cryogenic ablation system components. In the canister, the cryogenic fluid is subcritical at room temperature, meaning that the fluid is both a liquid and vapor that coexist within the closed canister with the liquid being moderately dense liquid and where the cryogen is nitrous oxide or another cryogen such as CO2. The cryogenic fluid is maintained within a specific pressure range that is not less than 250 psig and not greater than 1050 psig to ensure the right liquid density. Once the user has initiated the flow, the cryogenic fluid passes through the components within the controller such as the main flow valve(s) (FIG. 9), delivery channel flow valve(s) (FIG. 9), and the controller connector (FIG. 9). The cryogenic fluid flow continues through the catheter, which fluidly coupled to the controller, by flowing through the high-pressure catheter connector (FIG. 22), the delivery channel(s) (FIG. 18), and the cryogenic fluid delivery channel assembly (FIGS. 10B and 16). Once the cryogenic fluid reaches the cryogenic fluid delivery channel assembly, the sprayers (FIGS. 14A, 14B, 14C, 14D, 15A, and 15B) are configured to direct the cryogen to the probe's inner surface and to the probe wall which is in intimate contact with the gastrointestinal tissue. This initiates an evaporative process where the cryogenic fluid is converted into a gas increasing in temperature resulting from the cryogenic fluid's liquid evaporation where heat has been absorbed from the probe wall which is in intimate contact with gastrointestinal tissue. The exhaust valve controls are fluidly coupled to the catheter and control the gas outlet from the probe, through the shaft inner space (FIGS. 20 and 21) and into the exhaust chamber. The controller can be configured to automatically control the gas outlet from the probe (FIG. 12) through the exhaust valve (FIG. 9) before, during, and after the cryogenic fluid is flowing through the probe. The gas is conveyed back into the controller through the shaft inner space (FIGS. 20 and 21). The gas travels through the controller connector (FIG. 9), exhaust valve (FIG. 9), and into the exhaust chamber (FIG. 9). Any remaining cryogen left within the canister after completing treatment may be vented from the canister. The canister's venting conveys the cryogenic fluid directly into the exhaust chamber, where the fluid undergoes a phase change into gas. Once the gas has been contained within the exhaust chamber, it can be directed from the controller in several different ways. The exhaust from the system can be configured for direct or recovery of the gas.

The features of particular embodiments of the cryogenic catheter probe of the present disclosure are illustrated in FIGS. 10A-10B, 11, 12, 13, 14A-14D, 15A-15B, 16, 17A-17D, 18, 19, 20, and 21.

For example, as shown in FIGS. 10A, 11, 12, and 13, in one embodiment, the disclosure provides cryogenic catheter probe 17 (also referred to as a catheter) that includes chamber 20 (also referred to as a probe) and channel assembly 19 (also referred to as a cryogenic fluid delivery channel assembly) housed within chamber 20. Chamber 20 includes a distal end, a proximal end, and a hollow body portion disposed between the distal and proximal ends. The distal end of the chamber is adapted for connection with distal probe tip 18. The proximal end of chamber 20 is adapted for connection with shaft 22. As noted, as shown in FIGS. 10A, 11, 12, and 13, chamber 20 corresponds with probe 20, with the distal end being the tapered portion on the left end of probe 20 and the proximal end being the tapered portion on the right end of probe 20. Specifically, as depicted in FIGS. 10A, 11, 12, and 13, the distal end of the chamber 20 (probe 20) is connected to distal probe tip 18 and the proximal end of the chamber 20 (probe 20) is connected to shaft 22. The hollow body portion of chamber 20 (probe 20) is the portion of chamber 20 that disposed between the distal and proximal ends, as noted above.

As shown in FIGS. 10B, 14A-14D, 15A, 15B, 16, 17A-17D, 18, 19, 20, and 21, channel assembly 19 includes: (i) central rail 21; (ii) at least one cryogenic fluid delivery channel 44 comprising a fluid delivery channel portion and sprayer 42 connected to the distal end of the fluid delivery channel portion. The at least one cryogenic fluid delivery channel 44 can be mounted on central rail 21 for longitudinal movement along central rail 21; (iii) delivery channel guide 43 for guiding the at least one cryogenic fluid delivery channel 44 longitudinally along central rail 21 during operation of probe 17; and (iv) sprayer guide 46 for guiding sprayer 42 of the at least one cryogenic fluid delivery channel 44 longitudinally along central rail 21 during operation of probe 17. Sprayer 42 can be configured to release cryogenic spray (also referred to as cryogenic fluid or liquid 51) in at least one treatment zone along hollow body portion of chamber 20.

The features of particular embodiments of the cryogenic ablation system of the present disclosure are illustrated in FIGS. 1, 3, 4, 5, 6, 7, 8A, and 9.

For example, as shown in FIGS. 1, 3, 4, 5, 6, 7, 8A, and 9, the present disclosure provides cryogenic ablation system 1. Cryogenic ablation system 1 includes cryogenic catheter probe 17, 20 as disclosed herein; a catheter portion 4 functionally connected to cryogenic catheter probe 17, 20; and controller 2 configured to control the functionality cryogenic catheter probe 17, 20.

The materials and methods of making the cryogenic catheter probe and cryogenic ablation system of the present disclosure are those materials and methods suitable for making catheters, controllers, catheter probes, and other related aspects as described herein and as described in the art.

Uses of the Cryogenic Catheter Probe and Cryogenic Ablation System of the Present Disclosure The present disclosure relates to, inter alia, methods, devices, and systems including a catheter and controller for the treatment of metabolic conditions including and not limited to Type 2 diabetes, obesity, hypertension, non-alcoholic fatty liver disease, acid reflux, Barrett's esophagus, etc., through efficiently ablating the luminal layers of the esophagus, stomach, pylorus, duodenum, or jejunum. Structures affected by the invention includes the mucosa, submucosa, and/or muscularis layers. Other structures within the layers may also be affected by the invention include vasculature and/or nerve tissue. For this invention, application of cryogen fluid through the introduction into an expandable probe in intimate contact with the mucosa of the small intestine, stomach, and/or the esophagus leads to remodeling of the intestinal tissue. The effect is from the mucosa and into the submucosa where critical microvasculature in the submucosa is preserved.

Upon delivery of the cryogenic fluid during treatment, liquid cryogen makes contact with the inside of the probe wall causing cells in proximity to the ablation interface (the interface of the probe wall and the contacted tissue or the inner layer of the mucosa) to undergo rapid freezing rates, whereas cells in the periphery of the ablation interface (submucosa and deeper layers of the wall of the small intestine) between the probe and the mucosa in intimate contact undergo moderate to lower freezing rates.

Cryoablation has been successfully used to remove or reduce unwanted tissue with positive remodeling resulting in normal tissue. As an example, cryo has been found to be useful in the reduction of keloid scar lesion. Application of a freezing temperature will cause cellular death and reduction of unwanted tissue. During regeneration, the acellular extracellular matrix remains intact and allows for cellular regeneration to occur. This positive remodeling for treatment of metabolic conditions through cryoablation of the luminal layers of the esophagus, stomach, pylorus, duodenum, or jejunum may impact several mechanisms such as modifying enteroendocrine signaling, disrupting or remodulating afferent nerve terminals located in the duodenum, improving the mucosal barrier whereby improving absorption mechanisms of the stomach, duodenum, and jejunum, along with other mechanisms.

EECs (Enteroendocrine cells) in the mucosa play a key role in gut hormone signaling for regulating insulin, satiety, and gut movement. Ablating the mucosal layer of stomach, duodenal, and jejunum where enterocytes may rejuvenate and repopulate the mucosa (i.e., duodenal mucosa) with "healthier" EECs, resulting in improved regulation of glucose uptake and transportation. EECs localization is sparse and irregular in the mucosal epithelium. Proposed changes in mechanism of action may occur with the cryoablation of ECCs at the stomach, duodenum, and jejunum.

Cryoablation in the stomach, duodenum, and jejunum submucosal layer may potentially be therapeutic. The energy delivery can facilitate modulation of the submucosal plexus (partial or reversable ablation, blocking, stimulation) along with mild modulation to the myenteric plexus (partial or reversable ablation, blocking, stimulation), while leaving critical microvascular and structural proteins intact which are necessary for regeneration. Improved brain-gut signaling (chemo-receptors) may occur post cryoablation. Additionally, the effect to afferent nerve terminals at the duodenum would produce similar effect as disruption of the CCK, GIP.

Upon duodenal-jejunal bypass surgery, epithelial proliferation and tight junction expression are increased, which subsequently leads to decreased intestinal permeability. In line with this observation, RYGB surgery is associated with decreased endotoxemia in patients with obesity and T2DM. The rapid freezing rates delivered to mucosal tissue modifies integrity and function of the intestinal barrier (mucosal epithelium) wherein the target mucosa intercellular spaces (ICS) decrease, and MI (mucosal impedance) increase thereby decreasing the permeability in mucosa ablated.

The Wall of the Small Intestine:

The main functions of the small intestine are digestion, absorption of food and the production of gastrointestinal hormones. The duodenal wall is made of four tissue layers that are consistent with the structure of the rest of the gastrointestinal tract including the esophagus, stomach, and jejunum.

Figure 26:
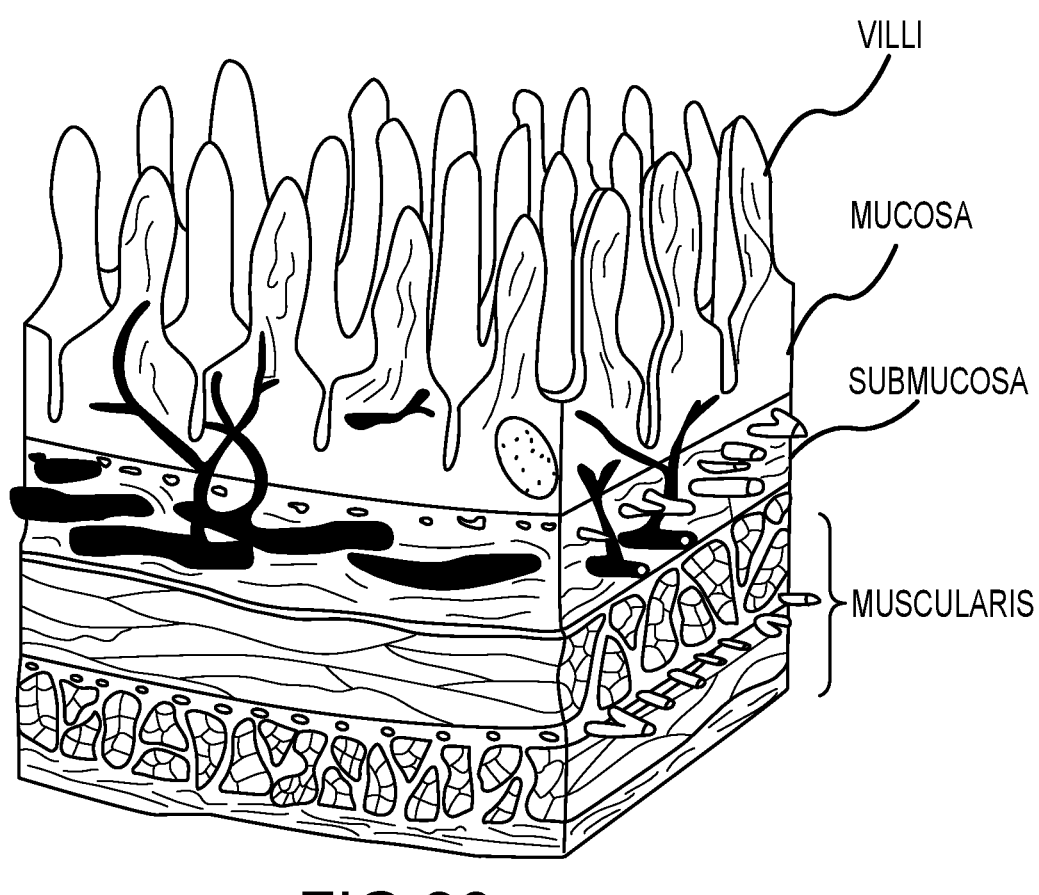
FIG. 26 is an illustration of the wall of the duodenum.
Figure 27:
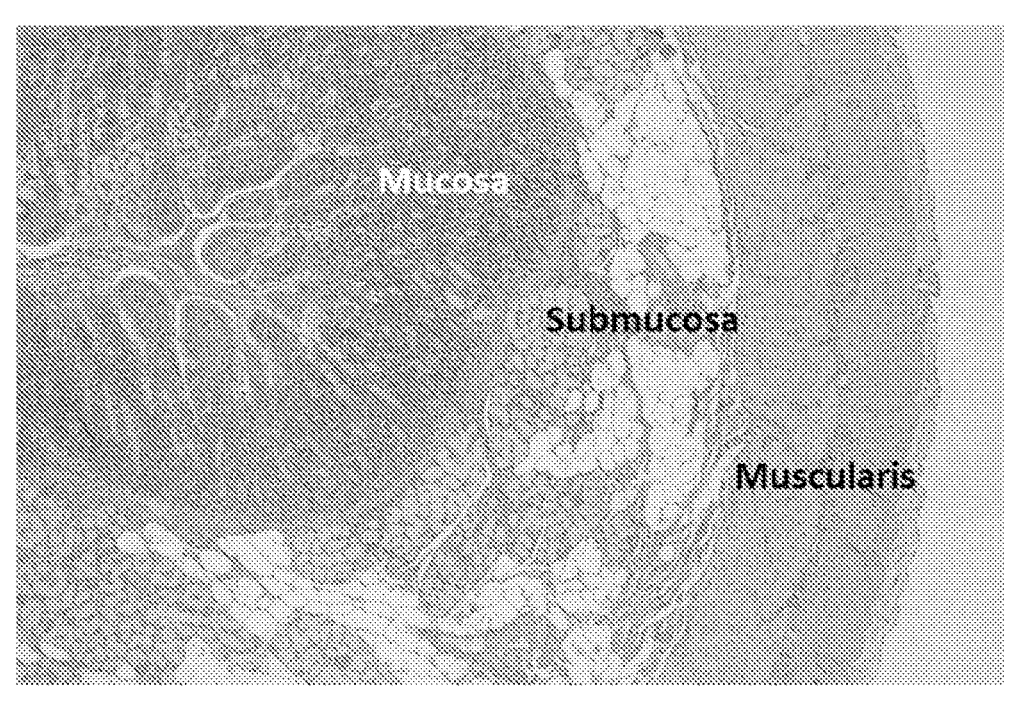
FIG. 27 is a detailed cross-sectional image of duodenal tissue.

Referring to FIG. 26 and FIG. 27, the mucosa is the inner most layer which lines the inner surface of the duodenum and is in contact with chyme passing through the intestinal lumen. The mucosa is highly folded to increase surface area for nutrient absorption. Villi, which are smaller folds, are finger like mucosal projections. Columnar epithelial cells lining the surface have fine projections called microvilli which further increase the surface area and improve the absorption of nutrients. Plentiful mucus glands secrete mucus into the lumen to lubricate the intestinal wall and protect it from friction and acidic chyme (partially digested food).

Surrounding the mucosa layer is the submucosa, a layer of connective tissue that supports other tissue layers. Many blood vessels and nerve structures pass through the submucosa, specifically a network of nerve fibers and neuronal cell bodies called the submucosal plexus are present within the submucosa.

The muscularis layer surrounds the submucosa. This layer contains the smooth muscle tissue where the inner portion is a circular muscle layer, and the outer portion is a longitudinal layer of smooth muscle. The two layers of muscle in the muscularis layer sandwich the myenteric plexus that contains nerve fibers and parasympathetic ganglia.

Lastly, the serosa is the outermost layer of the duodenum that acts as the outer protective surface of the intestine. The serosa is comprised of loose connective tissue and a thin mesothelial cell layer, providing a smooth, slick surface to prevent friction between the duodenum and the surrounding organs.

Mechanisms of Action of the Cryogenic Catheter Probe and Cryogenic Ablation System of the Present Disclosure:

For this invention, application of cryogen fluid through the introduction into an expandable probe making intimate contact with the mucosa of the small intestine and/or the stomach leads to remodeling of the intestinal tissue. The effect is from the mucosa and into the submucosa where critical microvasculature in the submucosa is preserved. Remodeling of the mucosa is targeted at EECs which plays a key role in gut hormone signaling for regulation of insulin, satiety, and gut movement. Improper signaling by the EECs may lead to altered insulin production and/or function resulting in hyperglycemia. Additionally, remodeling of the duodenal mucosa relates to the disruption of the nerve terminals and plexus located in the mucosa.

Temperature decrease to the submucosa is therapeutic in the sense that the energy delivery facilitates modulation of the nerves of the submucosa (partial or reversable ablation, blocking, stimulation) while leaving critical microvascular and structural proteins intact which are necessary for regeneration. Additionally, cryoablation has been observed to not produce coagulative effect; thus, resulting in a lower incidence of thrombus formation as compared to RF and other high-temperature ablation technologies.

Further, the rapid freezing rates delivered to mucosal tissue modifies integrity and function of the intestinal barrier (mucosal epithelium) wherein the target mucosa intercellular spaces (ICS) decrease, and MI (mucosal impedance) increase thereby decreasing the permeability in mucosa ablated.

Cryoablation results in a robust inflammatory response, particularly in the submucosa. The inflammatory response signals for the clearing of damaged cellular debris and initiation of tissue remodeling. Commonly employed ablation therapies in the clinical setting are radiofrequency ablation (RFA), microwave ablation, high-intensity focused ultrasound, laser, steam, hot-balloon and cryoablation. All these treatments operate on the principle of hyperthermia except for cryoablation, which is a hypothermic modality that induces tissue damage by a freeze-thaw process.

Similar to the microvasculature, cryoablation causes minimal disruption to the extracellular matrix (ECM) allowing for remodeling of the tissue layers with minimal to no fibrotic scar formation. An intact ECM provides cells with a scaffold for cellular migration, proliferation, and differentiation for tissue renewal.

Figure 28:
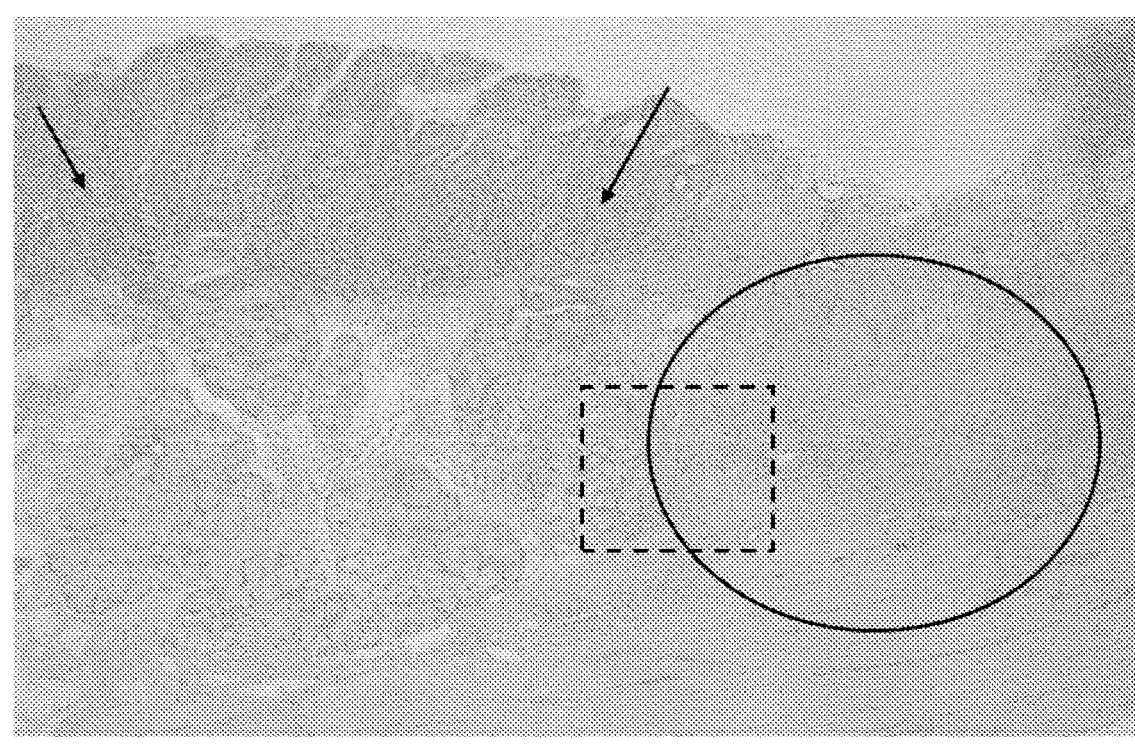
FIG. 28 is a detailed cross-sectional image of duodenal tissue, low magnification at 4 days post treatment.
Figure 29:
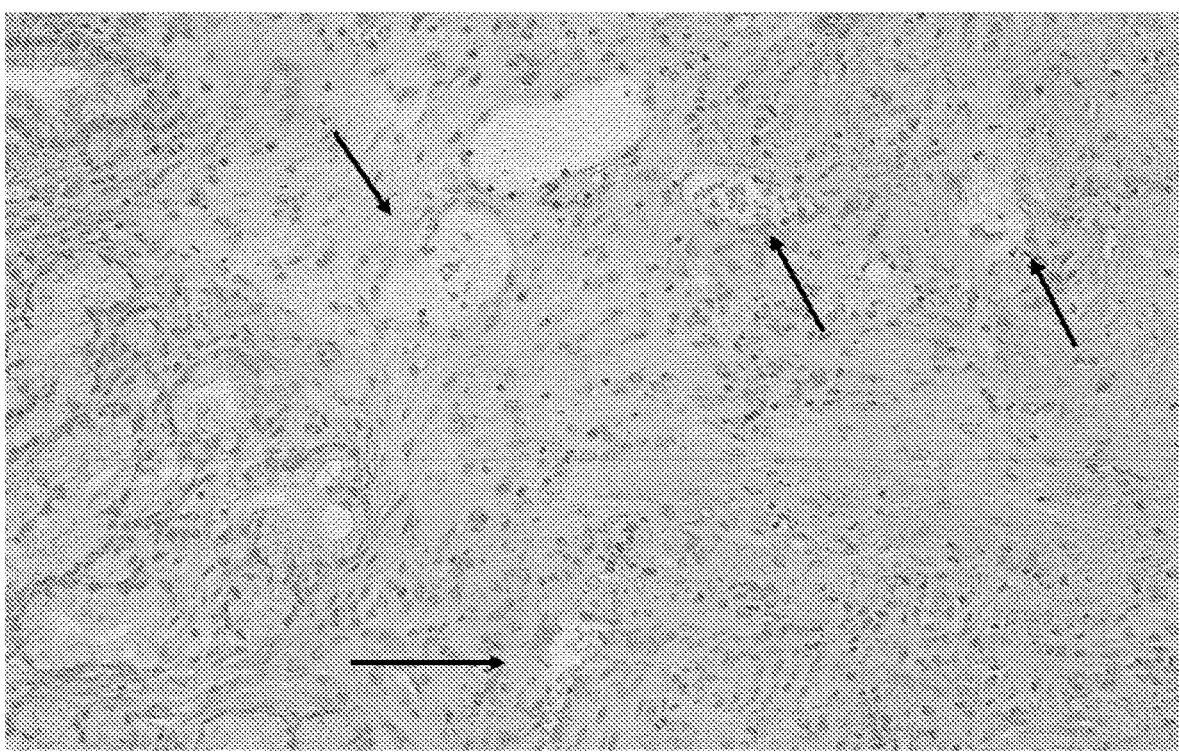
FIG. 29 is a detailed cross-sectional image of duodenal tissue, high magnification at 4 days post treatment.

Referring to FIG. 28, a low magnification, H&E stain, represents a partial thickness section of the duodenum, at the edge of a cryoablation site at Day 4. The untreated intact mucosal epithelium is indicated by black arrows, and the ablation site, with loss of the mucosal epithelium and submucosal glands is the area within the black circle. Referring to FIG. 29. is a higher magnification of the black dashed box in FIG. 28, H&E stain, demonstrating viable blood vessels within the submucosa (black arrows). These blood vessels proliferate in conjunction with fibroblasts, forming granulation tissue at the ablation site associated with the healing response. Collagen bundles form part of the ECM associated with healing and tissue regeneration at the cryoablation site.

Cryoablation has been successfully used to remove or reduce unwanted tissue with positive remodeling of normal tissue. As an example, cryo has been found to be useful in the reduction of keloid scar lesion. Application of a freezing temperature will cause cellular death and reduction of unwanted tissue. During regeneration, the acellular extracellular matrix remains intact and allows for cellular regeneration to occur.

Cryoablation induces cell necrosis for therapeutic purposes through cycles of controlled local freezing and thawing of the tissue. Application of freezing temperatures to tissue result in necrosis of mucosal and submucosal layers by several mechanisms. Freezing of tissue results in the formation of ice crystals within the intracellular and extracellular spaces, leading to cell membrane disruption, protein denaturation, and osmotic gradients that lead to cell dehydration. This leads to necrosis in which intracellular contents (e.g., DNA, RNA and other intracellular contents) are released, and leading to an immune response. Cells in the periphery of ablation zones that are not immediately destroyed by direct cryoablation-induced injury may subsequently die by apoptosis, thought to be mediated by cytochrome C release. The thawing component of cryotherapy also appears to be an important mechanism for cell death. During thawing, ice crystals fuse and further damage cell membranes. In addition, vascular stasis due to endothelial damage, platelet aggregation, and formation of microthrombi results in ischemic necrosis. For cell destruction by cryotherapy, the tissue temperature must reach a critical threshold that is unique to the cell type and the environment of the targeted tissue, but typically ranges below freezing may be effective. Because collagen and elastin fibers are less sensitive to the effects of cryotherapy than are epithelial cells, the tissue structure remains intact, reducing the risk of perforation. The extent of tissue destruction is also dependent on the number of freeze/thaw cycles applied.

Gastrointestinal Role in Enteroendocrine Regulation

Figure 30:
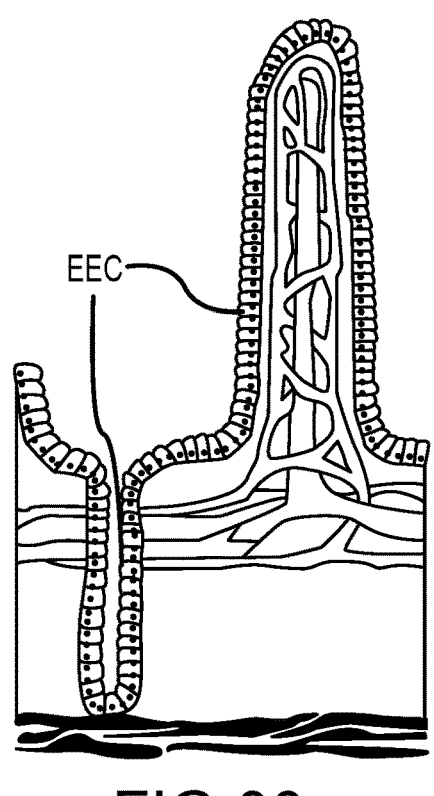
FIG. 30 is an illustration of the wall of the duodenum with emphasis on villi and crypts.

Enteroendocrine cells (EEC) are widely distributed throughout the gastrointestinal (GI) mucosa in crypts and villa, represent 1% of the total gut epithelium cell population, and form the largest endocrine organ in the body. Referring to FIG. 30 the illustration of an isolated villus and crypt. There is a wide distribution of EECs in the villi and crypts which are demonstrated and where the EECs interspersed between non endocrine cells. EECs comprise different subgroups producing and releasing a variety of hormones under appropriate stimulation. EECs are largely distributed in the gut. In addition, Arteriole and Venule are shown along with a lymphatic vessel.

Figure 31:
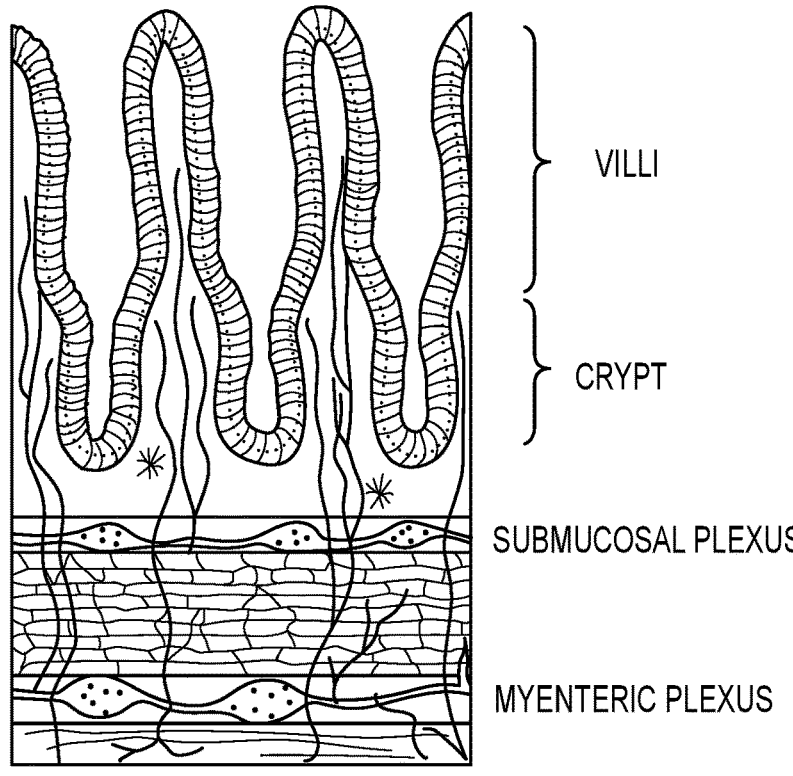
FIG. 31 is an illustration of the wall of the duodenum with emphasis on submucosa plexus and myenteric plexus.

Referring to FIG. 31, the layers of the wall of the duodenum are represented. The anatomy of intestinal epithelium includes the mucosa depicting villi differentiated cell types and crypts. The submucosa containing submucosal plexus is depicted where intrinsic nerves from the submucosal plexus run from the submucosa into the villa in the mucosal layer. From the myenteric plexus, which is found between the circular muscle and the longitudinal muscle, run intrinsic nerves into the villa of the mucosa.

EECs plays a key role in gut hormone signaling for regulation of insulin, satiety, and gut movement. Improper signaling by the EEC may lead to altered insulin production and/or function resulting in hyperglycemia. Additionally, EECs are responsible for postprandial regulation of glucose level and metabolism. The EECs detects luminal content and release signaling molecules that can enter the circulation to act as classic hormones on distant targets, act locally on neighboring cells and on distinct neuronal pathways including enteric and extrinsic neurons.

EECs secrete more than 20 types of peptides/hormones. These secretory products can act locally in a paracrine manner, activating other EECs and other cell types in the mucosa, in addition, reach distant targets through release into the bloodstream or act directly on nerve endings close to the site of release. EEC secretory products are released in response to diverse types of stimuli and influence a variety of physiological functions. For example, GLP-1, glucagon like peptide-2 (GLP-2) and PYY, are contained in open type L cells and are released in response to ingested nutrients, including carbohydrates and fat.

Recent studies have shed light on EEC sensory transmission by showing direct connections between EECs and the nervous system via axon-like processes that form a well-defined neuroepithelial circuits through which EECs can directly communicate with the neurons innervating the GI tract to initiate appropriate functional responses.

In comparison to the distal gut, most ingested nutrients are absorbed within the proximal small intestine. The upper small intestine receives more vagal afferent innervation, which forms part of a neural circuit that mediates satiety; particularly, the duodenum is richly innervated by the parasympathetic nervous system which makes up the enteric nervous system (ENS). Sensory afferent neurons are the primary sensors and regulators that detect luminal contents. The afferent neurons transmit information to the brain, resulting in a gut response such as motility, intestinal barrier function, and epithelial secretion. Additionally, this system is a key regulator of insulin production and glycemic management. Dysfunction of the signaling pathway can lead to improper insulin production, leading to T2DM.

Sensory neurons, a subclass of enteric neurons, are the primary sensors and regulators of the ENS that detect luminal contents. These neurons respond to mechanical and chemical stimuli by activating intestinal muscles and controlling secretion of enzymes, hormones (by endocrine cells) and neurotransmitters. The ENS transmits information to the central autonomic nervous system through afferent nerves of the small intestine which correspond with specific areas in the brain (the well-known gut-brain axis). These areas are involved in metabolic regulation through controlling the function of splanchnic organs, such as the liver and endocrine pancreas, and the regulation of appetite and satiation. Interestingly, insulin has a direct regulatory effect on this pathway, resulting in the inhibition of food intake and weight control.

Additionally, it has been observed that a high-fat diet and T2D correlate with presence of neuropathy in the duodenal myenteric plexus, a decrease in the supporting enteric glial cells, and the loss of duodenal neurons. Recovery of these neuronal pathways can be achieved; it has been suggested that both RYGB and vertical sleeve gastrectomy lead to improved energy homeostasis and metabolism by manipulation of vagal afferent fibers of the ENS.

The vagal afferent innervation of the antral mucosa consists of fibers that pass through the submucosa to the level of the muscularis mucosa, where the neurites then arborize extensively Because these neuronal GLP-1 projections (see below) receive input from the gut via vagal afferents, likely including GLP-1 sensitive afferents from the intestinal mucosa and the hepato-portal vein, they might be considered as an additional mechanism for amplification of the rapidly fading peripheral GLP-1 signal.

Cryomodulation of Enteroendocrine Signaling:

Targeted treatment of the EECs in the duodenum can improve glycemic regulation by altering endocrine signaling. This section provides details of the proposed changes to EEC signaling pathways with cryotreatment of the invention.

A. Enteroendocrine Hormones and the Incretin Effect

There are various enteroendocrine hormones that have been observed to play a role in nutrient detection, motility, secretion, inflammatory response, satiety, and insulin regulation. Glucagon-like peptide 1 (GLP-1) and gastric inhibitory polypeptide (GIP) are key incretin hormones that are intimately involved in the regulation of glucose homeostasis. Endocrine L and K cells are located throughout the small intestine, and they secrete gut hormones in the presence of nutrients in the lumen. K cells are predominantly found in the duodenum and secretes GIP in response to luminal carbohydrate, dietary lipid and glucose. GLP-1 are contained in open type L cells which are found in the small intestine and the colon and are released in response to ingested nutrients, including carbohydrates and fat.

These incretin hormones ensure that postprandial glucose levels do not increase excessively. Referred to as the incretin effect, oral carbohydrate administration stimulates the secretion of GIP (glucose-dependent insulinotropic polypeptide) and GLP-1 which stimulate insulin secretion, and the stimulated insulin secretion, in turn, is responsible for the increased disposal of glucose.

It has been demonstrated that the incretin effect is severely reduced or even absent in patients with type 2 diabetes, even in patients with a considerable insulin secretory capacity. The incretin deficiency is therefore one of the most important pathogenetic factors behind the impaired glucose tolerance in this disease.

B. Anti-Incretin Effect

Glucose regulation not only depends on the amount of GLP-1 and GIP being secreted, but also the number of active hormones available to promote insulin secretion. Both GLP-1 and GIP are rapidly degraded by the enzyme DPP-4 (Dipeptidyl peptidase-4), which is an anti-integrin broadly expressed on cell surfaces and present in the circulation. GLP-1 is rapidly cleaved by the DPP-4 into GLP-1(9-36), which exhibits its own biological activities (albeit not insulin secretion anymore). GIP is also cleaved by DPP-4 into inactive GIP(3-42). As a result, the majority of GLP-1 and GIP is inactivated before reaching the systemic circulation; inhibiting the insulinogenic effect. DPP-4 inhibitors are a class of drugs commonly used to treat T2DM by reducing the inactivation of GLP-1, resulting in reduced levels of blood glucose.

C. Cryoablation of Duodenum and Stomach

It is proposed that the cryotreatment of the duodenum and/or stomach may provide a similar effect as RYGB. In the short-term, nutrients that are not absorbed due to the ablation of the upper small intestine and stomach will primarily be absorbed in the lower portion. Disrupting the tissue at the upper small intestine and stomach may inhibit its response nutrient contact. This could lead to an exaggerated secretion of GLP-1 and increased signaling for insulin secretion. Further, ablation of K-cells and L-cells can lead to a general 'reset' of their function to potentially allow for a return to an appropriate endogenous secretion of both GLP-1 and GIP; thus, leading to improved glucose regulation. Finally, ablation of the cells at the duodenum and/or stomach can reduce the anti-incretin release. The lack of the anti-incretin (DPP-4) release will allow for continued signaling for insulin secretion by GLP-1 and GIP.

D. Other Enteroendocrine Hormones

Although GLP-1 and GIP may be the key hormones in glucose modulation, there are various other enteroendocrine hormones known to contribute to glucose modulation. Enteroendocrine play different roles during different states of digestion, ranging from fasting, during nutrient consumption, and postprandial. One example is Ghrelin which is secreted by A-cells which are found in the stomach corpus.

Ghrelin is one of the circulating peptides, which stimulates appetite and regulates energy balance, and thus is connected to obesity and T2DM. Both basic research and genetic association studies have revealed association between the ghrelin gene and obesity, metabolic syndrome or T2DM. Postprandial plasma ghrelin is suppressed proportional to meal calorie content in normal weight but not in obese subjects, which suggest that food intake fails to suppress ghrelin levels in obese humans. Ghrelin secretion may be decreased after RYGB because of denervation of autonomic input to ghrelin cells in the stomach. Ablation of the mucosa in the stomach may disrupt the Ghrelin secretion in the duodenum and/or signaling of the ghrelin receptors.

Figure 32:
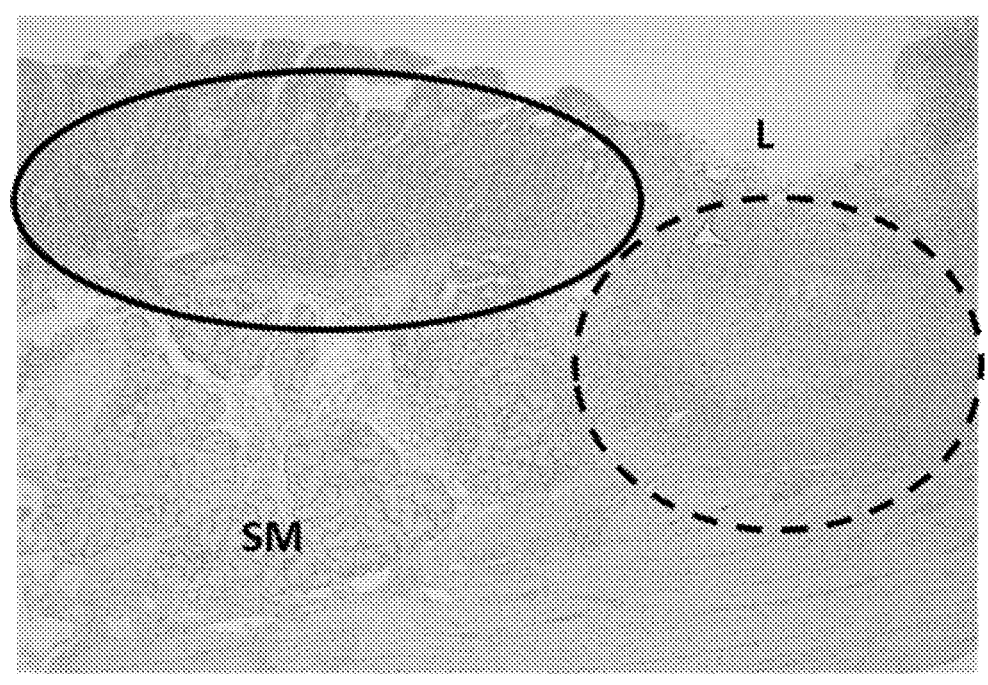
FIG. 32 is a detailed cross-sectional image of duodenal tissue, low magnification at 4 days post treatment.

Referring to FIG. 32, is an image of duodenal tissue which has undergone cryoablation 4 days previous and next to duodenal tissue which has not undergone cryoablation. The image is highly magnified histography where in the treated portion includes the treated mucosa, treated villus and crypts which include partial sloughing and regeneration.

Referring to FIG. 32, H&E stain, is an image of duodenum (partial thickness), which demonstrates the edge of the cryoablation site at Day 4. Note the untreated intact mucosal epithelium that this viable (black circle), and the area of cryoablation with sloughing of the much of the mucosal epithelium and necrosis and loss of submucosal glands (dashed black circle). Normal viable submucosal glands are indicated by "SM", and the lumen of the duodenum by "L". The area of cyroablation demonstrates loss of the treated area of mucosal epithelium, representing the villi and crypts, which include mucosal epithelial cells, secretory goblet cells, and the EECs.

Figure 33:
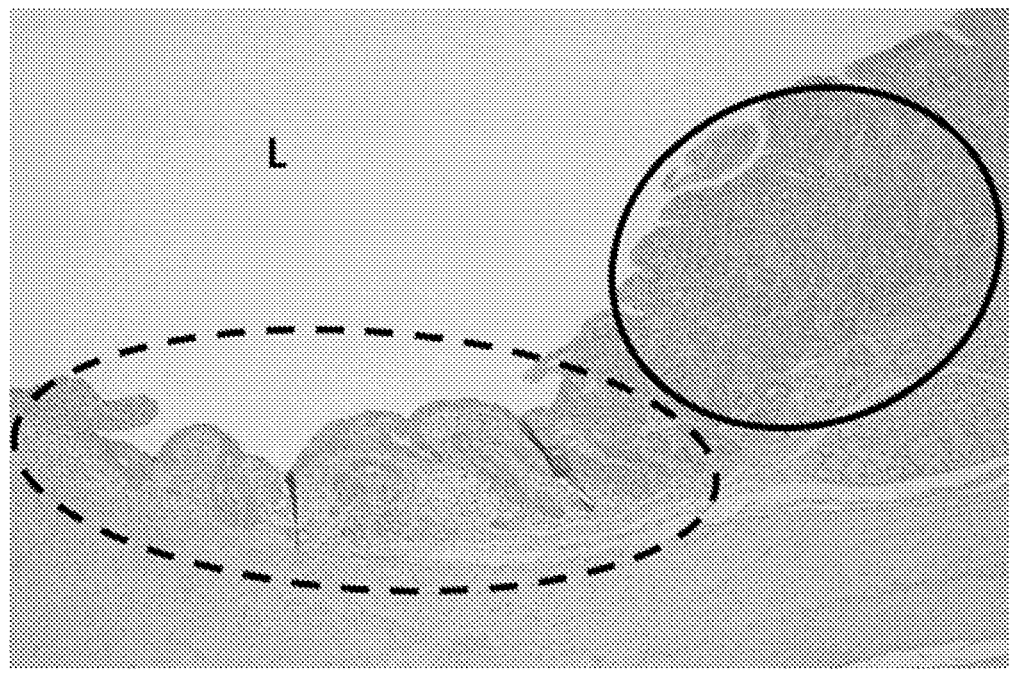
FIG. 33 is a detailed cross-sectional image of duodenal tissue, low magnification at 30 days post treatment.

Referring to FIG. 33, H&E stain, is an image of the duodenum (partial thickness), which demonstrates the edge of the cryoablation site at Day 30. Note the untreated intact mucosal epithelium that is viable (black circle), and the area of mucosal regeneration, with early formation of villi and crypts (dashed black circle). This area of mucosal regeneration represents proliferation of mucosal epithelial cells, secretory goblet cells, and expected EECs. The lumen of the duodenum is indicated by "L".

Disruption of Enteric Nervous System:

The upper small intestine is highly innervated by the afferent nerves which forms part of neural circuit that is responsible for motility, secretion, inflammatory response, satiety, and insulin regulation. The parasympathetic nervous system makes up the enteric nervous system (ENS), which is responsible for the complex signaling by the enteroendocrine hormones. The vagal afferent innervation of the submucosal plexus consists of fibers that pass through the submucosa to the level of the muscularis mucosa, where the neurites then arborize extensively. The plexus includes chemoreceptors and mechanoreceptors which provide input signals to the ENS. As a whole, these afferent neurons transmit information to determine the gut response; such as motility, intestinal barrier function, and epithelial secretion. The ENS transmits information to the central autonomic nervous system through afferent nerves of the small intestine which correspond with specific areas in the brain (the well-known gut-brain axis). Additionally, this system is a key regulator of insulin production and glycemic management. Dysfunction of the signaling pathway can lead to improper insulin production, leading to T2DM.

Cryotreatment of peripheral nervous tissue has been commonly performed for various medical therapies (e.g., pain management and movement disorders). Different strategies in cryoablation of the nerve cause varying levels conduction disruption, ranging from temporary to permanent denervation. The proposed device can disrupt the nerve terminals and plexus located in the mucosa and/or the submucosa. The cryotreatment can induce a process known as Wallerian degeneration. This process involves the degeneration of the nerve axon and disruption of nerve conduction signals. This disruption can modify enteric nervous response and improve insulin sensitivity like the effects seen in duodenal bypass. Appropriate cryotreatment of the nerve may allow the epineurial structure to remain intact; thereby, providing scaffolding for axonal regeneration to occur. It is believed that the disruption to the nerves in the duodenum can disrupt the signal; like what is observed in RYGB and vertical sleeve gastrectomy patients who show improved energy homeostasis and metabolism by manipulation of vagal afferent fibers of the ENS.

Temperature decrease to the submucosa is therapeutic in the sense that the energy delivery facilitates modulation of the submucosal plexus (partial or reversable ablation, blocking, stimulation) while leaving critical microvascular and structural proteins intact which are necessary for regeneration. Additionally, cryoablation has been observed to not produce coagulative effect; thus, resulting in a lower incidence of thrombus formation as compared to high-temperature based ablation.

Figure 34:
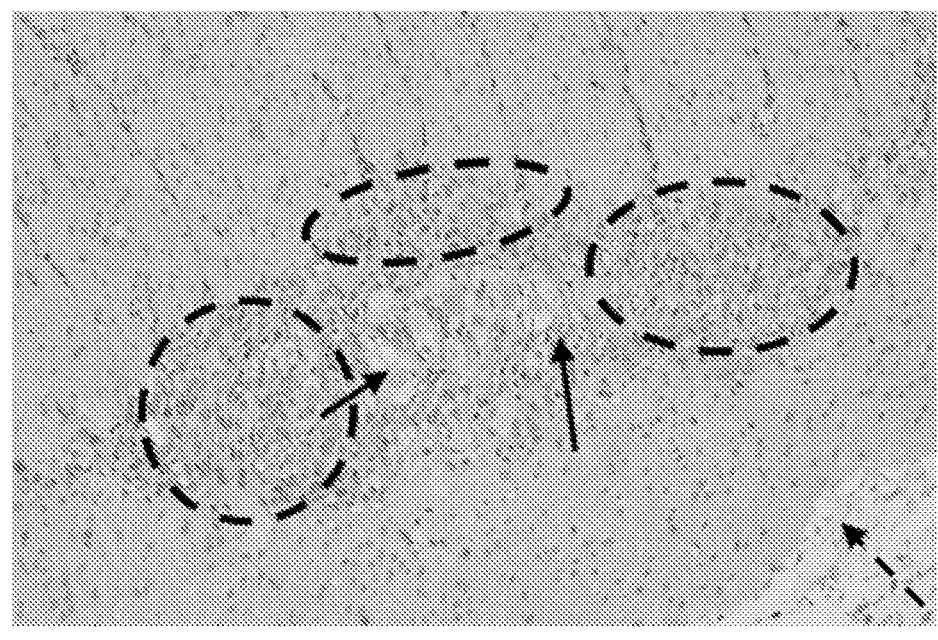
FIG. 34 is a detailed cross-sectional image of duodenal tissue, high magnification at 4 days post treatment with emphasis on myenteric plexus between the inner and outer smooth muscle layers.
Figure 35:
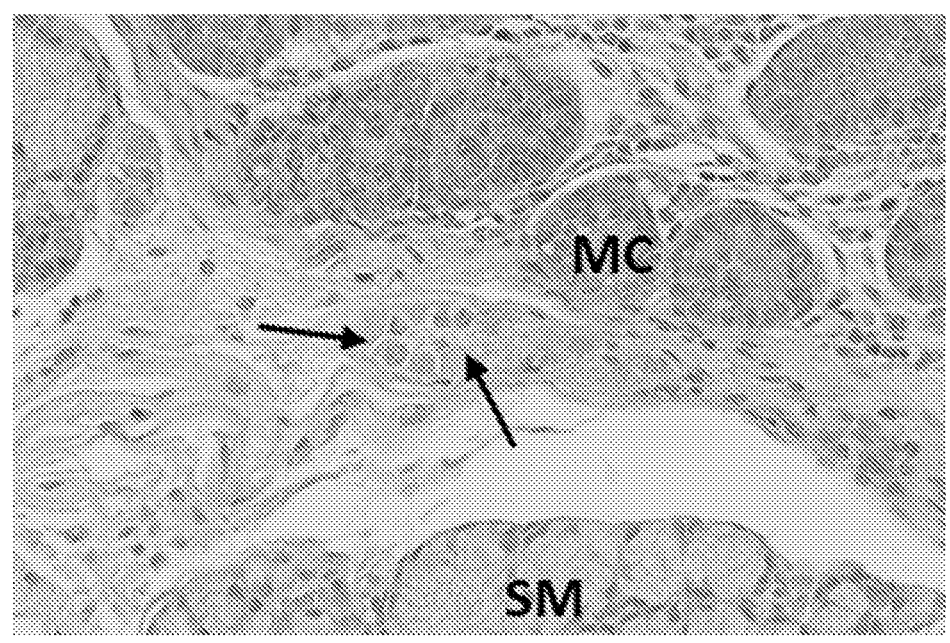
FIG. 35 is a detailed cross-sectional image of duodenal tissue, high magnification at 4 days post treatment with emphasis on submucosal plexus, adjacent to a cryoablation treatment site.

Referring to FIG. 34, H&E, high power image of a myenteric plexus between the inner and outer smooth muscle layers of the muscularis externa, adjacent to a cryoablation treatment site, at Day 4. Ganglia within the plexus exhibit mild to moderate vacuolation of the cytoplasm (black arrows), which histologically appears as clear cytoplasmic spaces. This vacuolar change represents a nonspecific degenerative process, indicative of injury within the enteric nervous system associated with cryoablation. There is a mild to moderate inflammatory infiltrate surrounding the plexus (lymphocytes and lesser plasma cells) indicated by black dashed circles. The serosal surface is indicated by the dashed black arrow. Adjacent smooth muscle of the muscularis externa is normal and viable Referring to FIG. 35, high power image of a submucosal plexus, adjacent to a cryoablation treatment site at Day 4. Ganglia within the plexus exhibit mild vacuolation of the cytoplasm (black arrows), consistent with a degenerative change, indicative of injury within the enteric nervous system associated with cryoablation. Note, normal adjacent submucosal glands (SM), and mucosal crypts. (MC)

REFERENCES

Citation of a reference herein shall not be construed as an admission that such reference is prior art to the present invention. All references cited herein are hereby incorporated by reference in their entirety. Below is a listing of various references cited with respect to this example:

1. www.betterhealth.vic.gov.au/health/conditionsandtreatments/diabetes-long-term-effects
2. Liebl A, Mata M, Eschwege E. Evaluation of risk factors for development of complications in Type II diabetes in Europe. Diabetologia 2002; 45:S23-S28.
3. Sjöström L, Lindroos A K, Peltonen M, et al. Lifestyle, diabetes, and cardiovascular risk factors 10 years after bariatric surgery. N Engl J Med 2004; 351:2683-93.
4. Pories W J, Albrecht R J: Etiology of type 2 diabetes mellitus: role of the foregut. World J Surg 25:527-531, 2001

5. Betzel B, Cooiman M I, Aarts E O, Janssen I M C, Wahab P J, Groenen M J M, Drenth J P H, Berends F J. Clinical follow-up on weight loss, glycemic control, and safety aspects of 24 months of duodenal-jejunal bypass liner implantation. Surg Endosc. 2020 January; 34(1):209-215.

6. Zervos E E, Agle S C, Warren A J, Lang C G, Fitzgerald T L, Dar M, Rotondo M F, Pories W J. Amelioration of insulin requirement in patients undergoing duodenal bypass for reasons other than obesity implicates foregut factors in the pathophysiology of type II diabetes. J Am Coll Surg. 2010 May; 210(5):564-72, 572-4. doi: 10.1016/j.jamcollsurg.2009.12.025. PMID: 20421005.

7. Cherrington A D, Rajagopalan H, Maggs D, Devière J. Hydrothermal Duodenal Mucosal Resurfacing: Role in the Treatment of Metabolic Disease. Gastrointest Endosc Clin N Am. 2017 April; 27(2):299-311. doi: 10.1016/j.giec.2016.12.002. PMID: 28292408.

8. van Baar A C G, Holleman F, Crenier L, et al. Endoscopic duodenal mucosal resurfacing for the treatment of type 2 diabetes mellitus: one year results from the first international, open-label, prospective, multicentre study. Gut. 2020; 69(2):295-303. doi:10.1136/gutjnl-2019-318349.

9. ClinicalTrials.gov Identifier—NCT03390322 (clinicaltrials.gov/ct2/show/NCT03390322)

10. Reserved

11. Reserved 12. van Baar A C G, Nieuwdorp M, Holleman F, Soeters M R, Groen A K, Bergman J J G H M. The Duodenum harbors a Broad Untapped Therapeutic Potential. Gastroenterology. 2018 March; 154(4):773-777-

13. Dhaliwal_Mol275 Comparative Assessment of the Structural and Functional Integrity of the Neo-Squamous Epithelium following endoscopic therapy in Barrett's esophagus: A Pilot Study, GIE, POSTER ABSTRACTS1 VOLUME 91, ISSUE 6, SUPPLEMENT, AB412, 2020.

14. Erinjeri J P, Clark T W. Cryoablation: mechanism of action and devices. J Vasc Interv Radiol. 2010 August; 21(8 Suppl):5187-91. doi: 10.1016/j.jvir.2009.12.403. PMID: 20656228; PMCID: PMC6661161.

15. Yakkala C, Chiang C L, Kandalaft L, Denys A, Duran R. Cryoablation and Immunotherapy: An Enthralling Synergy to Confront the Tumors. Front Immunol. 2019 Sep. 24; 10:2283.

16. Erinjeri J P, Clark T W. Cryoablation: mechanism of action and devices. J Vasc Interv Radiol. 2010 August; 21(8 Suppl):5187-91. doi: 10.1016/j.jvir.2009.12.403.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Citation of a reference herein shall not be construed as an admission that such reference is prior art to the present invention. All references cited herein are hereby incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Although the present invention has been described for the purpose of illustration, it is understood that such detail is solely for that purpose and variations can be made by those skilled in the art without departing from the spirit and scope of the invention which is defined by the following claims.

What is claimed is:

1. A cryogenic catheter probe comprising:

a chamber comprising a distal end, a proximal end, and a hollow body portion disposed between the distal and proximal ends, wherein said distal end is adapted for connection with a distal probe tip, and wherein said proximal end is adapted for connection with a shaft; and a channel assembly housed within the chamber, said channel assembly comprising:

(i) a central rail;

(ii) at least one cryogenic fluid delivery channel comprising a fluid delivery channel portion and a sprayer connected to the distal end of the fluid delivery channel portion, said at least one cryogenic fluid delivery channel being mounted on the central rail for longitudinal movement along the central rail;

(iii) a delivery channel guide for guiding the at least one cryogenic fluid delivery channel longitudinally along the central rail during operation of the probe; and (iv) a sprayer guide for guiding the sprayer of the at least one cryogenic fluid delivery channel longitudinally along the central rail during operation of the probe, the sprayer guide comprising a central opening configured to fit around the central rail and an exterior or interior groove for the sprayer of at least one cryogenic fluid delivery channel to be guided thereby, wherein said sprayer is configured to release cryogenic spray in at least one treatment zone along the hollow body portion of the chamber.

2. The probe according to claim 1, further comprising a distal probe tip attached to the distal end of the probe.

3. The probe according to claim 1, wherein the delivery channel guide comprises a central opening configured to fit around the central rail and an exterior or interior groove of the at least one cryogenic fluid delivery channel to be guided thereby.

4. The probe according to claim 1, wherein the central opening of the sprayer guide is configured so that it prevents rotation of the sprayer guide around the central opening.

5. The probe according to claim 1, wherein the channel assembly comprises 1 to 20 cryogenic fluid delivery channels.

6. The probe according to claim 1, wherein the channel assembly comprises a number of cryogenic fluid delivery channels selected from the group consisting of 1, 2, 3, 4, 5, 6, 7, and 8 cryogenic fluid delivery channels.

7. The probe according to claim 1, wherein the number of interior or exterior grooves of the sprayer guide are the same as the number of cryogenic fluid delivery channels.

8. The probe according to claim 1, wherein the at least one cryogenic fluid delivery channel comprises at least two cryogenic fluid delivery channels, and wherein the sprayers of each of the cryogenic fluid delivery channels are configured to release cryogenic spray either in unison or independently of one another.

9. The probe according to claim 1, wherein the at least one cryogenic fluid delivery channel comprises at least two cryogenic fluid delivery channels, and wherein each sprayer is configured to release cryogenic spray in a different treatment zone along the probe.

10. The probe according to claim 1, wherein said catheter is configured for selective ablation in the mucosa and submucosa of a gastrointestinal tract of a subject.

11. The probe according to claim 1, wherein the at least one cryogenic fluid delivery channel comprises at least two cryogenic fluid delivery channels, wherein the cryogenic fluid delivery channels are independently controlled and turned to an on or off position.

12. The probe according to claim 1, wherein the treatment tissue comprises mucosal and/or submucosal tissue of the large intestine, small intestine, stomach, esophagus, rectum, and anus.

13. A cryogenic ablation system comprising:
a cryogenic catheter probe according to claim 1;
a catheter portion functionally connected to the probe; and
a controller configured to control the functionality of the cryogenic catheter probe.

14. A method of performing cryogenic ablation of mucosal tissue and/or of both mucosal tissue and submucosal tissue in the gastrointestinal tract of a subject, said method comprising:
(a) providing a cryogenic ablation system according to claim 13;
(b) contacting the cryogenic catheter probe of the system with a target treatment region of the gastrointestinal tract of the subject; and
(c) releasing a cryogenic fluid from the at least one sprayer to treat the target treatment region by cryogenically ablating at least a portion the mucosal tissue or ablating at least a portion of both the mucosal and submucosal tissue of the target treatment region.

15. The method according to claim 14, wherein the target treatment region comprises mucosal tissue and/or both mucosal and submucosal tissue of the large intestine, small intestine, stomach, esophagus, rectum, or anus of the subject.

16. The method according to claim 15, wherein treating the target treatment region comprises performing a series of tissue ablation steps, each comprising ablation of an axial length of the large intestine, small intestine, stomach, esophagus, rectum, or anus of the subject, wherein each ablation step is optionally preceded by a tissue expansion step.

17. A method for performing a medical procedure in a small intestine and/or stomach of a patient in need of said medical procedure, the method comprising:
(a) providing a cryogenic ablation system according to claim 13;
(b) contacting the cryogenic catheter probe of the system with a target treatment region of the small intestine and/or stomach of the patient; and
(c) releasing a cryogenic fluid from the at least one sprayer to treat the target treatment region by cryogenically ablating at least a portion the mucosal tissue or ablating at least a portion of both the mucosal and submucosal tissue of the target treatment region,
thereby performing a medical procedure to treat a condition of the patient selected from the group consisting of Type 1 diabetes, Type 2 diabetes, non-alcoholic fatty liver disease (NAFLD), non-alcoholic steatohepatitis (NASH), and obesity.

* * * * *